(12) United States Patent
Rao et al.

(10) Patent No.: US 12,241,058 B2
(45) Date of Patent: Mar. 4, 2025

(54) RECOMBINANT MICROBIAL SYSTEM FOR DIRECTED EVOLUTION OF GLYCOCINS AND METHOD OF PREPARATION THEREOF

(71) Applicant: COUNCIL OF SCIENTIFIC & INDUSTRIAL RESEARCH, New Delhi (IN)

(72) Inventors: Alka Rao, Chandigarh (IN); Pravinkumar Vishavanath Choudhary, Chandigarh (IN)

(73) Assignee: COUNCIL OF SCIENTIFIC & INDUSTRIAL RESEARCH, New Delhi (IN)

( * ) Notice: Subject to any disclaimer, the term of this patent is extended or adjusted under 35 U.S.C. 154(b) by 1044 days.

(21) Appl. No.: 17/272,221

(22) PCT Filed: Aug. 28, 2019

(86) PCT No.: PCT/IN2019/050623
§ 371 (c)(1),
(2) Date: Feb. 26, 2021

(87) PCT Pub. No.: WO2020/044371
PCT Pub. Date: Mar. 5, 2020

(65) Prior Publication Data
US 2021/0395728 A1  Dec. 23, 2021

(30) Foreign Application Priority Data

Aug. 29, 2018 (IN) .............................. 201811032280

(51) Int. Cl.
| C12N 15/10 | (2006.01) |
| C12N 15/70 | (2006.01) |
| C12P 19/18 | (2006.01) |
| C12P 19/44 | (2006.01) |

(52) U.S. Cl.
CPC ..... *C12N 15/1058* (2013.01); *C12N 15/1082* (2013.01); *C12N 15/70* (2013.01); *C12P 19/18* (2013.01); *C12P 19/44* (2013.01)

(58) Field of Classification Search
CPC .................. C12N 9/1048; C12N 15/09; C12N 15/1058; C12N 15/1082; C12N 15/63; C12N 15/70; C12P 19/18; C12P 19/44; C12P 19/64
See application file for complete search history.

(56) References Cited

U.S. PATENT DOCUMENTS

| 5,643,758 A | 7/1997 | Guan et al. |
| 2004/0142856 A1 | 7/2004 | DeFrees et al. |
| 2009/0074798 A1 | 3/2009 | Aebi et al. |
| 2016/0177355 A1 | 6/2016 | Fisher et al. |

FOREIGN PATENT DOCUMENTS

| IN | 201611011974 | 3/2017 |
| WO | WO2003074687 A1 | 9/2003 |
| WO | WO2017093291 A1 | 6/2017 |
| WO | WO2017175239 A1 | 10/2017 |

OTHER PUBLICATIONS

J. Zhang, R. L. Gallo, Current biology : CB 26, R14, Jan. 11, 2016.
P. D. Cotter, R. P. Ross, C. Hill, Nat Rev Microbiol 11, 95, Feb. 2013.
G. E. Norris, M. L. Patchett, Current opinion in structural biology 40, 112 (Oct. 2016).
S. Biswas, C. V. Garcia De Gonzalo, L. M. Repka, W. A. van der Donk, ACS chemical biology 12, 2965, Dec. 15, 2017.
J. Stepper et al., Febs Lett 585, 645,Feb. 18, 2011.
Zaid Amso, Sung-Hyun Yang, Paul W. R. Harris, Tom H. Wright, Claudio D. Navo, Mark L. Patchett, Gillian E. Norris and Margaret A. Brimble, Chemical Science, 1686 2018.
H. Hanchi et al., J Agr Food Chem 64, 3584, May 11, 2016.
M. A. Maky et al., Applied and environmental microbiology 81, 4819 (Jul. 2015).
R. Nagar, A. Rao, Glycobiology, May 12, 2017.
A. B. Ingham, K. W. Sproat, M. L. V. Tizard, R. J. Moore, J Appl Microbiol 98, 676, 2005.
G. M. Gibbs, B. E. Davidson, A. J. Hillier, Appl Environ Microb 70, 3292, Jun. 2004.
H. Q. Chen et al., Biotechnol Lett 34, 359, Feb. 2012.
A. A. Ollis, S. Zhang, A. C. Fisher, M. P. DeLisa, Nat Chem Biol 10, 816, Oct. 2014.
H. Ren, S. Biswas, S. Ho, W. A. van der Donk, H. Zhao, ACS chemical biology 13, 2966.
A. Kaunietis, A. Buivydas, D. J. Ãœeitaviä ius, O. P. Kuipers, Nature communications 10, 1115.
B. Janesch et al., Glycobiology 29, 588.
T. G. Keys et al., Metabolic engineering 44, 293, Nov. 2017.
M. L. Chikindas, R. Weeks, D. Drider, V. A. Chistyakov, L. M. Dicks, Current opinion in biotechnology 49, 23, Feb. 2018.
R. Ramu et al., Critical reviews in food science and nutrition, Jul. 20, 2015.
V. Bali, P. S. Panesar, M. B. Bera, J. F. Kennedy, Critical reviews in food science and nutrition 56, 817, 2016.
Z. Benmechernene et al., Recent patents on DNA & gene sequences 7, 66, Apr. 1, 2013.

*Primary Examiner* — Jeremy C Flinders
(74) *Attorney, Agent, or Firm* — Blank Rome LLP

(57) ABSTRACT

The present invention relates to a recombinant microbial system for generation of neo-glycocins, a substrate and to co-evolve its glycosyltransferase enzyme. The recombinant microbial system comprises a gene cassette A encoding for microbial O- and S-glycosyltransferase and its suitable acceptor substrate in conjugation with a cleavable dual affinity tag under the control of two independent inducible promoters. The gene cassette is expressed in a microbial host such as *E. coli* for the co-expression of glycosyltransferase and its suitable acceptor substrate. The invention further discloses method for production and bioactivity guided screening of O- and or S-neo-glycocins using the recombinant microbial system. The system provides optimized construct design, and methods for high yield production of glycocins and neo-glycocins for downstream applications.

16 Claims, 14 Drawing Sheets

Specification includes a Sequence Listing.

| Bacterial Strain and Plasmids | Description/Genotype |
|---|---|
| *E. coli* TOP10 | mcrA, Δ(mrr-hsdRMS-mcrBC), Phi80lacZ(del)M15, ΔlacX74, deoR, recA1, araD139, Δ(ara-leu)7697, galU, galK, rpsL(SmR), endA1, nupG |
| *E. coli* KRX | [F-prime, traD36, -delta-ompP, proA+B+, lacI$^q$, -delta-(lacZ)M15] -delta-ompT, endA1, recA1, gyrA96 (Nalr), thi-1, hsdR17 (r$_k$-, m$_k$+), e14- (McrA-), relA1, supE44, -delta-(lac-proAB), -delta-(rhaBAD)::T7 RNA polymerase. |
| *E. coli* BL21 (DE3) | fhuA2 [lon] ompT gal (λ DE3) [dcm] ΔhsdS  λ DE3 = λ sBamHIo ΔEcoRI-B int::(lacI::PlacUV5::T7 gene1) i21 Δnin5 |
| *E. coli* SHuffle® T7 Express | fhuA2 lacZ::T7 gene1 [lon] ompT ahpC gal λatt::pNEB3-r1-cDsbC (SpecR, lacIq ) ΔtrxB sulA11 R(mcr-73::miniTn10--TetS )2 [dcm] R(zgb-210::Tn10 --TetS ) endA1 Δgor Δ(mcrC-mrr)114::IS10 |
| *E. coli* Lemo21 (DE3) | fhuA2 [lon] ompT gal (λ DE3) [dcm] ΔhsdS/ pLemo(CamR)  λ DE3 = λ sBamHIo ΔEcoRI-B int::(lacI::PlacUV5::T7 gene1) i21 Δnin5  pLemo = pACYC184-PrhaBAD-lysY |
| *E. coli* Rosetta™ (DE3) | F$^-$ ompT hsdS$_B$(r$_B^-$ m$_B^-$) gal dcm (DE3) pRARE (Cam$^R$) |

FIG. 1

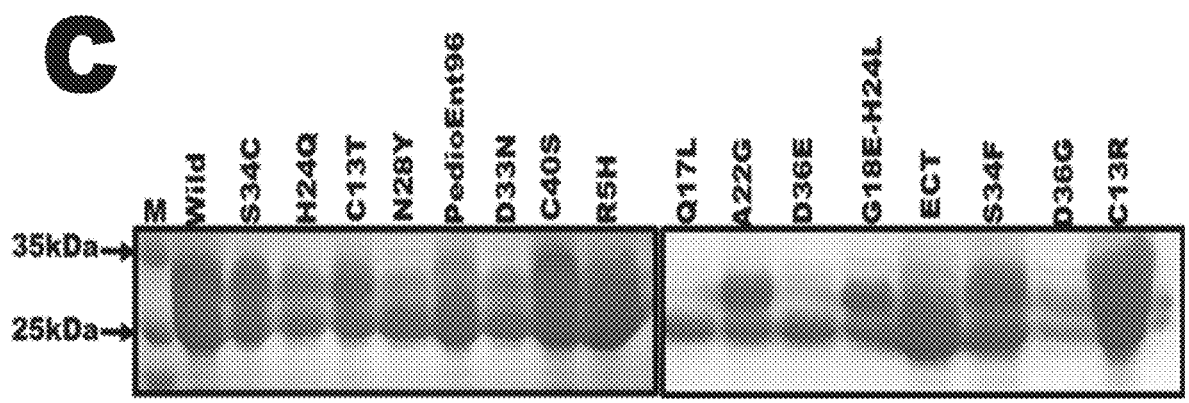
FIG. 5Bc
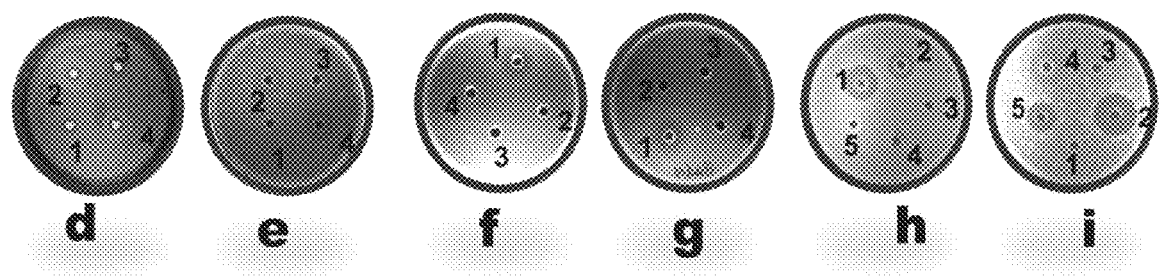
FIG. 5Bd, e, f, g, h, i

RECOMBINANT MICROBIAL SYSTEM FOR DIRECTED EVOLUTION OF GLYCOCINS AND METHOD OF PREPARATION THEREOF

REFERENCE TO RELATED APPLICATIONS

This application is a national phase application of PCT/IN2019/050623, filed Aug. 28, 2019 which claims priority to Indian Application No. 201811032280 filed Aug. 29, 2018. The entire contents of those applications are incorporated herein by reference.

FIELD OF THE INVENTION

The present invention relates to a recombinant microbial system for directed evolution of glycocins, the ribosomally produced and post translationally modified antimicrobial peptides. More particularly, the recombinant microbial system(s) are to co-evolve acceptor substrates to generate O- and/or S-neo-glycocins and or their glycosyltransferase enzymes. The invention also discloses a method for expression and screening of O- and or S-neo-glycocins using the recombinant microbial system(s). Another aspect of the invention discloses method(s) optimized for the production and purification of O- and/or S-glycosylated neo-glycocins using recombinant microbial system(s).

BACKGROUND OF THE INVENTION

Antimicrobial peptides (AMPs) with diverse class of naturally occurring molecules that are produced as a first line of defense by majority of multicellular organisms. AMPs are oligopeptides with number generally varying from five to over hundreds of amino acids. AMPs are a growing class of natural and synthetic peptides with a wide spectrum of targets including viruses, bacteria, fungi, parasites, cytotoxicity on cancer cells etc. AMPs produced by various cell types including microbial cells are a common host defense system.

Cationic AMPs consist of between 10 to 50 amino acid residues with an overall positive charge. These peptides frequently contain a distribution of basic amino acids and hydrophobic residues that align in three dimensions on opposing faces, therefore forming unique structures that are water soluble, positively charged and hydrophobic. Folded AMPs are classified into groups based on their secondary structure such as α-helical, β-sheet as well as extended AMPs, which exhibit little secondary structure in aqueous solution but adopt the amphipathic α-helical architecture when they enter a non-polar environment such as the bacterial membrane (1).

The available antibiotics are associated with multi-resistance. In view of rising threats of multi-resistant bacteria, AMPs including bacteriocins are promising as a valuable alternate to antibiotics or as a combination therapy with known antibiotics. Owing to their peptide nature, bacteriocins are more amenable to engineering or directed evolution than classical antibiotics which can be accomplished by gene manipulation in host, in vivo or chemical synthesis of the same. Bioengineered peptides often exhibit enhanced functionalities (activity and/or stability) hence attractive from an application perspective. For example, in vitro bioengineered derivatives of the lantibiotics nisin, actagardine and nukacin ISK-1, as well as derivatives of lacticin 481 have enhanced specific activity against target bacteria. Similarly, engineered variants of lactocin S are more stable than their natural counterpart. In the case of thiopeptides (S-linked), semi-synthetic derivatives have been generated that have increased water solubility, including several nocathiacin derivatives and GE2270A (2)

Some of these AMPs or bacteriocins undergo unusual posttranslational modifications (PTMs) such as glycosylation and disulfide bonding. Bacteriocins that are characterized by two or more β-sheets are often stabilized by disulfide bonds. Glycosylation is in fact one of the most prevalent post-translational modifications of protein with a defining impact on their structure and function. Many of the proteins involved in the innate or adaptive immune response including cytokines, chemokines and secretory proteins are glycosylated thus contributing to their activities. Glycosylation imparts a variety of biological functions and greater proteomic dissimilarities than other PTMs.

Recently discovered class of ribosomally synthesized and post-translationally modified peptides produced in bacteria are known as glycosylated antimicrobial peptides or glycocins or glycosylated bacteriocins. In bacteria, such glycocins are characterized and are known to exhibit moderate toxicity, good stability under high temperature and wide range of pH and activity against a variety of bacteria including drug resistant bacteria such as Methicillin Resistant *Staphylococcus aureus* (MRSA), gentamicin-resistant *Enterococcus faecalis* (*E. faecalis*) and *Listeria monocytogenes* (*L. monocytogenes*) etc. For the fact that each of these glycocins have a defined inhibitory spectrum strongly implies that they recognize specific receptors on target cells. Hence, glycocins are hypothesized to act via receptor mediated mode. The glycocins possess a carbohydrate group termed glycan, which is attached covalently to a peptide backbone. The most common patterns of glycosylation observed in glycosylated antimicrobial peptides are linkage through the hydroxyl group of serine or threonine residues i.e. 0-linked or rarely through a sulfur atom of a cysteine residue i.e. S-linked. The S-linkage in these antimicrobial peptides confers bioactivity, self-immunity and enhance the antimicrobial activity of the peptide (3-9).

The current availability of synthetic coupling and glycoengineering technology makes it possible to customize the most beneficial glycan modifications for improved stability, microbicidal potency, pathogen specificity, tissue or cell targeting and immunomodulation.

Heterologous or recombinant expression systems have been tried in the past mainly for the (a) expression and production of AMPs to obtain higher-yields of AMPs; or (b) live delivery of AMPs, in vivo. While unmodified bacteriocins with restricted antimicrobial activity, for example the class IIa bacteriocins are easy to adapt for such systems (10-12), the modified ones, such as the lantibiotics, circularized bacteriocins and glycocins (glycosylated AMP) are hard to adapt as not only the structural gene, but all the genes capable of performing the modifications must be expressed in the heterologous host. Components like secretory machinery and immunity proteins add more complexity in such heterologous expression. With broad-spectrum AMPs in bacterial systems, there are further more difficulties as active AMPs would kill the host. The approach used for expression of broad spectrum AMPs is to produce them as bioinactive fusion protein wherein bio-activity is recovered by specific cleavage of AMPs from fusion protein.

The US publication No. US20090074798A1 entitled "System and method for the production of recombinant glycosylated proteins in a prokaryotic host" discloses a system and method for the production of recombinant N-glycosylated target proteins. The system comprises a prokaryotic organism such as *E. coli* into which genetic information encoding for a metabolic apparatus capable of carrying out the requested N-glycosylation of the target protein is introduced. The system also contains the genetic information required for the expression of one or more recombinant target proteins. The metabolic apparatus preferably comprises specific glycosyltransferases for the assembly of the oligosaccharide on a lipid carrier and an OTase that covalently links this oligosaccharide to specific residues of the desired protein. However, the prokaryotic system fails to co-evolve the enzyme and the substrate.

The U.S. Pat. No. 5,643,758A entitled "Production and purification of a protein fused to a binding protein" describes method for producing and purifying a hybrid polypeptide molecule employing recombinant DNA techniques. More specifically, a DNA fragment coding for a protein molecule such as a polypeptide is fused to a DNA fragment coding for a binding protein such as the gene coding for the maltose binding protein. The fused DNA is inserted into a cloning vector and into an appropriate host. Upon expression, a hybrid polypeptide is produced which is purified by contacting the hybrid polypeptide with a ligand or substrate to which the binding protein has specific affinity, e.g. by affinity chromatography. The hybrid polypeptide so purified is useful in its hybrid form or it may be cleaved to obtain the protein molecule itself by linking the DNA fragments coding for the target and binding proteins with a DNA segment, which codes for a peptide that is recognized and cleaved by Factor Xa. However, the invention lacks appropriate bioactivity guided screening system for the antimicrobial peptides.

The PCT publication No. WO2017175239A1 entitled "A multifunctional recombinant nucleotide dependent glycosyltransferase protein and its method of glycosylation thereof" discloses a method of peptides or polypeptides modification by glycosylation. In particular, the invention relates to one pot synthesis of disaccharide glycan on to the acceptor substrate and thereby generating O- and/or S-glycosylated neo-glycopeptides including antimicrobial peptides by using multifunctional recombinant nucleotide dependent glycosyltransferase. However, the invention fails to explain the simultaneous expression and co-evolution of the glycosyltransferase enzyme and its substrate.

The US publication No. US20040142856A1 entitled "Glycoconjugation methods and proteins/peptides produced by the methods" discloses the methods and compositions for remodeling a peptide molecule including the addition or deletion of one or more glycosyl groups to a peptide and also the addition of a modifying group to a peptide forming a covalent conjugate between a polymer and a glycosylated or non-glycosylated peptide, wherein the polymer is conjugated to the peptide via an intact glycosyl linking group interposed between and covalently linked to both the peptide and the polymer. The invention also discloses a method that comprises contacting the peptide with a mixture comprising a nucleotide sugar covalently linked to the polymer and a glycosyltransferase for which the nucleotide sugar is a substrate under conditions sufficient to form the conjugate. However, the method is not amenable for large library generation or for bioactivity guided library screening.

The PCT publication No. WO2017093291A1 titled "Methods of producing glycosylated proteins" discloses methods of producing N-glycosylated proteins in vitro and in vivo. The methods include using host cells to produce glycosylated proteins. The methods further describe co-expression of Polysialyltransferases (PolyST) in host to obtain sialylated product. However, the system is not applicable to O and S-glycosylated product.

The NCBI article, numbered PMID:29112373 titled "Structure-Activity Relationships of the S-Linked Glycocin Sublancin" (4) discloses the heterologous expression of genes namely sunA and sunS (components of sublancin biosynthesis pathway of *Bacillus subtilis* 168 (*B. subtilis* 168)) encoding full-length sublancin (a glycocin) with intact leader sequence and its glycosyltranfearse SunS in *E. coli*. The system produces mono-glycosylated full-length peptide with intact leader sequence; however, the yield of the peptide is poor, choice of host strain is constrained to disulfide forming strains only and a multistep downstream processing is required to obtain a mono-glycosylated bioactive sublancin that may include oxidative refolding. Accordingly, the system is not suitable for directed evolution of glycocin and upscaling the production of glycocin.

The NCBI article, numbered PMID: 25129029 titled "Engineered oligosaccharyltransferases with greatly relaxed acceptor-site specificity" describes heterologous transfer of bacterial oligosaccharyl transferase in *E. coli* and an assay to mutate the enzyme and to screen for relaxed specificity variants. However, the method is limited to acceptor specificity of the said oligosaccharyltrasnferase and not extendable to glycocin production and directed evolution thereof (13).

The NCBI article, numbered PMID: 30183259 titled "Rapid Discovery of Glycocins through Pathway Refactoring in *Escherichia coli*" describes a synthetic biology approach based on the pathway refactoring strategy developed for discovery of new glycocins. Using RODEO (Rapid ORF Description and Evaluation Online) based, a genome mining tool for RiPPs, and two rounds of plug-and-play pathway refactoring four new glycocins, namely bacillicin CER074, bacillicin BAG2O, geocillicin, and listeriocytocin, respectively are successfully expressed in heterologous host *E. coli* BL21 (DE3). While the Enterocin 96 study describes heterologous expression of these glycocins in *E. coli*, the said heterologous system is neither suitable for directed evolution of glycocins nor for up scaling the production of glycocins (14).

The NCBI article, numbered PMID: 30846700 titled "Heterologous biosynthesis and characterization of a glycocin from a thermophilic bacterium" describes an in vivo heterologous expression system to produce a mature glycocin belonging to thermophilic bacterium, *Aeribacillus pallidus* in *E. coli* BL21 (DE3). However, this system is also not suitable for directed evolution of glycocin and upscaling the production of glycocin(15).

The NCBI article, numbered PMID: 30976781 titled "Directed evolution of bacterial polysialyltransferases" described the development of a FACS based high throughput screen for the detection of polyST activity based on the complementation of a polyST knockout in the *E. coli* strain EV36_NeuSKO, and a secondary screen to verify that the FACS based screen had enriched mutants with improved activity and or stability and to screen for mutants with specific improvements, e.g., thermal stability. However this screening methodology is limited to only bacterial polySTs and not applicable to glycocin production and directed evolution thereof (16).

In view of the general challenges associated with applications of the AMP's like potential cytotoxicity, sensitivities, specificities, high production costs, folding issues and also the lack of understanding of their structure-function relationship, a facile method to generate libraries of bioactive O- and S-glycosylated peptides or neo-glycoactive peptides i.e. the peptides where glycan is essential for bioactivity are of great value. Further, AMPs are protein in nature and are more compatible for in vitro or laboratory evolution by means of library generation by chemical synthesis or by using recombinant expression systems.

Methods available for expression of glycopeptides and neo-glycopeptide employ either chemical synthesis or in vitro enzymatic synthesis (12) that are not cost-effective, results in less yield, slow, not suitable for large library generation or for bioactivity guided library screening. Further, such expression systems and methods have more than one dimension of variations including sequence, length and glycan of the peptide that are not comprehensively addressed by existing methods known in the art. Most existing methods are associated with expression of either only enzyme or only antimicrobial peptide hence there is a requirement of co-evolution of a glycosyltransferase along with its substrate to provide superior libraries for novel antimicrobial peptides and glycocins. Further, the existing methods lack the appropriate system to generate libraries of glycocins, appropriate bioactivity guided screening system for such glycocins and expression of neo-glycocins to obtain higher yields.

OBJECTIVE OF THE INVENTION

An objective of the present invention is to provide a recombinant microbial system for synthesis of neo-glycocins, comprising (a) cloning vector pRSFDuet-1SapI; (b) gene cassette A comprising a DNA sequence encoding glycosyltransferase, and a DNA sequence encoding an acceptor sequence; and (c) a host cell.

Another objective of the present invention is to provide a recombinant microbial system comprising (i) a cloning vector pRSFDuet-1SapI comprising a gene cassette A having a DNA sequence encoding glycosyltransferase, and a DNA sequence encoding an acceptor sequence; (ii) an additional vector comprising a gene cassette B having a DNA sequence encoding an acceptor sequence; and (iii) a host cell.

Yet another objective of the present invention is to provide a method for construction of the recombinant microbial system comprising (a) cloning vector pRSF Duet-1SapI; (b) gene cassette A comprising a DNA sequence encoding glycosyltransferase, and a DNA sequence encoding an acceptor sequence; and (c) a host cell.

Yet another objective of the present invention is to provide a method for synthesis of neo-glycocins using the recombinant microbial system comprising (a) cloning vector pRSF Duet-1SapI; (b) gene cassette A comprising a DNA sequence encoding glycosyltransferase, and a DNA sequence encoding an acceptor sequence; and (c) a host cell.

Still another objective of the present invention is to provide a recombinant microbial system comprising (i) a cloning vector pRSF Duet-1SapI comprising a gene cassette A having a DNA sequence encoding glycosyltransferase, and a DNA sequence encoding an acceptor sequence; (ii) an additional vector comprising a gene cassette B having a DNA sequence encoding an acceptor sequence; and (iii) a host cell.

Another objective of the present invention is to provide a method for enhancing the expression and purification of neo-glycocin using the recombinant microbial system by means of co-transformation of gene cassette A and gene cassette B.

SUMMARY OF THE INVENTION

In an embodiment, the present invention relates to a recombinant microbial system for synthesis of neo-glycocins, wherein the recombinant microbial system comprises: (a) a cloning vector pRSF Duet-1SapI having the nucleotide sequence as set forth in SEQ ID NO: 68; (b) a gene cassette A comprising a DNA sequence encoding glycosyltransferase, and a DNA sequence encoding an acceptor sequence; and (c) a host cell.

Another aspect of the present invention provides a recombinant microbial system, wherein the recombinant microbial system further comprises: (i) a cloning vector pRSF Duet-1SapI comprising a gene cassette A having a DNA sequence encoding glycosyltransferase, and a DNA sequence encoding an acceptor sequence; (ii) an additional vector comprising a gene cassette B having a DNA sequence encoding an acceptor sequence; and (iii) a host cell.

Yet another aspect of the present invention provides a recombinant microbial system, wherein the recombinant microbial system further comprises: (i) a cloning vector pRSF Duet-1SapI comprising a gene cassette A having a DNA sequence encoding glycosyltransferase, and a DNA sequence encoding an acceptor sequence; (ii) an additional vector comprising a gene cassette B having a DNA sequence encoding an acceptor sequence; and (iii) a host cell, wherein the additional vector is selected from the group consisting of pRSFDuet-1 having polynucleotide sequence as set forth in SEQ ID NO: 66, pRSF Duet-1SapI having polynucleotide sequence as set forth in SEQ ID NO: 68 and pTXB1 having polynucleotide sequence as set forth in SEQ ID NO: 67.

Still another aspect of the present invention provides a recombinant microbial system, wherein the acceptor sequence is tagged with dual affinity cleavable tags to provide an acceptor substrate fusion protein AS1 having the amino acid sequence as set forth in SEQ ID NO: 6, AS2 having the amino acid sequence as set forth in SEQ ID NO: 7, or AS3 having the amino acid sequence as set forth in SEQ ID NO: 8.

Another aspect of the present invention provides a recombinant microbial system, wherein the gene cassette A is having a polynucleotide sequence as set forth in sequence selected from the group consisting of SEQ ID NO: 1, SEQ ID NO: 2, SEQ ID NO: 3, SEQ ID NO: 4 and SEQ ID NO: 5.

Yet another aspect of the present invention provides a recombinant microbial system, wherein the acceptor sequence is selected from the group consisting of a polypeptide, a peptide, an antimicrobial peptide, a bacteriocin and a glycocin.

Still another aspect of the present invention provides a recombinant microbial system, wherein the host cell is *E. coli*.

Yet another aspect of the present invention provides a recombinant microbial system, wherein the host cell is *E. coli* KRX.

Another aspect of the present invention provides a recombinant microbial system, wherein the gene cassette A encodes for glycosyltransferase of GT2 family and its acceptor substrate.

An aspect of the present invention provides a method for construction of the recombinant microbial system comprising the steps of: (a) mutating the nucleotide sequence of a pRSFDuet-1vector by site directed mutagenesis using a primer having sequence as set forth in SEQ ID NO: 12 to obtain a vector 1; (b) amplifying and sub cloning a polynucleotide sequence having the sequence selected from the group consisting of SEQ ID NO: 63, SEQ ID NO: 64 and SEQ ID NO: 65 encoding a glycosyltransferase using primers in the vector 1 of step (a) to obtain a vector 2; (c) amplifying and sub cloning an acceptor substrate gene having a polynucleotide sequence selected from the group consisting of SEQ ID NO: 60, SEQ ID NO: 61 and SEQ ID NO: 62 using primers in the vector 2 of step (b) to obtain a vector 3; (d) amplifying and subcloning a nucleotide sequence encoding a fusion tag MC from a vector 4 using primers in the vector 3 of step (c) to obtain a vector 5; (e) extending the fusion tag MC in the vector 5 of step (d) using primers to obtain a vector 6; (f) amplifying and sub cloning an acceptor substrate gene having a polynucleotide sequence selected from the group consisting of SEQ ID NO: 60, SEQ ID NO: 61 and SEQ ID NO: 62 using primers in NcoI and SapI sites of the vector 6 of step (e) to generate a vector comprising a gene cassette A; and (g) transforming the vector comprising the gene cassette A of step (f) in an *E. coli* to obtain the recombinant microbial system.

Another aspect of the present invention provides a method for construction of the recombinant microbial system, wherein the vector 1 is pRSFDuet-1SapI vector.

Yet another aspect of the present invention provides a method for construction of the recombinant microbial system, wherein the vector 2 is selected from the group consisting of EntSpRSFDuet-1SapI, SunSpRSFDuet-1SapI and GccApRSFDuet-1SapI vector.

Still another aspect of the present invention provides a method for construction of the recombinant microbial system, wherein the vector 3 is selected from the group consisting of EntSAS1pRSFDuet-1SapI, EntSAS2pRSFDuet-1Sap1, EntSAS3pRSFDuet-1Sap1, SunSSAS2pRSFDuet-1Sap1 and GccAAS3pRSFDuet-1Sap1vector.

Another aspect of the present invention provides a method for construction of the recombinant microbial system, wherein the vector 4 is selected from the group consisting of pTWIN1, pTXB1 and pTXB3.Yet another aspect of the present invention provides a method for construction of the recombinant microbial system, wherein the vector 5 is selected from the group consisting of EntSAS1MCpRSFDuet-1SapI, EntSAS2MCpRSFDuet-1Sap1, EntSAS3MCpRSFDuet-1Sap1, SunSSAS2MCpRSFDuet-1Sap1 and GccAAS3MCpRSFDuet-1Sap1.

Yet another aspect of the present invention provides a method for construction of the recombinant microbial system, wherein the vector 6 is selected from the group consisting of EntSAS1MCHpRSFDuet-1SapI, EntSAS2MCHpRSFDuet-1Sap1, EntSAS3MCHpRSFDuet-1Sap1, SunSSAS2MCHpRSFDuet-1Sap1 and GccAAS3MCHpRSFDuet-1Sap1.

Still another aspect of the present invention provides a method for construction of the recombinant microbial system, wherein the primers for amplification and sub cloning are having sequences selected from the group consisting of SEQ ID NO: 13, SEQ ID NO:14, SEQ ID NO:15, SEQ ID NO:16, SEQ ID NO:17, SEQ ID NO:18, SEQ ID NO:19, SEQ ID NO:20, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:34, SEQ ID NO:35, SEQ ID NO:36, SEQ ID NO:37, SEQ ID NO:38 and SEQ ID NO:39.

Yet another aspect of the present invention provides a method for construction of the recombinant microbial system, wherein the gene cassette A is having a polynucleotide sequence as set forth in sequence selected from the group consisting of SEQ ID NO: 1, SEQ ID NO: 2, SEQ ID NO: 3, SEQ ID NO: 4 and SEQ ID NO: 5.

An aspect of the present invention provides a method for synthesis of neo-glycocins using the recombinant microbial system, said method comprising: (i) mutating the gene cassette A using a method selected from random mutagenesis or site directed mutagenesis to obtain mutated gene cassette A; (ii) expressing the mutated gene cassette A of step (i) in an *E. coli* to obtain a fusion protein; (iii) purifying and cleaving tag from the fusion protein of step (ii) to obtain a cleaved peptide; (iv) screening the cleaved peptide of step (iii) for an antimicrobial activity using agar diffusion test (ADT) against an indicator bacterial strain to obtain the neo-glycocin.

Still another aspect of the present invention provides a method for synthesis of neo-glycocins using the recombinant microbial system, wherein the neo-glycocin obtained is having the amino acid sequence as set for in sequences selected from the group consisting of SEQ ID NO: 10, SEQ ID NO: 11, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, and SEQ ID NO: 59.

Yet another aspect of the present invention provides a method for synthesis of neo-glycocins using the recombinant microbial system, wherein the indicator bacterial strain is selected from the group consisting of *L. monocytogenes. Vibrio cholera* MTCC 3904, *Listeria monocytogenes* MTCC 839, *E. coli* MTCC 1610, *Bacillus halodurans* MTCC 7181 and *Bacillus licheniformis* MTCC9857.

Another aspect of the present application provides a method for enhancing the expression and purification of neo-glycocin using the recombinant microbial system by means of co-transformation of gene cassette A and gene cassette B.

BRIEF DESCRIPTION OF THE DRAWINGS

The foregoing and other features of embodiments will become more apparent from the following detailed description of embodiments when read in conjunction with the accompanying drawings.

TABLE 1: List of bacterial strain and plasmids.

TABLE 2: List of variants/mutants generated using the microbial system of the invention.

FIG. 1: Tabulates the genotype of the bacterial strain used in the construction and expression of the recombinant vector systems.

Figure 2A:
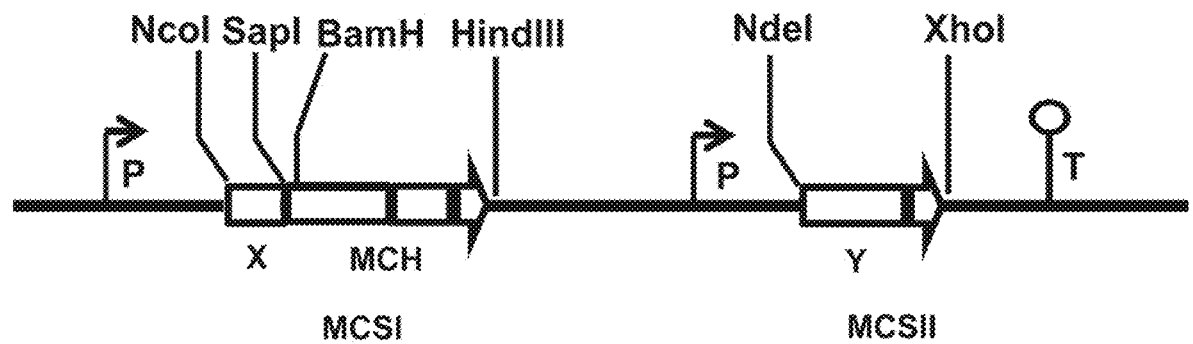
Figure 2B:
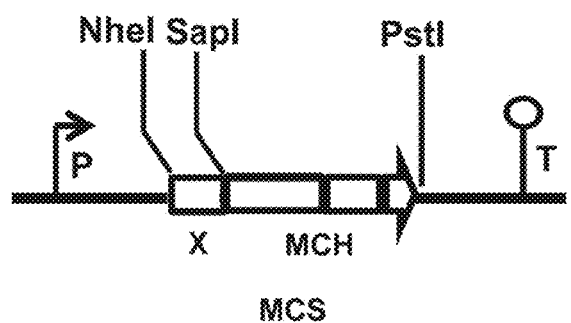

FIG. 2: Illustrates the design of the recombinant expression cassette of the recombinant microbial systems of the invention; FIG. 2A illustrates construct A; FIG. 2B illustrates construct B.

Figure 3A:
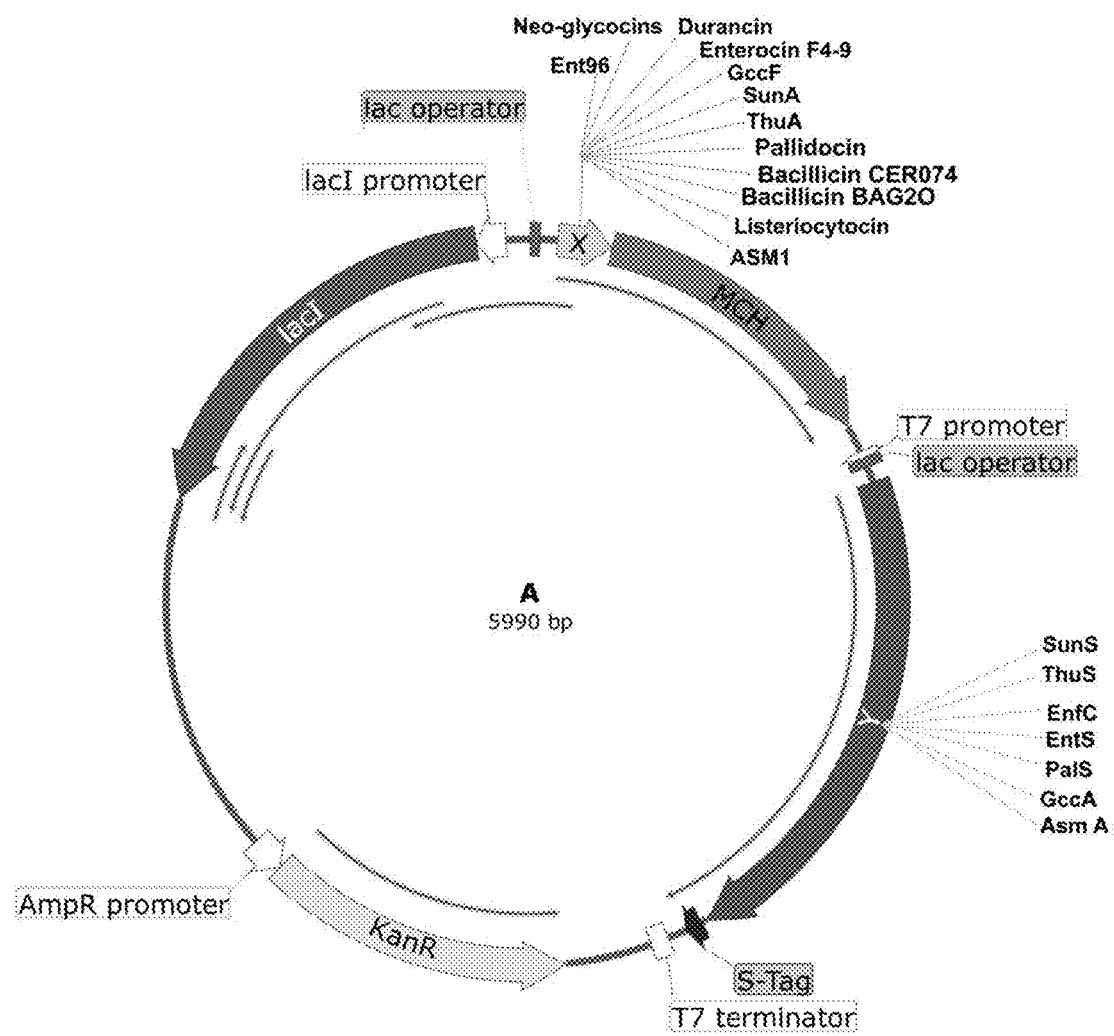
Figure 3B:
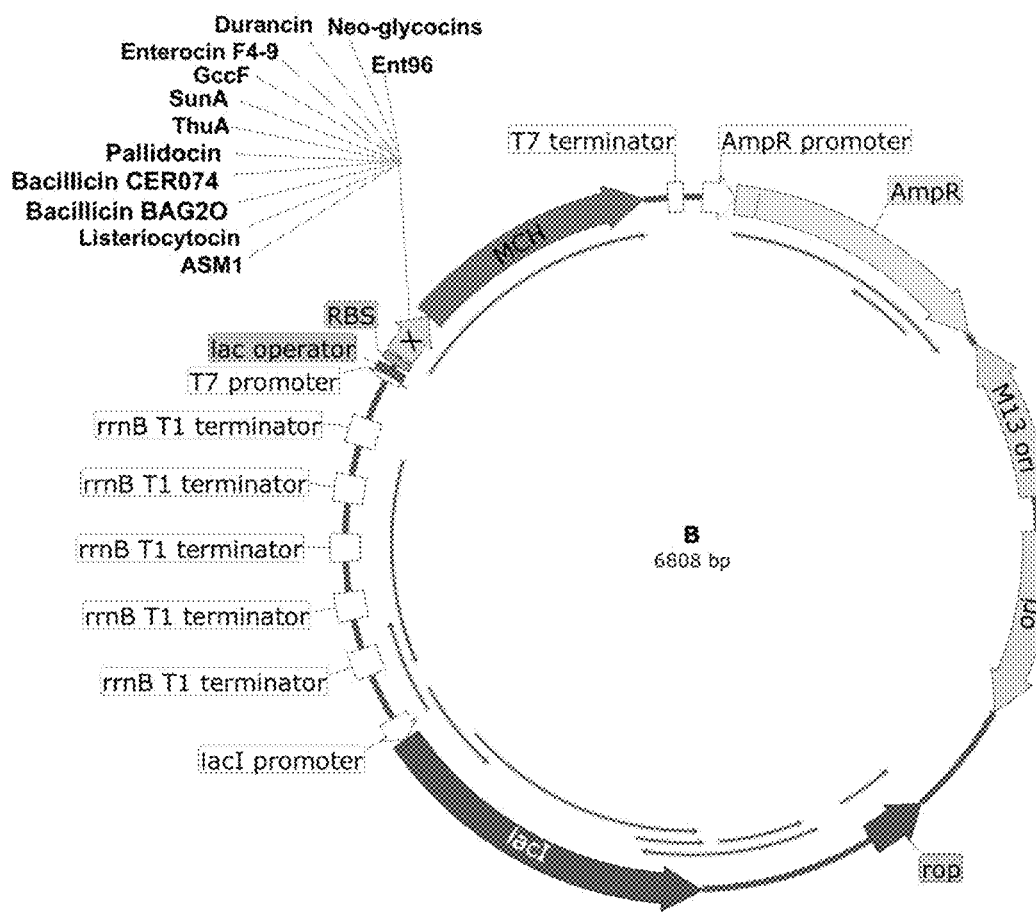

FIG. 3: Illustrates the design of the recombinant expression vector harboring construct A and construct B of the recombinant microbial systems of the invention. FIG. 3A illustrates the vector map of recombinant expression vector A harboring construct A. FIG. 3B illustrates the vector map of the recombinant expression vector B harboring construct B.

Figure 4A:
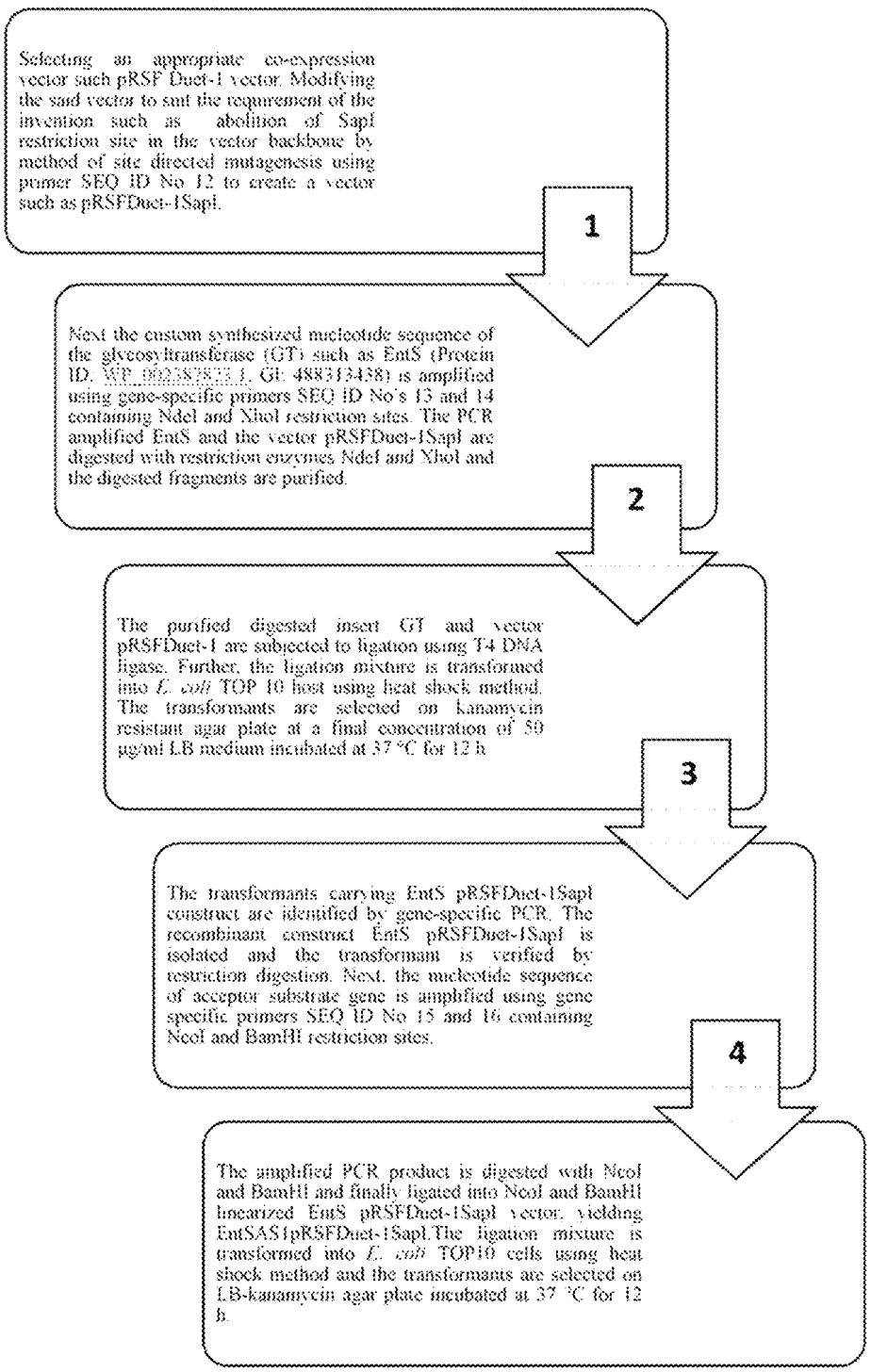

FIG. 4A: Illustrates the method of construction of recombinant microbial system of the invention and the method of bioactivity guided high throughput screening for neo-glycocins using recombinant microbial system of the invention.

Figure 4B:
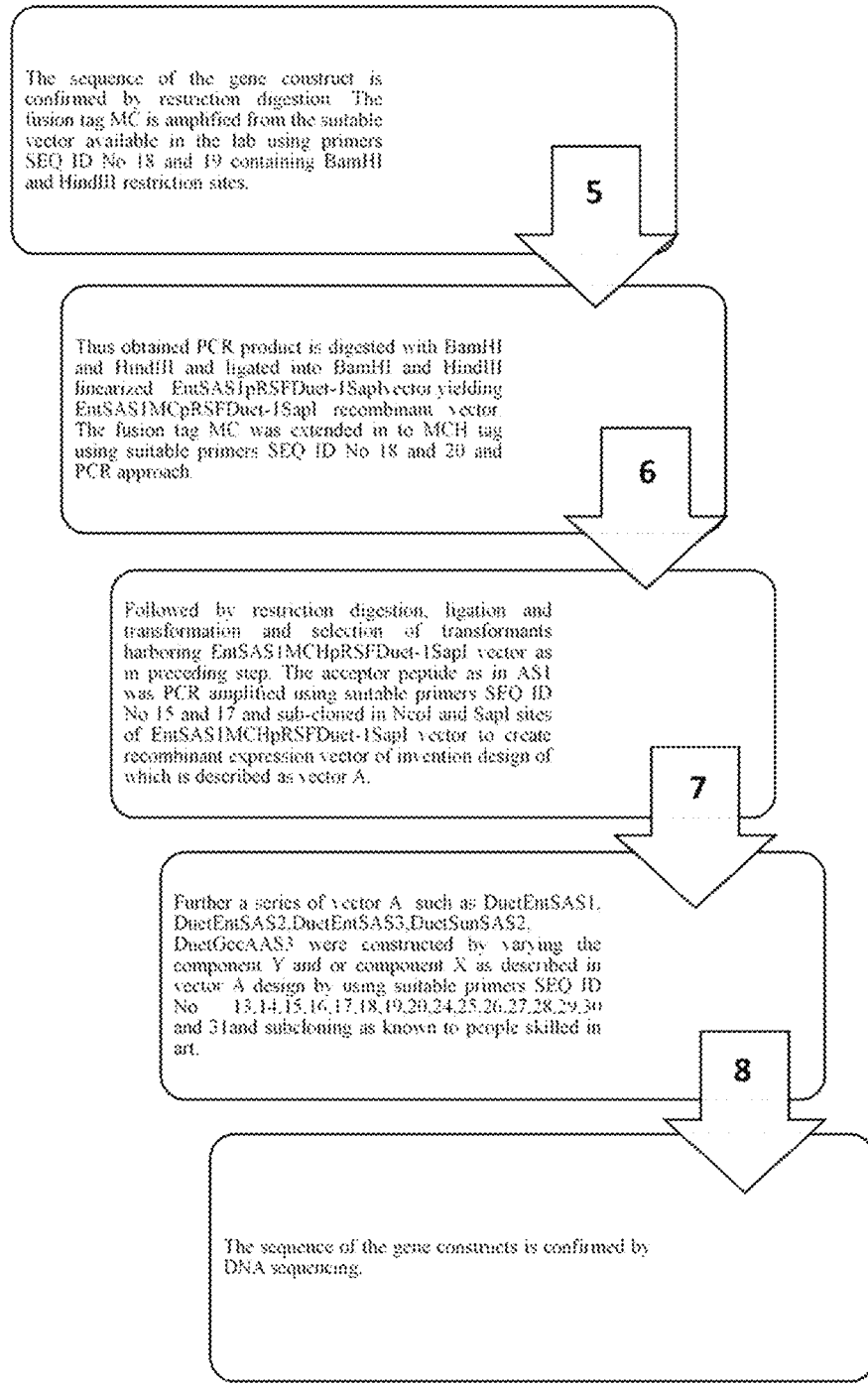

FIG. 4B: Illustrates the method of construction of recombinant microbial system of the invention.

Figure 4C:
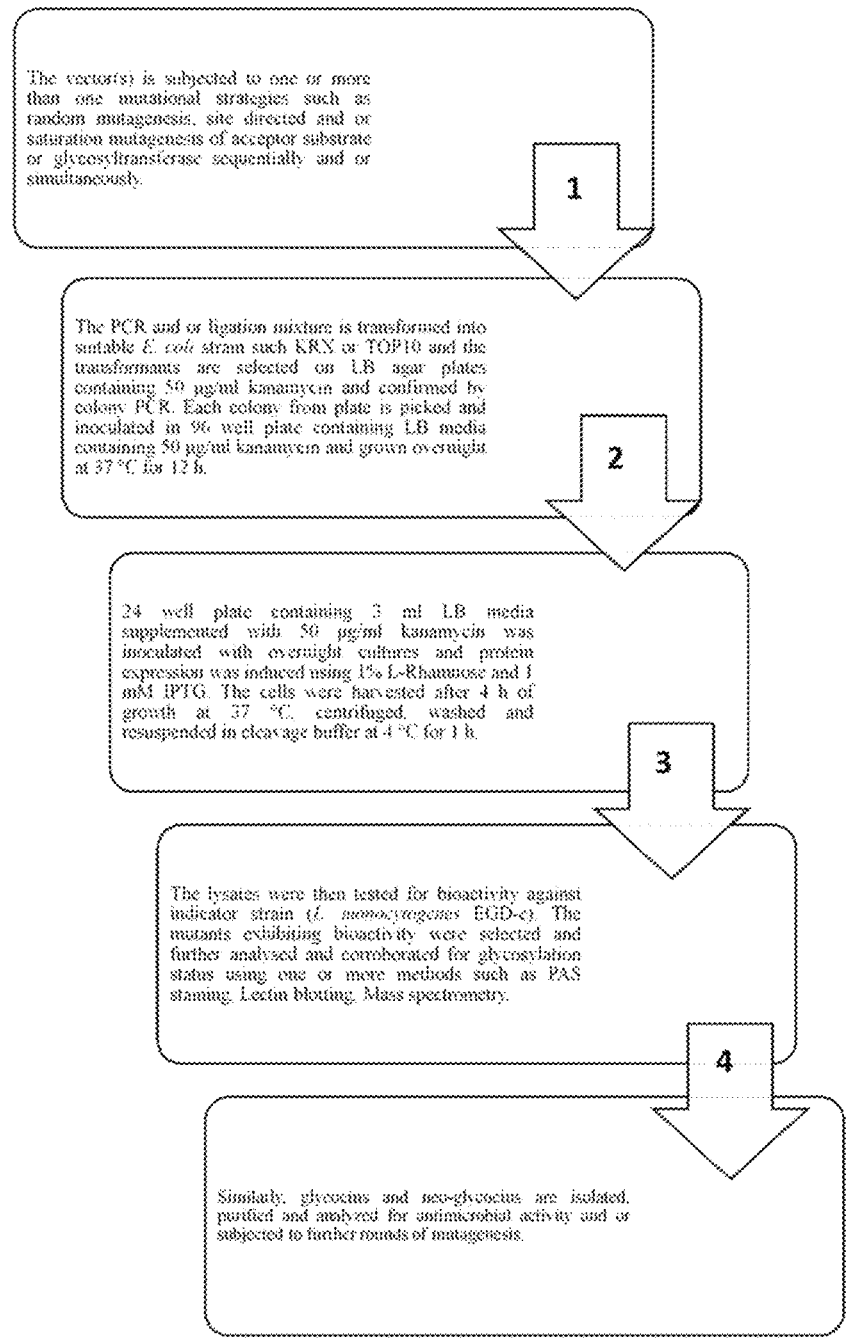

FIG. 4C: Illustrates the method of bioactivity guided high throughput screening for in vivo modified neo-glycocins using recombinant microbial system of the invention.

Figure 5A:
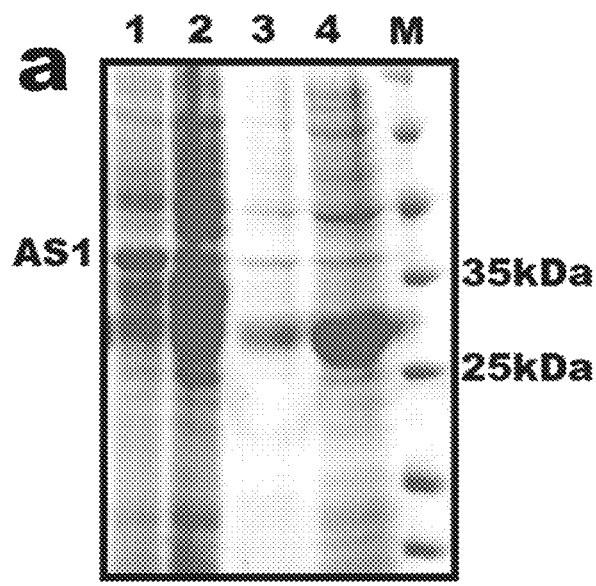
Figure 5A:
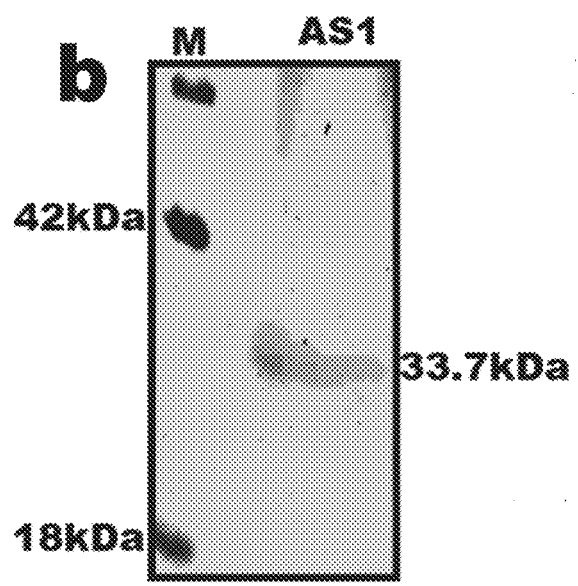
Figure 5A:
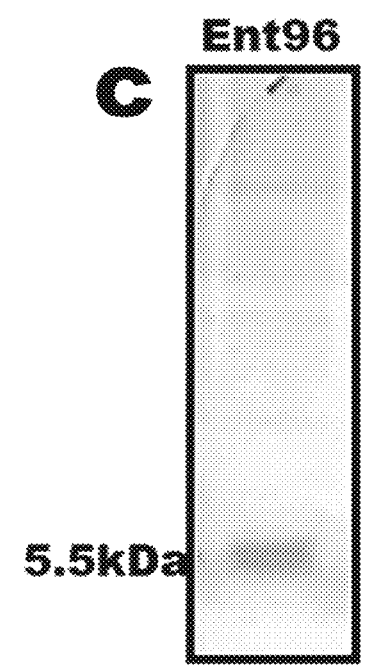
Figure 5A:
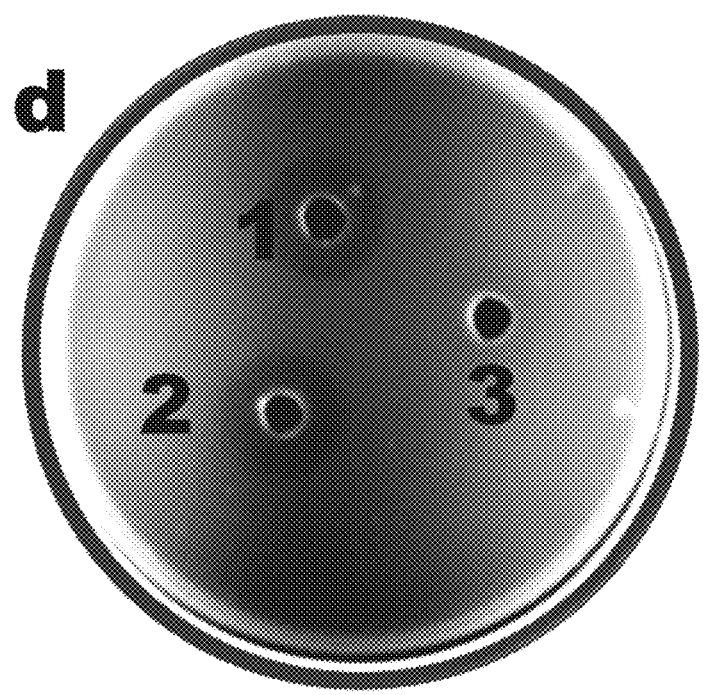
Figure 5A:
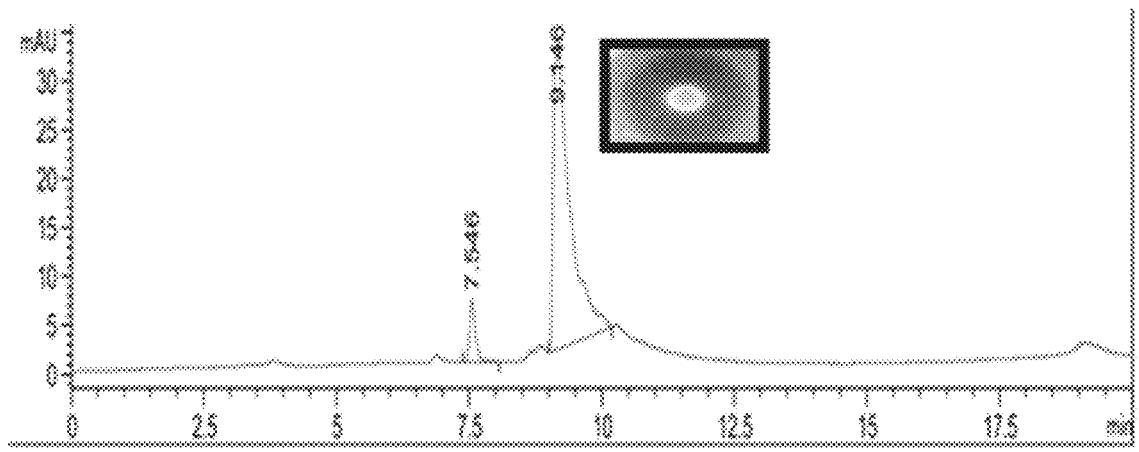
Figure 5A:
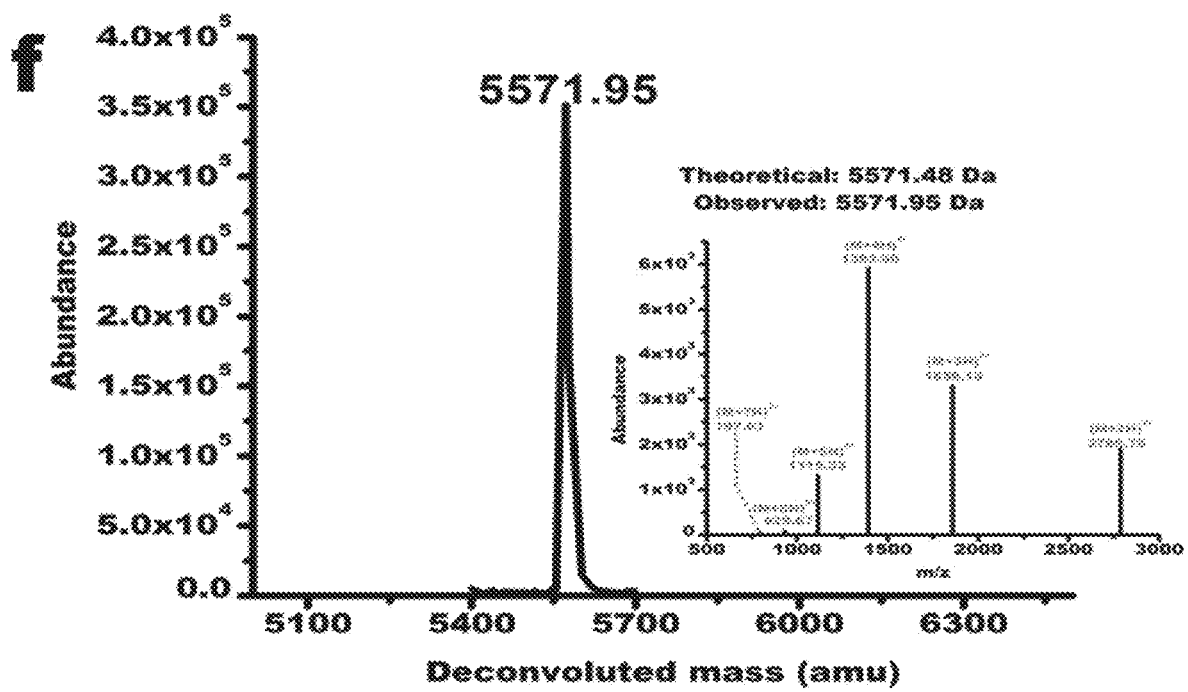

FIG. 5A: Illustrates the expression, purification and anti-listerial activity of diglycosylated Enterocin 96 and neo-glycocins, produced using the recombinant microbial system of the invention.

FIG. 5Aa 12.5% SDS-PAGE profile of MCH tagged AS1 (33.7 KDa) pellet and supernatant fractions, respectively (Lane 1 and 2), 12.5% SDS-PAGE profile of MCH tagged AS1 pellet and supernatant fractions treated with cleavage buffer (28. 2 KDa) resulting in to release of glycocin Enterocin 96 in solution (5.5 KDa), respectively (Lane 3 and 4);

FIG. 5Ab: Confirmation of glycosylation of MCH tagged AS1 (33.7 KDa);

FIG. 5Ac: Confirmation of cleavage buffer treated glycocin Enterocin 96 released in solution using PAS staining (5. 5 KDa) Enterocin 96;

FIG. 5Ad: Anti-listerial activity of Enterocin 96 using ADT assay, where 1: Enterocin 96 produced using the microbial system of the present invention, 2: Positive control (custom synthesized diglucosylated Enterocin 96), 3: Negative control (cleavage buffer);

FIG. 5Ae: HPLC purification profile of Enterocin 96 with inset showing bioactivity of purified Enterocin 96 against *L. monocytogenes*.

FIG. 5Af: Deconvoluted spectra of LC-ESI-MS of Enterocin 96 confirming molecular weight of diglucosylated Enterocin 96 as 5572 Da. Multiple charged ions are shown in inset.

Figure 5B:
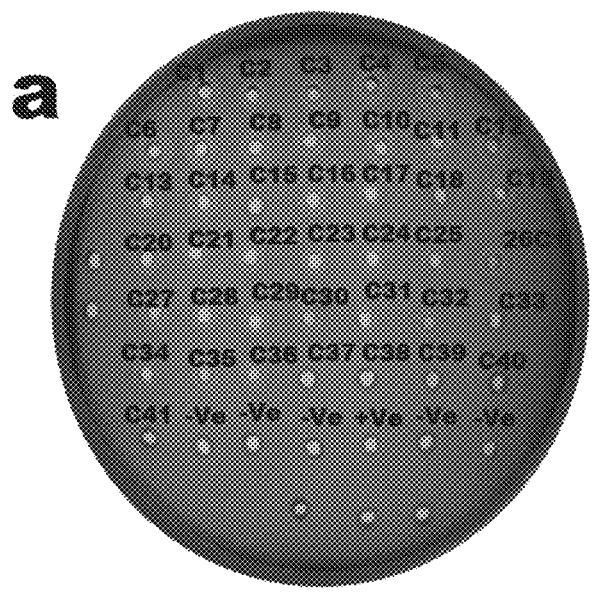
Figure 5B:
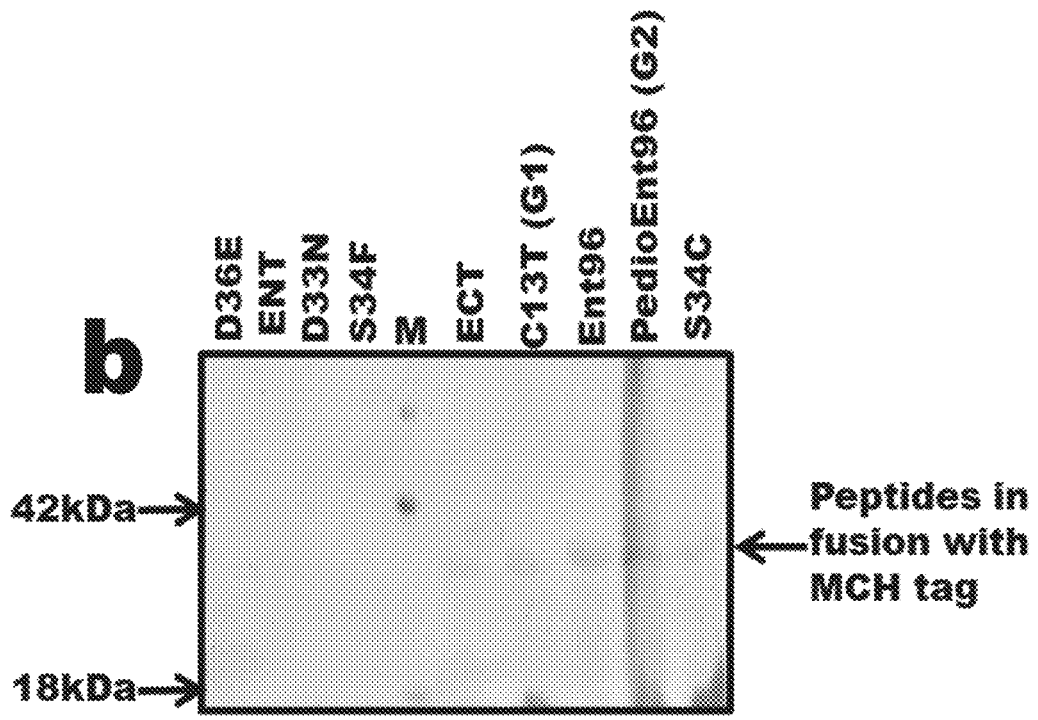

FIG. 5B: Illustrates the characterization of the variants of Enterocin 96 now termed as Enterocin 96 neo-glycocins generated using the microbial system of invention.

FIG. 5Ba: Screening of library of Enterocin 96 O- and S-linked neo-glycocins (corresponding bacterial colonies C1-C41) against indicator strain *L. monocytogenes* EGDe using ADT;

FIG. 5Bb: Confirmation of the glycosylation status of selected uncleaved neo-glycocins using PAS staining Enterocin 96;

FIG. 5Bc: Enterocin 96 Purification of selected uncleaved neo-glycocins using affinity chromatography;

FIG. 5B (d-i): Confirmation of antimicrobial activity of cleaved neo glycocins against bacterial strains namely *L. monocytogenes* EGDe (FIG. 5Bd-e): *Vibrio cholera* MTCC 3904 (FIG. 5Bf), *E. coli* 1610 (FIG. 5Bg), *Bacillus* lichenmformis MTCC 9857 (FIG. 5Bh) and *Bacillus halodurans* MTCC 7181 (FIG. 5Bi) using ADT;

wherein #1, d and e: negative control/lysis buffer; #2, d and e: positive control cell lysate of cleavage buffer treated parent peptide Enterocin 96 diglycosylated having SEQ ID NO: 9; #3, d and e is negative control/cleavage buffer; #4, d and e is cell lysate of cleavage buffer treated S34C, a chemovariant of Enterocin 96 having SEQ ID NO: 40;

Where in #1, f and g: cell lysate of cleavage buffer treated C13T, a variant of Enterocin 96 having SEQ ID NO: 10; #2, f and g: positive control parent peptide Enterocin 96 diglycosylated having SEQ ID NO: 9; #3, f and g: negative control/lysis buffer; #4.f and g: is negative control/cleavage buffer;

Wherein #1, h and i: cell lysate of cleavage buffer treated C13T, a variant of Enterocin 96 having SEQ ID NO: 10; #2, h and i: positive control parent peptide Enterocin 96 diglycosylated having SEQ ID NO: 9; #3, h and i: negative control/cleavage buffer; #4, h and i: is nisin (1 mg/ml).

Figure 6A:
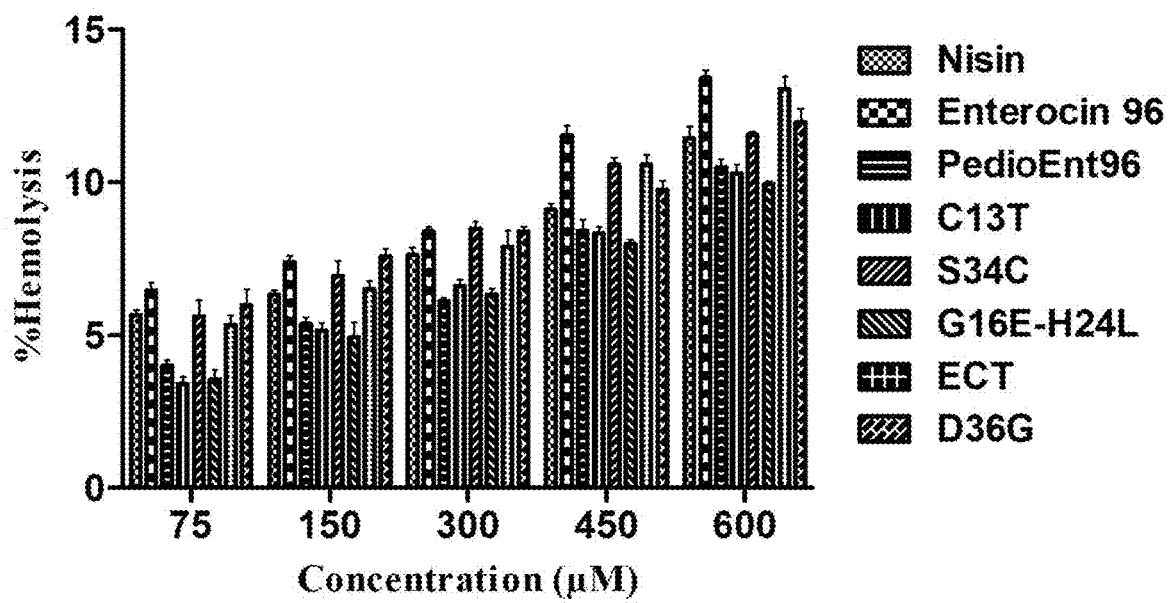
Figure 6B:
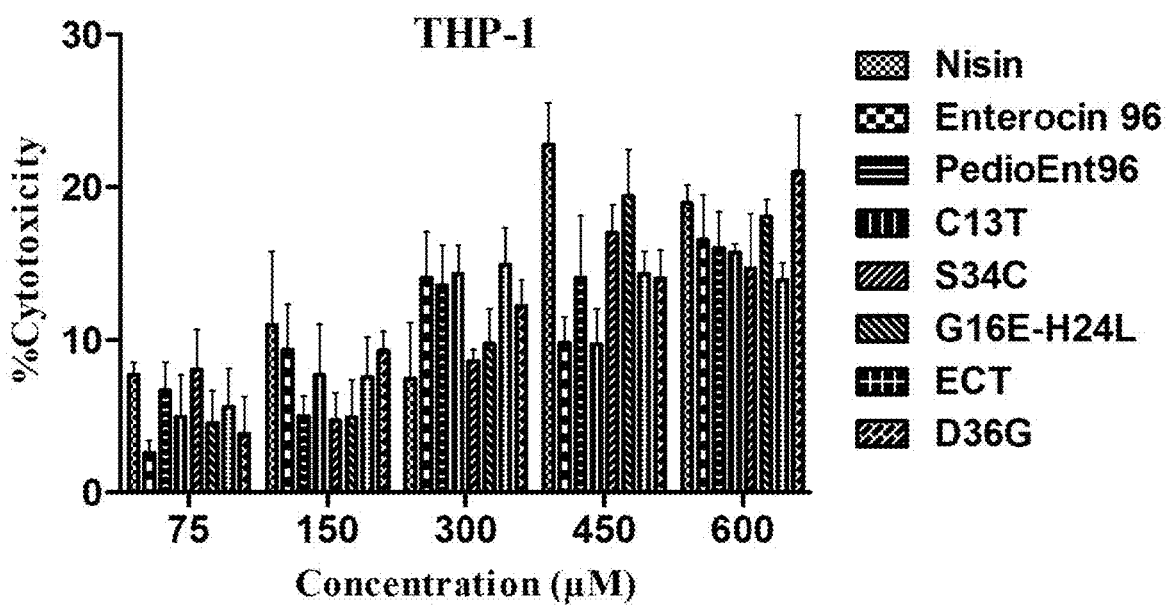
Figure 6C:
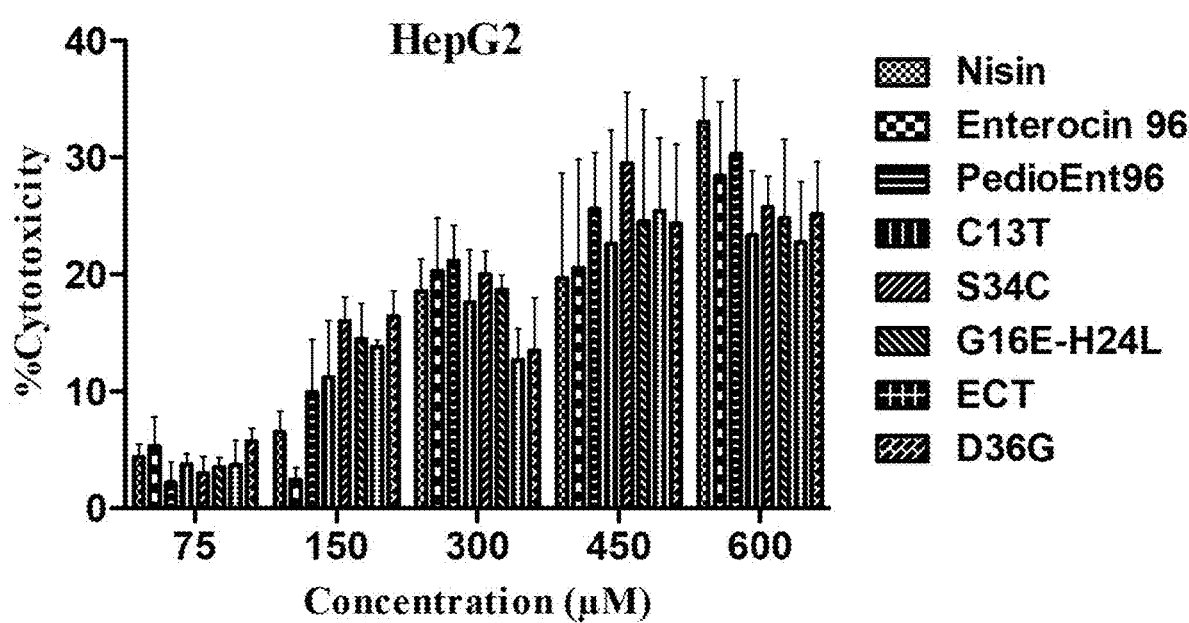

FIG. 6: Illustrates the comparative percent hemolysis (FIG. 6a) and percent cytotoxicity (FIGS. 6b and 6c) observed against the cell lines THP-1 (FIG. 6b) and HepG2 (Cancer cell line)(FIG. 6c) of Nisin, diglycosylated Enterocin 96 (SEQ ID NO: 9) and neo-glycocins produced using the recombinant microbial system of the present invention (SEQ ID NO: 10, SEQ ID NO: 11, SEQ ID NO: 40, SEQ ID NO: 41, SEQ ID NO: 42 and SEQ ID NO: 45), in the concentration range of 75-600 µM.

DETAILED DESCRIPTION OF THE SEQUENCE LISTING

SEQ ID NO. 1: DuetEntsAS1: Recombinant gene cassette encoding EntS (Y) and enterocin 96 (X) design of which is described as construct A of the present invention (2517 bp)

SEQ ID NO. 2: DuetEntsAS2: Recombinant gene cassette encoding EntS (Y) and sublancin (X) design of which is described as construct A of the present invention (2493 bp)

SEQ ID NO. 3: DuetEntsAS3: Recombinant gene cassette encoding EntS (Y) and glycocin F (X) design of which is described as construct A of the present invention (2512 bp)

SEQ ID NO. 4: DuetSunSAS2: Recombinant gene cassette encoding SunS (Y) and sublancin (X) design of which is described as construct A of the present invention (2421 bp)

SEQ ID NO. 5: DuetGccAAS3: Recombinant gene cassette encoding GccA (Y) and glycocin F(X) design of which is described as construct A of the present invention (2440 bp)

SEQ ID NO. 6: Acceptor substrate 1 (AS1): Amino acid sequence of enterocin 96 (X) in fusion with cleavable MCH tag, design of which is described as construct A and B of the present invention (314 aa)

SEQ ID NO. 7: Acceptor substrate 2 (AS2): Amino acid sequence of sublancin (X) in fusion with cleavable MCH tag, design of which is described as construct A and B of the present invention (306 aa)

SEQ ID N. 8: Acceptor substrate 3 (AS3): Amino acid sequence of glycocin F (X) in fusion with cleavable MCH tag, design of which is described as construct A and B of the present invention (311 aa)

SEQ ID NO. 9: Amino acid sequence of enterocin 96 (48 aa)

SEQ ID NO. 10: Glycocin 1: Amino acid sequence of neo-glycocin produced using the recombinant microbial system of the present invention (48 aa)

SEQ ID N. 11: Glycocin 2: Amino acid sequence of neo-glycocin produced using the recombinant microbial system of the present invention (56 aa)

SEQ ID NO. 12: Primer sequence (38 bp)
SEQ ID NO. 13: Primer sequence (30 bp)
SEQ ID NO. 14: Primer sequence (29 bp)
SEQ ID NO. 15: Primer sequence (34 bp)
SEQ ID NO. 16: Primer sequence (26 bp)
SEQ ID NO. 17: Primer sequence (36 bp):
SEQ ID NO. 18: Primer sequence (32 bp)
SEQ ID NO. 19: Primer sequence (34 bp)
SEQ ID NO. 20: Primer sequence (49 bp)
SEQ ID NO. 21: Primer sequence (32 bp)
SEQ ID NO. 22: Primer sequence (49 bp)
SEQ ID NO. 23: Primer sequence (54 bp)
SEQ ID NO. 24: Primer sequence (34 bp)
SEQ ID NO. 25: Primer sequence (34 bp)
SEQ ID NO. 26: Primer sequence (27 bp)
SEQ ID NO. 27: Primer sequence (40 bp)
SEQ ID NO. 28: Primer sequence (32 bp)
SEQ ID NO. 29: Primer sequence (29 bp)

SEQ ID NO. 30: Primer sequence (32 bp)
SEQ ID NO. 31: Primer sequence (34 bp)
SEQ ID NO. 32: Primer sequence (33 bp)
SEQ ID NO. 33: Primer sequence (31 bp)
SEQ ID NO. 34: Primer sequence (32 bp)
SEQ ID NO. 35: Primer sequence (36 bp)
SEQ ID NO. 36: Primer sequence (40 bp)
SEQ ID NO. 37: Primer sequence (60 bp)
SEQ ID NO. 38: Primer sequence (52 bp)
SEQ ID NO. 39: Primer sequence (34 bp)
SEQ ID NO. 40: Variant of Enterocin 96 (49 aa)
SEQ ID NO. 41: Variant of Enterocin 96 (42 aa)
SEQ ID NO. 42: Variant of Enterocin 96 (49 aa)
SEQ ID NO. 43: Variant of Enterocin 96 (49 aa)
SEQ ID NO. 44: Variant of Enterocin 96 (49 aa)
SEQ ID NO. 45: Variant of Enterocin 96 (49 aa)
SEQ ID NO. 46: Variant of Enterocin 96 (49 aa)
SEQ ID NO. 47: Variant of Enterocin 96 (49 aa)
SEQ ID NO. 48: Variant of Enterocin 96 (49 aa)
SEQ ID NO. 49: Variant of Enterocin 96 (49 aa)
SEQ ID NO. 50: Variant of Enterocin 96 (49 aa)
SEQ ID NO. 51: Variant of Enterocin 96 (49 aa)
SEQ ID NO. 52: Variant of Enterocin 96 (49 aa)
SEQ ID NO. 53: Variant of Enterocin 96 (49 aa)
SEQ ID NO. 54: Variant of Enterocin 96 (49 aa)
SEQ ID NO. 55: Variant of Enterocin 96 (49 aa)
SEQ ID NO. 56: Variant of Enterocin 96 (49 aa)
SEQ ID NO. 57: Variant of Enterocin 96 (40 aa)
SEQ ID NO. 58: Variant of Enterocin 96 (49 aa):
SEQ ID NO. 59: Variant of Enterocin 96 (49 aa)
SEQ ID NO. 60: DNA sequence encoding enterocin 96/ent96 (150 bp)
SEQ ID NO. 61: DNA sequence encoding sublancin/sunA (122 bp)
SEQ ID NO. 62: DNA sequence encoding glycocin F/gccF (141 bp)
SEQ ID NO. 63: DNA sequence of recombinant gene encoding EntS (1413 bp)
SEQ ID NO. 64: DNA sequence of recombinant gene encoding SunS (1341 bp)
SEQ ID NO. 65: DNA sequence of recombinant gene encoding GccA (1341 bp)
SEQ ID NO. 66: DNA sequence of vector pRSFDuet-1 (3829 bp)
SEQ ID NO. 67: DNA sequence of vector pTXB1 (6706 bp)
SEQ ID NO. 68: DNA sequence of vector pRSFDuet-1_SapI (3829 bp)

DETAILED DESCRIPTION OF THE INVENTION

Before the present invention is disclosed and described, it is to be understood that this invention is not limited to the particular process steps and material disclosed herein, as such process steps and materials may vary to some degree. It is also to be understood that the terminology used herein is used for the purpose of describing particular embodiments only and is not intended to be limiting as the scope of the present invention will be limited by appended claims and equivalent thereof. In order to make the matter of the invention clear and concise, the following definitions are provided for specific terms used in the following description.

The term "Glycocin" (glycosylated bacteriocins, e.g. glycocin F, ASM1, sublancin 168, thurandacin, enterocin F4-9 and Enterocin 96) are bacterial toxins that constitute a subset of ribosomally synthesised and post-translationally modified peptide (RiPP) natural products. O- and S-glycocins further refers to O-linked and S-linked glycocins (3).

The term "Neo-glycocin" used in the present invention refers to the variants of glycocin obtained by both random mutagenesis and or site directed mutagenesis in the DNA sequence encoding the glycocin The term "Gene cassette" is a manipulable fragment of DNA carrying and capable of expressing, one or more genes of interest between one or more sets of restriction sites. The term "Acceptor substrate" with reference to the present invention is a biomolecule, which is an oligosaccharide, monosaccharides, polypeptide, lipid, small organic molecule, or even DNA. When the acceptor substrate is contacted with the corresponding glycosyltransferase and sugar donor substrate, and other necessary reaction mixture components; and the reaction mixture is incubated for a sufficient period of time, the glycosyltransferase transfers sugar residues from the sugar donor substrate to the acceptor substrate. The acceptor substrate will often vary for different types of a particular glycosyltransferase.

The term "suitable Acceptor substrate" and or "Acceptor Sequence" here are used interchangeably and means, a peptide/polypeptide sequence harboring the minimum sequon required for enzymatic glycosylation and as defined by the acceptor specificity of the corresponding glycosyltransferase.

An expression cassette is a distinct component of vector DNA consisting of a gene and regulatory sequence to be expressed by a transformed cell. In each successful transformation, the expression cassette directs the cell's machinery to make RNA and proteins.

The term "Recombinant microbial system" is a microbial transformant harboring recombinant expression cassette and capable of working such as produce a protein/peptide, or an RNA (ribonucleic acid), either inside or outside a cell. Such systems are commonly used in research and in the commercial production of enzymes or therapeutics.

The terms "Glyco-randomization" and "Glyco-diversfication" are used interchangeably herein refer to rapid diversification of bioactive small molecules, peptides, drug leads and/or approved drugs through the attachment of sugars.

The terms "Glycoactive" is used to describe activity of those glycocins wherein their bioactivity (bacteriostatic or bactericidal) is dependent upon glycosylation. In other words, such bacteriocins are bioactive only upon specific glycosylation.

The term "Glyco-conjugate" refers to general classification for carbohydrates covalently linked with other chemical species such as proteins, peptides, lipids and saccharides.

The term "Expression" refers to transcription or translation, or both, as context requires. The term "Directed Evolution" is interchangeably used with "laboratory evolution" refers to a method used in protein engineering that mimics the process of natural selection to evolve proteins or nucleic acids toward a user-defined goal. It consists of subjecting a gene to iterative rounds of mutagenesis (creating a library of variants), selection (expressing the variants and isolating members with the desired function), and amplification (generating a template for the next round). It can be performed in vivo (in living cells), or in vitro (free in solution or microdroplet). Directed evolution is used both for protein engineering as an alternative to rationally modified proteins, as well as studies of fundamental evolutionary principles in a controlled, laboratory environment.

The present invention relates to a recombinant microbial system for directed evolution of glycocins. More particularly, the recombinant microbial system is designed to co-evolve acceptor substrate (AS) and its corresponding glycosyltransferase enzyme (GT) to generate O- and/or S-linked neo-glycocins. The invention also discloses a method for production and screening of O- and/or S-linked neo-glycocins using the recombinant microbial system.

The recombinant microbial system of the present invention comprises a cloning vector having a gene cassette comprising a DNA sequence encoding glycosyltransferase and a DNA sequence encoding an acceptor substrate, such that the acceptor substrate is in conjugation with a fusion protein tag under the control of two independent inducible promoters. The gene cassette is expressed in E. coli strain KRX (deposited in International Microorganism Depository and Gene Bank, Chandigarh (MTCC) vide MTCC accession No. 25184) for expression and propagation.

The recombinant microbial system comprises a suitable vector harboring a gene cassette expressing glycosyltransferase and its acceptor substrate, herewith referred as gene cassette A of the present invention (FIG. 2A). The gene cassette A is a component of a recombinant expression vector described as a vector A of the present invention (FIG. 3A). The recombinant expression vector is transformed and expressed in an appropriate host such as E. coli for the co-expression of glycosyltransferase and its acceptor substrate.

The gene cassette A of the recombinant microbial system is subjected to mutagenesis strategies selected from the group consisting of random mutagenesis and site-directed mutagenesis, in vitro, and then mutated gene cassette A is transformed in a suitable host to generate the libraries of mutants/variants. Such libraries are further subjected to screening to isolate O- and/or S-neo-glycocins (FIG. 4C).

The recombinant microbial system of the present invention comprises a recombinant duet expression vector corresponding to design vector A (FIG. 3A). The duet vector comprises the components: DNA encoding an enzyme S-tagged glycosyltransferase and its acceptor protein/peptide, which are expressed as a fusion protein with dual affinity tags (MCH) that is suitable for two types of affinity purifications. The restriction sites present are NcoI, SapI, BamHI, HindIII, NdeI, XhoI. The vector system is expressed in a microbial host such as E. coli KRX, (# L3002, Promega) E. coli BL21 (DE3) (New England Biolabs (NEB), (Cat. # C2527H), E. coli Lemo (DE3) (New England Biolabs, (NEB), (Cat. # C2528H), E. coli SHuffle T7 (New England Biolabs, (NEB), (Cat. # C3029H) or E. coli Rosetta (DE3) (Novagen, #70954), E. coli TOP10 (Invitrogen, Cat. # C4040-10) for expression and propagation (FIG. 1, Table 1).

TABLE 1

List of bacterial strain and plasmids used

| Bacterial Strain and Plasmids | Company/Resource Name |
| --- | --- |
| E. coli TOP10 | Invitrogen, Cat. # C4040-10 |
| E. coli KRX | Promega, # L3002 |
| E. coli BL21 (DES) | New England Biolabs (NEB), Cat. # C2527H |
| E. coli SHuffle ® T7 Express | New England Biolabs. (NEB), Cat. # C3029H |
| E. coli Rosetta ™(DE3) | Novagen, # 70954 |
| E. coli Lemo21 (DE3) | New England Biolabs, (NEB), Cat. # C2528H |
| Bacillus subtillis 168 | BEI # NR-607 NIH, Biodefense and Emerging Infections Research Resources Repository (BEI), NIAID, NIH as part of the Human Microbiome Project, Manassas, USA |
| Lactobacillus plantarum | MTCC # 2621 The Microbial Type Culture Collection and Gene Bank (MTCC), CSIR-IMTECH, Chandigarh. |
| Listeria monocytogenes EGD-e, | BEI # NR114 NIH Biodefense and Emerging Infections Research Resources Repository (BEI), NIAID, NIH as part of the Human Microbiome Project, Manassas, USA |
| Vibrio cholera | MTCC # 3904 The Microbial Type Culture Collection and Gene Bank (MTCC), CSIR-IMTECH, Chandigarh. |
| Listeria monocytogenes | MTCC # 839 (The Microbial Type Culture Collection and Gene Bank (MTCC), CSIR-IMTECH, Chandigarh. |
| E. coli | MTCC # 1610 (The Microbial Type Culture Collection and Gene Bank (MTCC), CSIR-IMTECH, Chandigarh. |
| Bacillus licheniformis | MTCC # 9857 (The Microbial Type Culture Collection and Gene Bank (MTCC), CSIR-IMTECH, Chandigarh. |
| Bacillus halodurans | MTCC # 7181 (The Microbial Type Culture Collection and Gene Bank (MTCC), CSIR-IMTECH, Chandigarh. |
| Enterococcus fecalis TX0104 | BEI # HM-201 NIH Biodefense and Emerging Infections Research Resources Repository (BEI), NIAID, NIH as part of the Human Microbiome Project, Manassas, USA |
| pRSFDuet-1 | Novagen, # 71341-3 |
| pTXB1 | New England Biolabs, (NEB), Cat. # N6707S |
| SunS | GenScript (Custom synthesized gene) 860 Centennial Ave., Piscataway, NJ 08854, USA |
| EntS | GenScript (Custom synthesized gene) 860 Centennial Ave., Piscataway, NJ 08854, USA |
| GccA | GenScript (Custom synthesized gene) 860 Centennial Ave., Piscataway, NJ 08854, USA |

TABLE 1-continued

List of bacterial strain and plasmids used

| Bacterial Strain and Plasmids | Company/Resource Name |
| --- | --- |
| Enterocin 96 | PCR amplified using custom synthesized primers from Bioserv and template of genomic DNA of *Enterococcus fecalis* TX0104, HM-201. |
| SunA | PCR amplified using custom synthesized primers from Bioserv and template of genomic DNA of *Bacillus subtillis* 168. |
| GccF | PCR amplified using custom synthesized primers from Bioserv and template of genomic DNA of *Lactobacillus plantarum* MTCC 2621 |
| *E. coli* KRX | MTCC # 25184 |
| pRSFDuet-1EntSAS1 (Recombinant system of the present invention) | The Microbial Type Culture Collection and Gene Bank (MTCC), CSIR-IMTECH, Chandigarh. |

The recombinant microbial system of the present invention comprises a vector for co-expression of an enzyme and its substrate. The recombinant expression vector comprising the gene cassette A is expressed in *E. coli* cultured in Luria-Bertani (LB) broth at 37° C. The culture medium is stabilized with filtered and sterilized antibiotics such as kanamycin, ampicillin, and chloramphenicol at final concentrations of 50 μg/mi, 100 μg/ml and 35 μg/mi respectively, for the *E. coli* strain.

The invention further discloses methods for construction of recombinant microbial system and screening of O- and/or S-neoglycocins and corresponding glycosyltransferase variants, as applicable. The method of construction of the recombinant microbial system comprises the selection of a suitable plasmid and vector system, subjecting the desired gene to PCR amplifications, restriction digestions and cloning the desired gene along with the components by tagging with specific site, expressing the cloning vector in a suitable host.

The recombinant microbial system comprising the gene cassette A having the polynucleotide sequence as set forth in SEQ ID NO: 1, SEQ ID NO: 2, SEQ ID NO: 3, SEQ ID NO: 4 and SEQ ID NO: 5 are customized for directed evolution of glycosyltransferase and its substrate simultaneously by varying the DNA sequence by mutagenesis. The system is further capable of a high throughput directed evolution of the proteins/peptides. The system results in a production of mutant libraries of O- and/or S-glycosyltransferase as well as O- and/or S-linked glycocins. The recombinant microbial system acts as a tool to produce neo-glycoactive glycopeptides in vivo.

The recombinant microbial system comprises a gene cassette A having the polynucleotide sequence as set forth in SEQ ID NO: 1 with a length of 2517 base pairs (bp) encoding glycosyltransferase enzyme (EntS) and acceptor substrate 1 (enterocin 96) fusion protein; a gene cassette A having the polynucleotide sequence as set forth in SEQ ID NO: 2 with a length of 2493 bp encoding glycosyltransferase enzyme (EntS) and acceptor substrate 2 (sublancin) fusion protein; a gene cassette A having the polynucleotide sequence as set forth in SEQ ID NO: 3 with a length of 2512 bp, encoding glycosyltransferase enzyme (EntS) and acceptor substrate 3 (glycocin F) fusion protein; a gene cassette A having the polynucleotide sequence as set forth in SEQ ID NO: 4 with a length of 2421 bp encoding glycosyltransferase enzyme (SunS) and acceptor substrate 2 (sublancin) fusion protein; and a gene cassette A having the polynucleotide sequence as set forth in SEQ ID NO: 5 with a length of 2440 bp, encoding glycosyltransferase enzyme (GccA) and acceptor substrate 3 (glycocin F) fusion protein.

The invention is not only restricted to pRSFDuet-1 and its SapI mutant, but is also applicable to pTXB1 vector (New England Biolabs, Cat. # N6707S). Similarly, the restriction sites and the hosts are varied to create multiple vector systems and recombinant systems. In addition to glycosyltransferase enzyme (EntS), the recombinant microbial system is extendable to other glycosyltransferase enzymes of GT2 family such as SunS (NP_390028), ThuS (ZP_0409994), GccA (ADV57361), EnfC (BAR87971), AsmA (AOF43520.1), PalS (WP_066251544.1).

The present invention is not only restricted to acceptor substrate 1 fusion protein (enterocin 96 in fusion with cleavable MCH tag) having the amino acid sequence as set forth in SEQ ID NO: 6, acceptor substrate 2 fusion protein (sublancin in fusion with cleavable MCH tag) having the amino acid sequence as set forth in SEQ ID NO: 7, and acceptor substrate 3 fusion protein (glycocin F in fusion with cleavable MCH tag)having the amino acid sequence as set forth in SEQ ID NO: 8, but is extendible to other glycosylated bacteriocins, e.g. ASM1 (C7G1H4.1), sublancin 168 (WP_009967544.1), thurandacin (WP_000661240.1), enterocin F4-9 (BAR87969.1), bacillicin CER074 (WP_061530458.1), bacillicin BAG2O (WP_016082806.1), listeriocytocin (WP_041176876.1), geocillicin (WP_066251537.1), pallidocin (KZM53253.1) and similar other glycoactive bacteriocins/peptides such as urancin (3, 7, 14, 15).

Further, a series of vector A such as EntSAS1MCHpRSFDuet-1SapI comprising the gene cassette DuetEntSAS1(SEQ ID NO: 1); EntSAS2MCHpRSFDuet-1Sap1 comprising the gene cassette DuetEntSAS2(SEQ ID NO: 2); EntSAS3MCHpRSFDuet-1Sap1 comprising the gene cassette DuetEntSAS3 (SEQ ID NO: 3); SunSSAS2MCHpRSFDuet-1Sap1 comprising the gene cassette DuetSunSSAS2 (SEQ ID NO: 4) and GccAAS3MCHpRSFDuet-1Sap1 comprising the gene cassette DuetGccAAS3 (SEQ ID NO: 5) were constructed by varying the component Y and/or component X as described in vector A design by using suitable primers selected from the group consisting of SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 34, SEQ ID NO: 35, SEQ ID NO: 36, SEQ ID NO: 37, SEQ ID NO: 38 and SEQ ID NO: 39 and sub cloning as known to people skilled in art (FIG. 3A). The sequence of the gene constructs is confirmed by DNA sequencing. The vector is subjected to one or more than one mutational strategy such as random mutagenesis, site directed and or saturation mutagenesis of acceptor substrate or glycosyltransferase sequentially or simultaneously. The PCR and ligation mixture is transformed into suitable E. coli strain such KRX (Promega, # L3002) or TOP10 and the transformants are selected on LB agar plates containing 50 µg/ml kanamycin and confirmed by colony PCR. Each colony from plate is picked and inoculated in 96 well plate containing LB media containing 50 µg/ml kanamycin and grown overnight at 37° C. for 12 h. A 24 well plate containing 3 ml LB media supplemented with 50 µg/ml kanamycin is inoculated with overnight cultures and protein expression is induced using 1% L-Rhamnose and 1 mM IPTG. The cells are harvested after 4 h of growth at 37° C., centrifuged, washed and resuspended in cleavage buffer at 4° C. for 1 h. The lysates are then tested for bioactivity against indicator strain L. monocytogenes EGD-e (BEI # NR114, NIH Biodefense and Emerging Infections Research Resource Repository (BEI), NIAID, NIH as part of the Human Microbiome Project, Manassas, USA). The mutants exhibiting bioactivity are selected and further analyzed and corroborated for glycosylation status using one or more methods such as PAS staining, Lectin blotting, Mass spectrometry. Similarly, glycocins and neo-glycocins are isolated, purified and analyzed for antimicrobial activity and subjected to further rounds of mutagenesis. The present invention is not limited to pRSFDuet-1 vector but also can be applicable to other series of Duet-1vectors such as pACYCDuet-1, pETDuet-1, pCDFDuet-1 and pCOLA-Duet-1.

The present invention further discloses a facile method to generate libraries of bioactive O- and S-neoglycocins (FIG. 4C). Glycocins are more compatible for in vitro laboratory evolution by means of library generation using recombinant microbial system rather than by chemical synthesis. The libraries further provide a large number of O- and S-neo-glycocins that are screened for a variety of applications in therapeutics, cosmetics or to explore the basic biology of such modifications and their interactions with effect on living cells. Further, depending upon the nature and sequence of the mutagenesis strategy adopted, the system provides a library of neo-glycopeptides, neo-glycocins, and neo-glycoactive glycocins. The recombinant microbial system and the method of construction followed by bioactivity guided screening of the present invention results in production of neo-glycocins having the amino acid sequence as set forth in SEQ ID NO: 10, SEQ ID NO:11, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, and SEQ ID NO:59.

The recombinant microbial system of the present invention is optimized for in vivo generation and bioactivity guided screening and selection of both O- and S-neo-glycocins by modifying the choice of host strain or enzyme-substrate combinations. The recombinant microbial system of the present invention also provides for a cheaper, faster and non-enzymatic method of tag removal from the leader-less neo-glycocin generated in vivo without affecting their bioactivity.

Further, the recombinant microbial system of the present invention is not dependent on inefficient processes such as in vitro oxidative folding or use of disulphide creating microbial strain to produce a bioactive variant. However, the gene cassette A is easily transformed in a microbial strain with disulphide making ability such as E. coli SHuffle T7. Hence use of such strains additionally provides O- or S-neo-glycocins wherein disulphide bonds are intact, which is required for bioactivity.

The recombinant microbial system of the present invention provides an optimized system and method for high yield and cost-effective production of neo-glycocins for downstream applications and is amenable to all mutagenesis methods for directed evolution of an enzyme, a substrate or both in vivo. The system has the technical advantage of comprising an expression vector system for co-expression and co-evolution of glycosylating enzyme and its antimicrobial peptide substrate, simultaneously.

The recombinant microbial system of the present invention serves a novel high throughput assay system for co-evolution of a glycosyltransferase including rare bifunctional or multifunctional O- and or S-glycosyltransferase along with its substrate and acts as a tool to produce neo bioactive and glycoactive glycopeptides, in vivo. Generally, the glycosylated bioactive peptides are large peptides and the recombinant microbial system of the present invention is advantageous as it is compatible with all mutagenesis methods including random mutagenesis or site directed mutagenesis for library generation. This essentially allows comprehensive flexibility for novel sequence design as well as economical construction of large peptides. The recombinant microbial system of the present invention allows for generation of variants of glycocins as well as novel glycosyltrasnferases with altered specificities, which are useful in discovering novel glycocins as well as basic insights on structure function and mechanistic aspects of such glycosylated peptides and their enzymes. The scope of the present invention is not just limited to directed evolution of glycocins or antimicrobial peptides as described here but it can also be extended to proteins, peptides including therapeutic or industrially important enzymes that harbor (native or engineered) suitable cognate acceptor sequon/sequence of the glycosyltransefrases of the invention or its scope. Accordingly, the invention can also be used as a tool to glycoengineer or evolve a diverse range of proteins/peptides of general or application nature. Further the present invention is also extendable to generation of polysialylated proteins/peptides of therapeutic importance through use of EntS as an iterative O-/S-glycosyltransferase in vivo (17) and as mentioned in PCT publication No. WO2017175239A1.

The recombinant microbial system and the method is useful to generate libraries of bioactive O- and S-linked neo-glycocins. The libraries provide a large number of 0-and S-linked neo-glycocins that can be screened for a variety of applications in therapeutics, cosmetics, agriculture, food preservation etc., or to explore the basic biology of such modifications (18-21).

The recombinant microbial system of the invention is optimized for in vivo generation and bioactivity guided selection of both O- and S-linked neo-glycocins by modifying the choice of the host strain (FIG. 4A to FIG. 4C).

The recombinant microbial system also provides for cheaper, faster and non-enzymatic methods of tag removal from the leaderless neo-antimicrobial peptide generated in vivo without affecting its bioactivity.

The recombinant microbial system additionally provides design and method of pairing of vector A (FIG. 3A) and B (FIG. 3B) of the present invention for co-expression of enzyme and substrate in a bacterial host in a manner that imparts enhancement in production and purification of glycocins and variants thereof The scope of the invention described here extends to generation of all known glycosylated and or glycoactive bacteriocins.

EXAMPLES

The following examples are given by way of illustration of the present invention and therefore should not be construed to limit the scope of the present invention.

Example 1

The protocols described above are standard skill of the art and described in manuals like Maniatis, T., Fritsch, E. F., & Sambrook, J. (1982). *Molecular cloning: A laboratory manual*. Cold Spring Harbor, N.Y: Cold Spring Harbor Laboratory.

Cloning and Construction of Recombinant Vector Harboring Expression Cassette DuetEntSAS1 and System Thereof The vector system used was pRSFDuet-1 vector (Novagen #71341-3). Then, the nucleotide sequence of pRSF-Duet-1 was mutated through site directed mutagenesis to construct pRSFDuet-1SapI vector using primer SEQ ID NO: 12. Next, the custom synthesized nucleotide sequence having the sequence as set forth in SEQ ID NO: 63 encoding the glycosyltransferase (GT) such as EntS(Protein ID: WP_002382823.1 GI: 488313438) was amplified using gene-specific primers SEQ ID NO: 13 and SEQ ID NO: 14 containing NdeI and XhoI restriction sites. The PCR amplified EntS and the vector pRSFDuet-1SapI were digested with restriction enzymes NdeI and XhoI and the digested fragments were purified. The purified digested insert EntS and vector pRSFDuet-1 were subjected to ligation using T4 DNA ligase. Further, the ligation mixture was transformed into *E. coli* TOP10 (Invitrogen, Cat. # C4040-10) host using heat shock method. The transformants were selected on kanamycin resistant agar plate at a final concentration of 50 µg/ml LB medium incubated at 37° C. for 12 h. The transformants carrying EntSpRSFDuet-1SapI construct were identified by gene-specific PCR. The recombinant construct EntSpRSFDuet-1SapI was isolated and the transformant were verified by restriction digestion. Next, the nucleotide sequence of acceptor substrate AS1 gene having the sequence as set forth in SEQ ID NO: 60 was amplified using template genomic DNA of *E. fecalis* TX0104 (BEI # HM-201, NIH Biodefense and Emerging Infections Research Resource Repository (BEI), MAID, NIH as part of the Human Microbiome Project, Manassas, USA) and gene specific primers SEQ ID NO: 15 and SEQ ID NO: 16 containing NcoI and BamHI restriction sites. The amplified PCR product was digested with NcoI and BamHI and finally ligated into NcoI and BamHI linearized EntSpRSFDuet-1SapI vector, obtaining EntSAS1pRSFDuet-1SapI. The ligation mixture was transformed into *E. coli* TOP10 cells using heat shock method and the transformants were selected on LB-kanamycin agar plate incubated at 37° C. for 12 h. The sequence of the gene construct was confirmed by restriction digestion. The fusion tag MC was amplified from a suitable vector selected from the group consisting of pTWIN1, pTXB1 and pTXB3 using primers SEQ ID NO: 18 and SEQ ID NO: 19 containing BamHI and HindIII restriction sites. Thus, obtained PCR product were digested with BamHI and HindIII and ligated into BamHI and HindIII linearized EntSAS1pRSFDuet-1SapI vector, obtaining EntSAS1MCpRSFDuet-1SapI recombinant vector. The fusion tag MC was extended in to MCH tag using primers SEQ ID NO: 18 and SEQ ID NO: 20 and PCR approach followed by restriction digestion, ligation and transformation and selection of transformants harboring EntSAS1MCHpRSFDuet-1SapI vector. The nucleotide sequence of acceptor substrate AS1 gene having the sequence as set forth in SEQ ID NO: 60 was PCR amplified using suitable primers SEQ ID NO: 15 and SEQ ID NO: 17 and sub-cloned in NcoI and SapI sites of EntSAS1MCHpRSFDuet-1SapI vector to generate the vector A comprising the gene cassette A (FIG. 3A).

While cloning the nucleotide sequence encoding the acceptor peptide AS1, the DNA sequence is introduced inside NcoI and BamHI sites of the EntSpRSFDuet-1SapI vector. Wherein reverse primer (SEQ ID NO: 17) provides for a SapI site in the insert internal to BamHI restriction site. BamHI site was further used to create MCH fusion tag. The Sap I site introduced at the C terminus of the insert during third cloning step is utilized in last cloning step, to re-clone the nucleotide sequence encoding the acceptor peptide AS1 at NcoI and SapI site of the vector EntSAS1MCHpRSFDuet-1SapI. Use of SapI site in last cloning step facilitated (a) removal of extra (unrequired) nucleotides between SapI and BamHI site of the vector at the C terminus of the insert; and (b) exchange of nucleotide sequences encoding acceptor peptide AS1 with nucleotide sequences encoding other acceptor peptides such as AS2 and AS3.

Method for Directed Evolution of Glycocin and High Throughput Bioactivity Guided Screening of Neo-Glycocin Enterocin 96 is a known diglucosylated antimicrobial peptide (glycocin) and is regarded as a potential food preservative akin Nisin. The bioactivity of Enterocin 96 is directly correlated with length and nature of the attached glycan, wherein monoglucosylated or monogalactosylated Enterocin 96 is less active against common food born pathogen *L. monocytogenes* then its diglucosylated form. While monoglycosylated form is more suitable for homogenous production of the glycocin, it suffers poor bioactivity in comparison to diglucosylated Enterocin 96, the parent peptide/glycocin (9).

Therefore, for directed evolution of the acceptor substrate, Enterocin 96 is co-expressed with its glycosyltransferase enzyme EntS; and for simultaneous bioactivity guided high throughput screening of neo-glycocins (variants of glcocin), an optimized method is developed using recombinant microbial system of the present invention.

The recombinant expression vector harboring gene cassette A having the polynucleotide sequence as set forth in SEQ ID NO: 1 was subjected to two selected mutational strategies; random mutagenesis and site directed mutagenesis of acceptor substrate and glycosyltransferase sequentially as well as simultaneously as per standard protocol known to the person skilled in art using applicable primers having the sequence as set forth in SEQ ID NO: 32 and SEQ ID NO: 33 for enzyme (EntS); and primers having the sequence as set forth in SEQ ID NO: 34 and SEQ ID NO:35 for Enterocin 96 for random mutagenesis; and primers having SEQ ID NO: 36, SEQ ID NO:37 and SEQ ID NO:17 for site directed mutagenesis.

After employing mutational strategies, the library of mutants was transformed into a suitable expression host *E. coli* KRX on 50 µg/ml kanamycin plate.

For bioactivity guided high throughput screening, each colony from plate was picked and inoculated in 96 well plate containing LB media supplemented with 50 µg/ml kanamycin and grown overnight at 37° C. in a rotary shaker 120 rpm. The 1% of the overnight culture was transferred into 24 well plate containing 3 ml of fresh LB broth in each well supplemented with 50 µg/ml kanamycin and cultivated at 37° C. Once the optical density ($OD^{600}$) of the culture read 1.0, 1% L-Rhamnose and 1 mM of IPTG was added to induce expression of the mutants. The cultivation was continued for 4 h at 37° C. Further, the cells were harvested by centrifugation at 3000 rpm for 20 min at 4° C. and cell pellets were washed with 1×PBS 3 times to remove residual antibiotic. After washing, pellets were resuspended in 200 µl of cleavage buffer at 4° C., incubated for 1 h to obtain neo-glycocins.

Simultaneously, to check the change in spectrum of bioactivity of neo-glycocins, the agar plates of *L. monocytogenes* EGD-e seeded with approximately $10^7$ bacterial cells were prepared. A 100 µL of cell lysate of mutants were added into the each well and then the plate was incubated at 4° C. for 1 h followed by overnight incubation at 37° C. The presence of inhibition zones around the wells was checked. The antimicrobial activity was determined by monitoring the zone of growth inhibition. The mutants exhibiting zone of inhibition were selected and the mutation in the sequence of the selected mutant plasmid was confirmed using DNA sequencing. The glycosylation status of the neo-glycocin produced from the selected mutant were analyzed using PAS staining and MALDI-TOF and LC-ESI-MS analysis as discussed below. Using this method, the bioactive neo-glycocins having amino acid sequence as set forth in SEQ ID NO:10 and SEQ ID NO:11 were identified that exhibited different antimicrobial spectrum than the antimicrobial spectrum known for native glycocin (FIG. 5B a-i).

Further, the bioactivity assay of the neo-glycocins is extendable against gram positive, and gram negative bacteria and other microbes including fungi.

In order to check in vivo glycosylation of acceptor substrate 1 (AS1) (having amino acid sequence as set forth in SEQ ID NO: 6), PAS staining was performed. For the PAS staining, 12% SDS-PAGE was run and then the gel was washed with milliQ water 3 times to remove any SDS traces. The gel was soaked in 50% methanol to fix the proteins at room temperature on the rocker for 30 min. The gel was then washed with 3% acetic acid for 20 min 2 times. The gel was incubated with 25 ml of oxidizing solution comprising 1% periodic acid in water in a staining box for 30 min. After oxidization step, the gel was washed with 3% acetic acid 4 times for 20 min then incubated with 25 ml of glycoprotein staining solution for 30 min. After glycoprotein staining, next, 25 ml of reducing agent i.e. 1% sodium metabisulphite was added for 30 min and washed several times in 3% acetic acid for 2 h and allowed overnight to ensure good color detection.

The cell pellets were resuspended in 500 µl of cleavage buffer. The presence of glycocin or its variants (neo-glycocin) in the lysate was confirmed using 12.5% SDS-PAGE as well as 20% Tricine-PAGE. The glycosylation status of the glycocin and its variants was confirmed using PAS staining as discussed above. The glycosylation status of the acceptor may also be confirmed using other standard methods including lectin blotting, glycan-specific antibody blotting and or using other glycan specific stains known in the literature.

The cell lysate containing glycocins were directly subjected to agar diffusion test (ADT) using *L. monocytogenes* EGD-e. In ADT, the agar plates seeded with *L. monocytogenes* EGD-e (approximately $10^7$ cells) were prepared. Approximately 100 µL lysate containing glycocin or its variants (neo-glycocin) (SEQ ID NO: 9, SEQ ID NO: 10 and SEQ ID NO: 11) were applied into the wells in the seeded plate followed by incubation of the plate at 4° C. for 1 h. Presence of inhibition zones around the wells was checked post overnight incubation of the plates at 37° C. The antimicrobial activities of the glycocin and neo-glycocin were determined by monitoring the zone of growth inhibition on the plates.

Methods for High Expression and Purification of Glycocin and Neo-Glycocin

Cloning and Construction of Recombinant Expression Vectors $pEC_{NP}HIS_6$, $pEC_{NP}HIS_8$, $pNG2_{NP}HIS_6$ and $pNG2_{NP}HIS_8$ Using vector pTXB1 (New England Biolabs (NEB) (Cat. # N6707S) and suitable primers, a series of high yielding expression vectors were constructed, described as vector B harboring recombinant construct B of the present invention (FIG. 3B). According to construct B (FIG. 2B), to clone the glycocin, the gene encoding enterocin 96 (Protein ID: EEI13075.1) was PCR amplified from the template harboring construct DuetEntSAS1 using primers having the sequence as set forth in SEQ ID NO: 21 and SEQ ID NO: 17. The amplified insert encoding enterocin 96 having the amino acid sequence as set forth in SEQ ID NO: 9, was digested with NheI and SapI and ligated with NheI and SapI linearized pTXB1 vector leading to creation of vector pECNS. The ligation mix was transformed into *E. coli* TOP10. The transformants were selected on ampicillin antibiotic agar plate at a final concentration of 100 µg/ml in LB medium and incubated at 37° C. for 12 h. The transformants harboring pECNS were confirmed by DNA sequencing. Using pECNS as template and SEQ ID NO: 21, SEQ ID NO: 22, and SEQ ID NO: 23 as primers, the PCR product was generated and subbcloned in NheI and PstI digested pTXB1 to create $pEC_{NP}HIS_6$ and $pEC_{NP}HIS_8$, respectively. The ligation mix was transformed into *E. coli* TOP10. The transformants were selected on ampicillin antibiotic agar plate at a final concentration of 100 µg/ml in LB medium incubated at 37° C. for 12 h. The transformants harboring $pEC_{NP}HIS_6$ or $pEC_{NP}HIS_8$ were identified by colony PCR as well as restriction digestion of the isolated plasmids. Similarly, the DNA sequence encoding neo-glycocin (SEQ ID NO: 11) was subcloned to replace the DNA sequence encoding enterocin 96 (Protein ID: EEI13075.1) in $pEC_{NP}HIS_6$ and $pEC_{NP}HIS_8$ using primers having sequence as set forth in SEQ ID NO: 37, SEQ ID NO: 22 and SEQ ID NO: 37, SEQ ID NO: 23 to generate $pNG2_{NP}HIS_6$ and $pNG2_{NP}HIS_8$, respectively.

Purification of Recombinant Glycocin or Neo-Glycocin Using Affinity Chromatography For high expression and large-scale purification of glycocin or neoglycocin, the recombinant expression vectors, DuetEntSAS1 (vector A) and $pEC_{NP}HIS_6$ (vector B) were co-transformed into an expression host *E. coli* Lemo21 (DE3) (New England Biolabs, (NEB) (Cat. # C2528H). A single-colony of the co-transformant was inoculated into 10 ml LB supplemented with 50 µg/ml kanamycin, 100 µg/ml ampicillin and 35 µg/ml chloramphenicol and grown overnight at 37° C. in a rotary shaker at the rate of 200 rpm. The 1% of the overnight culture was transferred to 1 L of fresh LB broth cultivated at 37° C. Once the optical density ($OD^{600}$) of the culture read 1.0, 1% L-Rhamnose and 1 mM IPTG was added to induce expression of the AS1 having amino acid sequence as set forth in SEQ ID NO: 6. The cultivation was continued for 16 h at 25° C. Further, the cells were harvested by centrifugation at 8000 rpm for 20 min at 4° C. The cell pellets were thawed at 4° C. and suspended in 30 ml of lysis buffer B1. The lysis buffer B1 comprises 50 mM Tris-HCl at pH 7.5, 5% glycerol, 1 M sodium chloride supplemented with 1 mM PMSF. The cell mixture was disrupted by sonication in an ice bath for 60 min with cycles of 10 sec on, 10 sec off and at the amplitude of 35%. The recombinant protein was recovered in the form of a supernatant by centrifugation at 12000 rpm for 30 min. The over-expression was checked by running 12.5% SDS-PAGE (FIG. 5Aa). The glycosylation status of AS1 in lysate fraction was checked using PAS staining as discussed previously (FIG. 5Ab). Further, Chitin-based resin (CBD-beads) were prepared by three consecutive washes in 20 mL of lysis buffer.

The cell supernatant was mixed with 2 mL resin slurry per 1 L of expression cell culture and incubated at 4° C. for 16 h with previously washed and pre-equilibrated chitin-based resin. After 16 h binding, the cell supernatant was passed through the column and the flow through was collected. The recombinant protein bound to CBD-beads was washed to remove the contaminants with 50 ml of the lysis buffer followed by rapid flashing of 20 ml of cleavage buffer. The column was filled with additional cleavage buffer at the top, capped and incubated at 4° C. for 16 h, to cleave off the CBD-tag.

The glycocin Enterocin 96 (SEQ ID NO: 9) was eluted off the column in the cleavage buffer. The Enterocin 96 was further concentrated using ultra membrane filters and subjected to buffer exchange. Simultaneously, the glycocin present in inclusion bodies was recovered by centrifugation of the cell lysate at 12000 rpm for 30 min. The inclusion bodies were washed with lysis buffer and solubilized in 30 ml of denaturing or solubilizing buffer with 50 mM Tris-HCl at pH 7.5, 5% glycerol, 1 M sodium chloride and urea 8 M and subjected to sonication for 30 min on ice with cycles of 10 seconds on, 10 seconds off and at an amplitude of 35%.

After denaturation, the solubilized inclusion bodies were diluted with 4 M urea with lysis buffer and incubated with washed and pre-equilibrated CBD-beads for 16 h. After 16 h, bound solubilized inclusion bodies lysate was passed through the column and the flow through was collected.

The glycocin bound to CBD-beads was washed to remove the contaminants with 50 ml of solubilizing buffer and then with 20 ml of cleavage buffer containing 4 M urea in rapidly, flashed through the column. The column was then filled with additional cleavage buffer at the top, capped and incubated at 4° C. for 16 h allowing the cleavage of the CBD-tag. The Enterocin 96 (SEQ ID NO: 9) was eluted off the column in cleavage buffer.

The elute containing Enterocin 96 (SEQ ID NO: 9) was dialyzed against dialysis buffer comprising 20 mM Tris-HCl at pH 7.5 and 100 mM sodium chloride and further concentrated using Amicon 3 kDa cut off concentrators. The quality and purity of the elute Enterocin 96 was assessed by SDS-PAGE and Tricine-PAGE gel electrophoresis. The glycosylation status of Enterocin 96 was checked using PAS staining (FIG. 5Ac).

The partially purified glycocin corresponding to ORF WP_002382828.1 was concentrated and subjected to bioactivity checking using ADT (FIG. 5Ad).

The method described above is extendable to glycocin obtained after expression of pEC$_{NP}$HIS$_8$, pNG2$_{NP}$HIS$_6$ and pNG2$_{NP}$HIS$_8$ vectors.

HPLC Purification of Bioactive Glycocin

The partially purified glycocin Enterocin 96 (SEQ ID NO: 9; Protein ID: EEI13075.1) collected from ultra-membrane filters was introduced into reverse-phase high-performance liquid chromatography (RP-HPLC) system equipped with a reverse phase HPLC column. 900 µL of the concentrated fraction was injected on the column, which was previously equilibrated with 5% solvent B. The separation was carried out by gradient separation using two solvents namely: A comprising 0.05% TFA Mili-Q water; and B comprising 0.05% TFA in 100% acetonitrile. The flow rate of the mobile phase was set at 5 ml/ml. The sample was fractionated by employing a gradient of solvent B (5-95%) over 26 min with a flow rate of 5 ml/min and monitored at 220 nm(FIG. 5Ae).

The fractions were collected and vacuum dried to remove acetonitrile and then tested for antimicrobial activity using *L. monocytogenes* EGD-e (BEI # NR114, NIH Biodefense and Emerging Infections Research Resources Repository (BEI), NIAID, NIH as part of the Human Microbiome Project, Manassas, USA) as a test indicator using ADT (FIG. 5Ae; inset).

The method is similarly extendable towards production and purification of other glycocins and neo-glycocins produced from the recombinant system of the present invention. Method for Detection of Bioactive Glycocin (Providing Optimized Mass Spectrometry Conditions)

For MALDI-TOF analysis, vacuum dried samples were reconstituted in water. Matrix Assisted Laser Desorption Ionization Time of flight Mass Spectrometry (MALDI-TOF MS) was carried out at AB Sciex 5800 MALDI TOF/TOF. Mass Spectrometry (MS) Analysis of Purified Glycocin and Neo-Glycocin on MALDI-TOF The active fraction was collected at the same retention time during different HPLC runs and then pooled and lyophilized. The identity of separated species was further confirmed by observing the mass on MALDI-TOF-MS. For MALDI-TOF MS analysis of salt-free samples, 1 µL aliquot of analyte was combined with 1 µL of matrix (α-cyano-4-hydroxy-cinnamic acid matrix in 50% ACN/50% water with 0.1% TFA) and the total volume was spotted onto a MALDI target and dried under ambient conditions prior to analysis. MS data acquisition was done in positive ion mode using fixed laser intensity of 3400, keeping the mass range 400-700 Da, total number of shots 2000, bin size 0.5 ns and pulse rate 400 Hz. The mass spectrometry profile of these separated species confirmed the diglycosylation status of the glycocin with a 324 Da increase in the calculated mass of the amino acid.

The purified HPLC fractions containing single population were lyophilized and stored at −80° C. The methods described above are equally extendable to other recombinant glycocins or neo-glycocins, in general.
Mass Spectrometry (MS) Analysis Using LC-ESI-Q-TOF 6550 iFunnel Q-TOF LC-MS system (Agilent Technologies) equipped with Agilent Dual jet-stream ESI source was used for Liquid chromatography electrospray ionization mass spectrometry (LC-ESI-Q-TOF MS). For MS analysis, dried sample analyte was reconstituted in 0.1% formic acid and 1 µl volume of reconstituted sample was injected on Agilent UHPLC system equipped with Zorbax Eclipse Plus C8 column (3.0×150 mm, 5 µm, 95 Å) of Agilent technologies, equilibrated in 5% B (solvent A: 0.1% formic acid in water, solvent B: 0.1% formic acid in acetonitrile). A gradient of solvent B (30-90%) was employed over 23 min with 0.4 ml/min flow rate to fractionate the sample. The fractions were then directly subjected to ESI-Q-TOF MS. The data was acquired in .d file format using MassHunter workstation software, version B.05.00 by Agilent Technologies. Post-acquisition, the acquired raw data files were imported to MassHunter qualitative analysis software, version B.05.00 for further processing. The integrated multiple charged ions and deconvoluted mass data were exported to csv file format. The csv files having the peaks list were imported and plotted in Origin (OriginPro 2015 b.9.2.214) (FIG. 5Af).

Determination of the Mic of Enterocin 96 Against *L. monocytogenes*

One colony of an indicator strain (*L. monocytogenes*) was picked from an NB agar plate, inoculated to liquid NB medium and grown at 37° C., in a shaking incubator until $OD^{600\ nm}$ of 0.5 was reached. Then, the culture was diluted with NB medium and serial twofold dilutions with NB medium were made. Hundred microliters of Enterocin 96 solution (1 mg/ml in MQ) were transferred to a 96-well plate and mixed with 100 μl previously prepared cell suspension of sensitive strain. Similarly, positive control Nisin (1 mg/ml in MQ, Sigma Cat. # N5764), 100 μl mixture of NB medium with the *Listeria*, and negative controls (media alone, untreated indicator strain). 100 μL mixture of NB medium were prepared and dispersed in the same 96-well plates. The plate was incubated for 18 h at 37° C. in a shaking incubator. After incubation, the growth of bacteria was evaluated visually and by a plate reader. The analyses were performed in triplicate. Similarly, MIC of other variants of Enterocin 96 (neo-glycocins) was determined using above described method.

Hemolytic Assay

Samples were prepared within 3 h of performing the assay. Neo-glycocins stock solutions of 1 mg/ml were prepared by dissolving the neo-glycocins in PBS (10 mM phosphate buffer, pH 7.4); the samples were mixed by inversion to ensure neo-glycocins were completely dissolved in PBS. To prepare the Human Red Blood Cell (hRBC) solution, blood was collected from healthy individual and RBCs were isolated following standard procedure. Informed consent was acquired from all donors and this work was carried out in compliance with the ethical committee guidelines of CSIR-IMTECH with IEC NO SUIEC/14/03.

2 ml whole blood from healthy individual was centrifuged for 30 mins at 1000 rpm(4° C.). Layer of RBCs was collected and diluted with equal volume of 1×PBS and mixture was centrifuged three times for 10 mins at 1000 rpm, 4° C. To prepare 4% RBC solution, 1 ml of RBC were mixed with 24 ml 1×PBS. To examine the hemolysis property of neo-glycocins (75-1000 μM), 20 μl of freshly prepared neo-glycocins solution was mixed with 180 μl of freshly prepared hRBC solution and was placed at 37° C. for 1 h. A total of 20 μl of PBS buffer only and 20 μl of Triton X-100 1% (w/v) were mixed with 180 μl of hRBC solution as negative and positive controls, respectively. After 1 h of incubation, all samples were centrifuged at 2500 rpm for 10 min. A total of 100 μl of supernatant was collected, and the release of hemoglobin was monitored by measuring the absorbance of the supernatant at 570 nm with a Multiskan Go plate-reader (Thermo Scientific). Hemolysis percentage for each sample was calculated by dividing sample's absorbance on positive control absorbance (complete hemolysis) multiplied by 100.

Cytotoxicity/Anti-Cancer Assay

Cytotoxicity of Enterocin 96 and its variants (neo-glycocins) against THP-1 cells and anti-cancer potential against HepG2 cells was measured by the conventional MTT reduction assay. HepG2 and THP-1 cells ($1\times10^4$ cells/well) were seeded into the 96-well plate and cultured at 37° C. in an atmosphere of 5% $CO_2$ to allow them to adhere overnight. After 24 hours, the cells were exposed to Enterocin 96 and its variants (neo-glycocins) at various concentrations (75-1000 μM) for 18-24 hours. After the incubation period, 150 μl media and the suspended cells were discarded and washed with 200 μl PBS. After that, 200 μl of fresh media was added followed by 20 μl of MTT (5 mg/mL) into each well in the 96-well plate and incubated for 4 h in $CO_2$ incubator. One hundred and fifty microlitres of medium with MTT was removed from every well and 100 μl DMSO was added to each well to solubilize the formazan crystal by incubating for 20 min in $CO_2$ incubator. Finally, the plates were read at 570 nm by using Multiskan Go plate-reader (Thermo Scientific) and then percentage of cell viability was determined.

TABLE 2

List of variants/ mutants generated using the microbial system of the invention

| SI No. | SEQ ID NO: | Mutant name | Sequence | Zone of inhibition as well as glycosylation positive |
|---|---|---|---|---|
| 1 | 10 | C13T (G1/glycocin 1) | MASKRDCNLMKATCAGQAV TYAIHSLLNRLGGDSSDPAGC NDIVRKYCK | Yes |
| 2 | 11 | PedioEnt96 (G2/ glycocin 2) | MASKYYGNGVKRDCNLMK ACCAGQAVTYAIHSLLNRLG GDSSDPAGCNDIVRKYCK | Yes |
| 3 | 40 | S34C | MASKRDCNLMKACCAGQAV TYAIHSLLNRLGGDCSDPAGC NDIVRKYCK | Yes |
| 4 | 41 | ECT (Ent96_C-term truncation) | MASKACCAGQAVTYAIHSLL NRLGGDSSDPAGCNDIVRKY CK | Yes |

TABLE 2-continued

List of variants/ mutants generated using the microbial system of the invention

| SI No. | SEQ ID NO: | Mutant name | Sequence | Zone of inhibition as well as glycosylation positive |
|---|---|---|---|---|
| 5 | 42 | D36G | MASKRDCNLMKACCAGQAV TYAIHSLLNRLGGDSSGPAGC NDIVRKYCK | Yes |
| 6 | 43 | H24Q | MASKRDCNLMKACCAGQAV TYAIQSLLNRLGGDSSDPAGC NDIVRKYCK | Yes |
| 7 | 44 | C13R | MASKRDCNLMKARCAGQAV TYAIHSLLNRLGGDSSDPAGC NDIVRKYCK | Yes |
| 8 | 45 | G16E-H24L | MASKRDCNLMKACCAEQAV TYAIQSLLNRLGGDSSDPAGC NDIVRKYCK | Yes |
| 9 | 46 | G16E | MASKRDCNLMKACCAEQAV TYAIHSLLNRLGGDSSDPAGC NDIVRKYCK | Yes |
| 10 | 47 | D36V | MASKRDCNLMKACCAGQAV TYAIHSLLNRLGGDSSVPAGC NDIVRKYCK | Yes |
| 11 | 48 | N28Y | MASKRDCNLMKACCAGQAV TYAIHSLLYRLGGDSSDPAGC NDIVRKYCK | Yes |
| 12 | 49 | Q17H-N28K | MASKRDCNLMKACCAGHAV TYAIHSLLKRLGGDSSDPAGC NDIVRKYCK | Yes |
| 13 | 50 | C40S | MASKRDCNLMKACCAGQAV TYAIHSLLNRLGGDSSDPAGS NDIVRKYCK | Yes |
| 14 | 51 | R5H | MASKHDCNLMKACCAGQAV TYAIHSLLNRLGGDSSDPAGC NDIVRKYCK | Yes |
| 15 | 52 | A22G | MASKRDCNLMKACCAGQAV TYGIHSLLNRLGGDSSDPAGC NDIVRKYCK | Yes |
| 16 | 53 | Q17L | MASKRDCNLMKACCAGLAV TYAIHSLLNRLGGDSSDPAGC NDIVRKYCK | Yes |
| 17 | 54 | S34P | MASKRDCNLMKACCAGQAV TYAIHSLLNRLGGDPSDPAGC NDIVRKYCK | NO |
| 18 | 55 | D33N | MASKRDCNLMKACCAGQAV TYAIHSLLNRLGGNSSDPAGC NDIVRKYCK | NO |
| 19 | 56 | S34F | MASKRDCNLMKACCAGQAV TYAIHSLLNRLGGDFSDPAGC NDIVRKYCK | NO |
| 20 | 57 | ENT (Ent96_N-term deleted and WRCK AA added) | MASKRDCNLMKACCAGQAV TYAIHSLLNRLGGDSSDWRC K | NO |
| 21 | 58 | S35G | MASKRDCNLMKACCAGQAV TYAIHSLLNRLGGDSGDPAG CNDIVRKYCK | NO |

TABLE 2-continued

List of variants/ mutants generated using the microbial system of the invention

| SI No. | SEQ ID NO: | Mutant name | Sequence | Zone of inhibition as well as glycosylation positive |
|---|---|---|---|---|
| 22 | 59 | D36E | MASKRDCNLMKACCAGQAV TYAIHSLLNRLGGDSSEPAGC NDIVRKYCK | NO |

Directed Evolution of Enterocin 96 and Screening of its Variants (Neo-Glycocins)

Post mutagenesis, approximately 1.5×10³ colonies were observed on 200 mm culture plate. Out of these, almost 600 were screened for bioactivity against *L. monocytogenes* using ADT. Further, a total of 41 representative colonies were selected and sequenced as well as screened for (a) bioactivity, (b) presence or absence of glycosylation using PAS staining with suitable positive and negative controls followed by (c) purification of best zone forming mutants using affinity chromatography (FIG. 5Ba, b, c). The sequences of 41 mutants termed as neo-glycocins (variants/ mutants of peptide Enterocin 96) were analysed for number and position of the mutations.

Among total of 41 neo-glycocins sequenced, 10 had stop codons while 10 turned out to be parent peptide sequences. Out of remaining 22 mutant sequences (Table 2); 14 sequences carried one mutation (SEQ ID NO: 10, SEQ ID NO: 11, SEQ ID NO: 40, SEQ ID NO: 41, SEQ ID NO: 42, SEQ ID NO: 43, SEQ ID NO: 44, SEQ ID NO: 46, SEQ ID NO: 47, SEQ ID NO: 48, SEQ ID NO: 50, SEQ ID NO: 51, SEQ ID NO: 52 and SEQ ID NO: 53); 2 sequences carried two mutations (SEQ ID NO: 45 and SEQ ID NO: 49); and another 6 sequences (SEQ ID NO: 54, SEQ ID NO: 55, SEQ ID NO: 56, SEQ ID NO: 57, SEQ ID NO: 58 and SEQ ID NO: 59) had single mutations at the site of glycosylation/ glycosylation sequon of parent glycocin, the Enterocin 96 (thereby, justifying loss of bioactivity in respective mutants). Out of these finally 16 neo-glycocins having amino acid sequence as set forth in SEQ ID NO: 10, SEQ ID NO: 11, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52 and SEQ ID NO: 53 were found positive for bioactivity as well as glycosylation (using PAS staining) whereas 6 neo-glycocins (SEQ ID NO: 54, SEQ ID NO: 55, SEQ ID NO: 56, SEQ ID NO: 57, SEQ ID NO: 58 and SEQ ID NO: 59)neither showed any bioactivity nor glycosylation after ADT and PAS staining due to loss of glycosylation, respectively. The six of these neo-glycocins found positive for bioactivity as well as glycosylation were purified (SEQ ID NO: 10, SEQ ID NO: 11, SEQ ID NO: 40, SEQ ID NO: 41, SEQ ID NO: 42 and SEQ ID NO: 45) and then subjected to determination of MIC, haemolytic activity and cytotoxicity in comparison to parent type Enterocin 96 (SEQ ID NO: 9) and industry standard Nisin, the antimicrobial peptide with known anti-listerial activity and use in Food Preservation (FIG. 5B a-c and table no 3). A chemo-variant of Enterocin 96, wherein Ser34 is mutated to S34C (SEQ ID NO: 40) was found equally bioactive against *L. monocytogenes* EGDe and *L. monocytogenes* MTCC 839 as the parent peptide (FIG. 5Bd-e). In contrast to Nisin and Enterocin 96, the neo-glycocin named C13T (G1/glycocin 1) having amino acid sequence as set forth in SEQ ID NO: 10 exhibited improved antibacterial spectrum with no significant change in other useful properties like MIC (0.54 μM against *L. monocytogenes*), hemolysis (FIG. 6A) and cytotoxicity (FIGS. 6B and 6C). Similarly, the neo-glycocin named C13T (G1/glycocin 1) having amino acid sequence as set forth in SEQ ID NO: 10 was found to be water soluble, retain bioactivity against *L. monocytogenes* post treatment with pH 2-10 (treated for 24 hours, followed by ADT assay of neutralized peptide solution), as well as post autoclaving at 121° C. for 15 minutes, verified using ADT assay. Using ADT, bioactivity against Gram negative bacteria *Vibrio cholerae* MTCC 3904 and *E. coli* MTCC 1610 as well as Gram positive spore forming bacteria *Bacillus* lichenmformis MTCC 9857 was observed only in neo-glycocin named C13T (G1/glycocin 1) with amino acid sequence as set forth in SEQ ID NO: 10 and not with Enterocin 96 or Nisin (FIG. 5B h and i).

Previously, it is known that monoglucosylated Enterocin 96 is less active as compared to diglucosylated Enterocin 96 (9). But Enterocin 96, contrary to expectation, a length and glycan variant (having amino acid sequence as set forth in SEQ ID NO: 11) containing pediocin box (YYGNGV) through directed insertion at the C-terminal of the Enterocin 96 sequence was found monoglycosylated yet as active as diglycosylated glycocin against *L. monocytogenes*.

TABLE 3

Results of the antimicrobial activity, hemolytic activity, and cytotoxicity/anticancer activity assays carried out with enterocin 96 and its variants/mutants (neo-glycocins) generated using the microbial system of the invention

| SI No. | Peptide ID | Anti-bacterial activity[A] (MIC in μM) | Hemolysis[B] (MHC in μM) | Cytotoxicity [C] (IC$_{50}$ in μM) | Anti-cancer activity [D] (IC$_{50}$ in μM) |
|---|---|---|---|---|---|
| 1 | Nisin | 0.27 | 600 | 368.3 ± 0.1 | 332.6 ± 0.06765 |
| 2 | SEQ ID NO: 9 | 0.54 | 600 | 194.1 ± 0.1192 | 273.4 ± 0.08860 |

TABLE 3-continued

Results of the antimicrobial activity, hemolytic activity, and cytotoxicity/anticancer activity assays carried out with enterocin 96 and its variants/mutants (neo-glycocins) generated using the microbial system of the invention

| SI No. | Peptide ID | Anti-bacterial activity[A] (MIC in µM) | Hemolysis[B] (MHC in µM) | Cytotoxicity [C] (IC$_{50}$ in µM) | Anti-cancer activity [D] (IC$_{50}$ in µM) |
|---|---|---|---|---|---|
| 3 | SEQ ID NO: 10 | >0.54 | 600 | 248.6 ± 0.1053 | 225.4 ± 0.07138 |
| 4 | SEQ ID NO: 11 | >0.54 | 600 | 233.6 ± 0.1321 | 192.1 ± 0.1353 |
| 5 | SEQ ID NO: 40 | >0.54 | 600 | 314.7 ± 0.1802 | 183.7 ± 0.07222 |
| 6 | SEQ ID NO: 41 | >0.54 | 600 | 309.4 ±0.3877 | 167.0 ± 0.1219 |
| 7 | SEQ ID NO 42 | >0.54 | 600 | 279.3 ± 0.07691 | 204.2 ± 0.1344 |
| 8 | SEQ ID NO 45 | >0.54 | 600 | 167.3 ± 1.390 | 222.3 ± 0.1096 |

[A]Minimum Inhibitory Concentration (MIC) of the peptides measured against *L. monocytogenes*
[B]Maximum Hemolytic Concentration (MHC) of the peptides at which 15-20% hemolysis of human red blood cells is observed
[C] Inhibitory Concentration of the peptides at which 50% cell death is observed (using THP-1 cells)
[D] Inhibitory Concentration of the peptides at which 50% cell (cancerous) death is observed (using HepG2 cells).

Example 2

Cloning and Construction of Recombinant Vector Harboring Expression Cassette DuetEntSAS2 and System Thereof The gene sequence of glycocin SunA/sublancin (Protein ID: WP_009967544.1 GI: 939121)having the polynucleotide sequence as set forth in SEQ ID NO: 61 was PCR amplified from genomic DNA of *B. subtillis* 168 (BEI #NR-607, NIH, Biodefense and Emerging Infections Research Resources Repository (BEI), NIAID, NIH as part of the Human Microbiome Project, Manassas, USA) using primers having sequence as set forth in SEQ ID NO: 25 and SEQ ID NO: 26 and sub-cloned into NcoI and Sap I restriction site of DuetEntSAS1 resulting in construction of recombinant vector having gene cassette DuetEntSAS2. The ligated mixture was transformed into *E. coli* TOP10. The transformants were selected on kanamycin antibiotic agar plate at a final concentration of 50 µg/ml LB medium incubated at 37° C. for 12 h and the transformants harboring DuetEntSAS2 were identified using colony PCR and DNA sequencing.

Thus, the recombinant microbial system comprising recombinant gene cassette DuetEntSAS2 was created having the nucleotide sequence as set forth in SEQ ID NO: 2, which was transformed into a suitable expression host *E. coli* such as *E. coli* KRX or as enlisted in FIG. 1.

The expression, purification, bioactivity and glycosylation status of recombinant sublancin (encoded by polynucleotide sequence as set forth in SEQ ID NO: 2) was checked as described in EXAMPLE 1.

Example 3

Cloning and Construction of Recombinant Vector Harboring Expression Cassette DuetentSAS3 and System Thereof The gene sequences of glycocin GccF/glycocin F (Protein ID: ADV57366.1) having the having the polynucleotide sequence as set forth in SEQ ID NO: 62 was PCR amplified from genomic DNA of *Lactobacillus plantarum* MTCC 2621 (*L. plantarum* MTCC 2621) (The Microbial Type Culture Collection and Gene Bank (MTCC), CSIR-IMTECH, Chandigarh) using primers having sequence as set forth in SEQ ID NO: 27 and SEQ ID NO: 28 and sub-cloned into NcoI and SapI restriction site of DuetEntSAS1 resulting in construction of DuetEntSAS3. The ligated mixture was transformed into *E. coli* TOP10. The transformants were selected on kanamycin antibiotic agar plate at a final concentration of 50 µg/ml LB medium incubated at 37° C. for 12 h and the transformants harboring DuetEntSAS3 was identified using colony PCR and DNA sequencing.

The recombinant expression vector DuetEntSAS3 comprises recombinant gene cassette A having the polynucleotide sequence as set forth in SEQ ID NO: 3, which is transformed into a suitable host *E. coli* such as *E. coli* KRX or as enlisted in FIG. 1.

The expression, purification, bioactivity and glycosylation status of recombinant glycocin F (encoded by polynucleotide sequence as set forth in SEQ ID NO: 3) was checked as described in EXAMPLE 1.

Example 4

Cloning and Construction of Recombinant Vector Harboring Expression Cassette DuetSunSAS2 and System Thereof Custom synthesized nucleotide sequence (GenScript, 860 Centennial Ave., Piscataway, NJ 08854, USA) of the glycosyltransferase (GT) such as SunS(Protein ID: NP_390028, GI: 939123)having the polynucleotide sequence as set forth in SEQ ID NO: 64 was amplified using gene-specific primers having sequences SEQ ID NO: 28 and SEQ ID NO: 29 containing NdeI and XhoI restriction sites. The PCR amplified SunS and the EntSAS1MCHpRSFDuet-1SapI vector were digested with restriction enzymes NdeI and XhoI and the digested fragments were purified. The purified digested insert SunS and vector AS1MCHpRSFDuet-1SapI were subjected to ligation using T4 DNA ligase. Further, the ligation mixture was transformed into *E. coli* TOP 10 host using heat shock method. The transformants were selected on kanamycin resistant agar plate at a final concentration of 50 µg/ml LB medium incubated at 37° C. for 12 h. The transformants carrying SunSAS1MCHpRSFDuet-1SapI construct were identified by gene-specific PCR. The recombinant construct SunSAS1MCHpRSFDuet-1SapI was isolated and the transformants were verified by restriction digestion. Next the gene sequences of glycocin SunA/ sublancin (Protein ID: WP_009967544.1 GI: 939121) having the polynucleotide sequence as set forth in SEQ ID NO: 61 was PCR amplified from genomic DNA of *B. subtillis* 168 (BEI #NR-607, NIH, Biodefense and Emerging Infections Research Resources Repository (BEI), NIAID, NIH as part of the Human Microbiome Project, Manassas, USA) using primers having sequences SEQ ID NO: 25 and SEQ ID NO: 26 and sub-cloned into NcoI and SapI restriction site of SunSMCHpRSFDuet-1SapI (DuetSunS) resulting in construction of a recombinant vector (SunSAS2MCHpRSFDuet-1SapI) harboring gene cassette DuetSunSAS2. The ligated mixture was transformed into *E. coli* TOP10. The transformants were selected on kanamycin antibiotic agar plate at a final concentration of 50 µg/ml LB medium and incubated at 37° C. for 12h and the transformants harboring DuetSunSAS2 was identified using colony PCR and DNA sequencing.

Thus, the recombinant microbial system comprising recombinant gene cassette DuetSunSAS2 was created having the nucleotide sequence as set forth in SEQ ID NO: 4, which was transformed into a suitable host *E. coli* such as *E. coli* KRX or as enlisted in FIG. 1.

The expression, purification, bioactivity and glycosylation status of recombinant sublancin (encoded by polynucleotide sequence as set forth in SEQ ID NO: 4) was checked as described in EXAMPLE 1.

Example 5

Cloning and Construction of Recombinant Vector Harboring Expression Cassette DuetGccAAS3 and System Thereof Custom synthesized nucleotide sequence (GenScript, 860 Centennial Ave., Piscataway, NJ 08854, USA) of the glycosyltransferase (GT) such as GccA (Protein ID: ADV57361) having the polynucleotide sequence as set forth in SEQ ID NO: 65 was amplified using gene-specific primers having sequences SEQ ID NO: 30 and SEQ ID NO: 31 containing NdeI and XhoI restriction sites. The PCR amplified GccA and the EntSAS1MCHpRSFDuet-1SapI (DuetEntSAS1) vector were digested with restriction enzymes NdeI and XhoI and the digested fragments were purified. The purified digested insert GccA and vector AS1MCHpRSFDuet-1SapI were subjected to ligation using T4 DNA ligase. Further, the ligation mixture was transformed into *E. coli* TOP10 host using heat shock method. The transformants were selected on agar plate having kanamycin at a final concentration of 50 µg/ml LB medium and incubated at 37° C. for 12 h. The transformants carrying GccAAS1MCHpRSFDuet-1SapI construct were identified by gene-specific PCR. The recombinant construct GccAAS1MCHpRSFDuet-1SapI was isolated and the transformants were verified by restriction digestion. The gene sequence of glycocin GccF/glycocin F (Protein ID: ADV57366.1) having the polynucleotide sequence as set forth in SEQ ID NO: 62 was PCR amplified from genomic DNA of *L. plantarum* MTCC 2621 (The Microbial Type Culture Collection and Gene Bank (MTCC), CSIR-IMTECH, Chandigarh) using primers having sequences SEQ ID NO: 26 and SEQ ID NO: 27 and sub-cloned into NcoI and SapI restriction site of GccAMCHpRSFDuet-1SapI (DuetGccA) resulting in construction of a recombinant vector (GccAAS3MCHpRSFDuet-1SapI) harboring gene cassette DuetGccAAS3. The ligated mixture was transformed into *E. coli* TOP10. The transformants were selected on kanamycin antibiotic agar plate at a final concentration of 50 µg/ml LB medium incubated at 37° C. for 12 h and the transformants harboring DuetGccAAS3 were identified using colony PCR and DNA sequencing.

Thus, the recombinant microbial system comprising recombinant gene cassette DuetGccAAS3 was created having the nucleotide sequence as set forth in SEQ ID NO: 5, which was transformed into a suitable host *E. coli* such as *E. coli* KRX or as enlisted in FIG. 1.

The expression, purification, bioactivity and glycosylation status of recombinant sublancin (encoded by encoded by polynucleotide sequence as set forth in SEQ ID NO: 5) was checked as described in EXAMPLE 1.

ADVANTAGES OF THE INVENTION

The present invention provides for:
a novel tool for directed evolution and production of glycosylated antimicrobial peptides/glycocins for useful bioactivities like antimicrobial/new age drugs/cosmetics/food preservatives etc;
a general tool to modify miscallaneous peptides/polypeptides (ex. Industrial enzymes) to improve their bioactivity, stability etc. in vivo;
a general tool to enable directed evolution of O- and S-glycosyltransfeases of GT2 family of glycosyltransferases components to develop cell free glycosylation methods;
a novel high throughput assay system for screening of antimicrobial peptides, more particularly glycocins and a tool to produce neo bioactive and or glycoactive glycocins, in vivo;
cheaper, faster, non-enzymatic, one-step method to screen neo-antimicrobial peptides produced in vivo without effecting its bioactivity in vitro;
The present invention is not dependent on inefficient processes like in vitro oxidative folding or use of disulphide creating microbial strain to produce a bioactive variant. The components can be easily transformed in a microbial strain with disulphide making ability. Hence, use of such strains can additionally provide O- or S-diglycosylated neo antimicrobial peptides wherein disulphide bonds shall remain intact, if required for activity;
Unlike chemo-enzymatic in vitro synthesis of glycopeptides, the present invention provides for cost effective microbial production of bioactive glycosylated neoantimicrobial peptides;
The invention is amenable to all popular mutagenesis methods for directed evolution in vivo and methods of generation of mutant libraries of the same;
Further such libraries can have more than one dimensions of variations: A) Glycan B) Sequence of peptide C) Length of peptide that are not completely addressed by existing methods. The present invention provides a system and methods for such activities;
Library generation in microbial expression systems allows comprehensive flexibility in terms of available sequence space for novel sequence design as well as economical construction of large peptides;
The system is amenable to rapid and comprehensive screening of a wide range of glycoactive and or bioactive neoglycopeptides that are expressible in a cellular host upon induction;
This system and method allows for generation of designer neo-glycocins with altered specificities that might have innumerable applications in discovering novel glycosylated AMPs as well as basic insights on structure function and mechanistic aspects of such glycosylated peptides;

The system also offers an advantage of specificity by virtue of involvement of enzymatic glycosylation, in particular S-glycosylation reaction over chemically engineered thioglycosylation in proteins/peptides;

The invention provides optimized system and methods for high yield production of such neo antimicrobial peptides for downstream applications etc. The present invention provides suitable components and acceptor substartes for further amelioration/extension by applicable glycosyltransferase (such PolyST) to develop glycoconjugates (such as Polysylylated products) for various medicament applications.

REFERENCES

1. L. J. Zhang, R. L. Gallo, *Current biology: CB* 26, R14 (Jan. 11, 2016).
2. P. D. Cotter, R. P. Ross, C. Hill, *Nat Rev Microbiol* 11, 95 (February, 2013).
3. G. E. Norris, M. L. Patchett, *Current opinion in structural biology* 40, 112 (October, 2016).
4. S. Biswas, C. V. Garcia De Gonzalo, L. M. Repka, W. A. van der Donk, *ACS chemical biology* 12, 2965 (Dec. 15, 2017).
5. J. Stepper et al., *Febs Lett* 585, 645 (Feb. 18, 2011).
6. S. W. B. b. Zaid Amso a, Sung-Hyun Yang a, Paul W. R. Harris ORCID logoacd, Tom H. Wright ORCID logoa, Claudio D. Navo e, Mark L. Patchett b, Gillian E. Norris bc and Margaret A. Brimble, *Chemical Science,* 1686 (2018).
7. H. Hanchi et al., *J Agr Food Chem* 64, 3584 (May 11, 2016).
8. M. A. Maky et al., *Applied and environmental microbiology* 81, 4819 (July, 2015).
9. R. Nagar, A. Rao, *Glycobiology*, (May 12, 2017).
10. A. B. Ingham, K. W. Sproat, M. L. V. Tizard, R. J. Moore, *J Appl Microbiol* 98, 676 (2005).
11. G. M. Gibbs, B. E. Davidson, A. J. Hillier, *Appl Environ Microb* 70, 3292 (June, 2004).
12. H. Q. Chen et al., *Biotechnol Lett* 34, 359 (February, 2012).
13. A. A. Ollis, S. Zhang, A. C. Fisher, M. P. DeLisa, *Nat Chem Biol* 10, 816 (October, 2014).
14. H. Ren, S. Biswas, S. Ho, W. A. van der Donk, H. Zhao, *ACS chemical biology* 13, 2966.
15. A. Kaunietis, A. Buivydas, D. J. ÄŒitaviÄius, O. P. Kuipers, *Nature communications* 10, 1115.
16. B. Janesch et al., *Glycobiology* 29, 588.
17. T. G. Keys et al., *Metabolic engineering* 44, 293 (November, 2017).
18. M. L. Chikindas, R. Weeks, D. Drider, V. A. Chistyakov, L. M. Dicks, *Current opinion in biotechnology* 49, 23 (February, 2018).
19. R. Ramu et al., *Critical reviews in food science and nutrition,* 0 (Jul. 20, 2015).
20. V. Bali, P. S. Panesar, M. B. Bera, J. F. Kennedy, *Critical reviews in food science and nutrition* 56, 817 (2016).
21. Z. Benmechemene et al., *Recent patents on DNA & gene sequences* 7, 66 (Apr. 1, 2013).

PATENTS

| | U.S. Pat. No.: | | | |
|---|---|---|---|---|
| 1. | U.S. Pat. No.: | US20090074798 | April 2014 | MARKUS AEBI |
| 2. | U.S. Pat. No.: | U.S. Pat. No. 5,643,758A | July 1997 | NEW ENGLAND BIOLABS |
| 3. | U.S. Pat. No.: | US20040142856A1 | September 2007 | SHAWN DEFREES |
| 4. | U.S. Pat. No.: | WO2017093291 Al | June 2017 | MICHAEL L. WETTER |
| 5. | U.S. Pat. No.: | WO2017175239A1 | April 2016 | ALKA RAO |

---

SEQUENCE LISTING

<160> NUMBER OF SEQ ID NOS: 68

<210> SEQ ID NO 1
<211> LENGTH: 2517
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: DuetEntsAS1 : Recombinant gene cassette
      encoding  EntS (Y) and enterocin 96 (X)  design of which is
      described as construct A of the invention

<400> SEQUENCE: 1
ccatgagcaa acgtgattgt aacttgatga aggcgtgttg tgctggacaa gcagtaacat      60
atgctattca tagtcttta aatcgattag gtggagactc tagtgatcca gctggttgta     120
atgatattgt aagaaaatat tgtaaatgca tcacgggaga tgcactagtt gccctacccg     180
agggcgagtc ggtacgcatc gccgacatcg tgccgggtgc gcggcccaac agtgacaacg     240
ccatcgacct gaaagtcctt gaccggcatg gcaatcccgt gctcgccgac cggctgttcc     300
actccggcga gcatccggtg tacacggtgc gtacggtcga aggtctgcgt gtgacgggca     360

```
ccgcgaacca cccgttgttg tgtttggtcg acgtcgccgg ggtgccgacc ctgctgtgga    420
agctgatcga cgaaatcaag ccgggcgatt acgcggtgat tcaacgcagc gcattcagcg    480
tcgactgtgc aggttttgcc cgcgggaaac ccgaatttgc gcccacaacc tacacagtcg    540
gcgtccctgg actggtgcgt ttcttggaag cacaccaccg agacccggac gcccaagcta    600
tcgccgacga gctgaccgac gggcggttct actacgcgaa agtcgccagt gtcaccgacg    660
ccggcgtgca gccggtgtat agccttcgtg tcgacacggc agaccacgcg tttatcacga    720
acgggttcgt cagccacgct actggcctca ccggtctgaa ctcaggcctc acgacaaatc    780
ctggtgtatc cgcttggcag gtcaacacag cttatactgc gggacaattg gtcacatata    840
acggcaagac gtataaatgt ttgcagcccc cacactcctt ggcaggatgg gaaccatcca    900
acgttcctgc cttgtggcag cttcaacatc accatcatca ccactgaaag cttgcggccg    960
cataatgctt aagtcgaaca gaaagtaatc gtattgtaca cggccgcata atcgaaatta   1020
atacgactca ctatagggga attgtgagcg gataacaatt ccccatctta gtatattagt   1080
taagtataag aaggagatat acatatgtat tctgaaaatt ttattgctaa tgactggttt   1140
aatgtagagg tatttaataa aaataagtat actttaacga accaagagaa taaagatgta   1200
acagaattat ggttacaaat tttaaaaggg ctaaagttcc ccaacgaatt aaaggaaact   1260
gtcagttact ctaaaaattt aaaagaatta tctttaaaaa ctcacgcaga gtatctgta   1320
tgtattattg ctaagaatga acaggattca ataagaaaat gtattaatag tatctatgaa   1380
ttttcagatg aaattatatt tattgataca ggatcaattg attcgacaaa aaaaatagta   1440
aaagaaatag caagcgaaaa agtaaaaata tttgattata cttggcaaga tgattttca   1500
gatgcgagaa attattcaat acaaaaagca agtaaagaat ggatattaat tattgatgca   1560
gatgaatatg tatcttcaga tgagcttatc aaattaaggc tcttaataga tatgttagac   1620
aggtttaaat ttaagagattc attaagagtt agttgtgcaa tatatcaatt agataatgtt   1680
atcacacatg gccaaagtcg attatttaga aacaataata aaattaagta ttatggtcta   1740
atacatgaag agttgaggaa caacaaagga ttagatccaa ttttttaacgt tgaaagtgag   1800
attactttt tccatgacgg ttacaaagaa atacttagga aagagaagtg tgaaagaaac   1860
ataaggctac tagctaagat gttagaaaaa gagccagaca atgttagatg ggcatacttg   1920
tattgtagag attcattttc tataaattcc aacattgatt ttgaaaaaat tctacttcca   1980
tttttaataa agaatatgga tgaaagtata tcatgtgaga atatcctact tacaaactat   2040
actcatttaa tcctatttct tattactaag aaatatataa ttgatgggaa aagctcactt   2100
gcaagtaaat gtatagaggt gttagaaaaa atgctaccta actcttctga tgttactttt   2160
tacaaatttt taaataaaca gcatagtttg tatgaacaac aatttgaatt tttaaaagaa   2220
gtaattcaat ttagaaaaaa taatgaatat gatcaatata gccaaatagg gtgtaattta   2280
ttacactatg atttattaat ttcaggatta ctttttgatg ttaagtctta tgattattca   2340
tatcaatact ttttaaaatt agatttagct aactattttt ctgaattaga gattcctgat   2400
gaatacaaaa tgttaataaa taagtatcgg gagaatgaat cactcgagtc tggtaaagaa   2460
accgctgctg cgaaatttga acgccagcac atggactcgt ctactagcgc agcttaa    2517
```

<210> SEQ ID NO 2
<211> LENGTH: 2493
<212> TYPE: DNA
<213> ORGANISM: Artificial Sequence
<220> FEATURE:

<223> OTHER INFORMATION: Synthetic
<220> FEATURE:
<221> NAME/KEY: misc_feature
<223> OTHER INFORMATION: DuetEntsAS2 : Recombinant gene cassette
      encoding EntS (Y) and sublancin (X)  design of which is
      described as construct A of the invention

<400> SEQUENCE: 2

```
ccatggatgg attaggaaaa gctcagtgtg ctgcgttgtg gctacaatgt gctagtggcg      60
gtacaattgg ttgtggtggc ggagctgttg cttgtcaaaa ctatcgtcaa ttctgcagat     120
gctgcatcac gggagatgca ctagttgccc tacccgaggg cgagtcggta cgcatcgccg     180
acatcgtgcc gggtgcgcgg cccaacagtg acaacgccat cgacctgaaa gtccttgacc     240
ggcatggcaa tcccgtgctc gccgaccggc tgttccactc cggcgagcat ccggtgtaca     300
cggtgcgtac ggtcgaaggt ctgcgtgtga cgggcaccgc gaaccacccg ttgttgtgtt     360
tggtcgacgt cgccggggtg ccgacccgtgc tgtggaagct gatcgacgaa atcaagccgg     420
gcgattacgc ggtgattcaa cgcagcgcat tcagcgtcga ctgtgcaggt tttgcccgcg     480
ggaaacccga atttgcgccc acaacctaca cagtcggcgt ccctggactg gtgcgtttct     540
tggaagcaca ccaccgagac ccggacgccc aagctatcgc cgacgagctg accgacgggc     600
ggttctacta cgcgaaagtc gccagtgtca ccgacgccgg cgtgcagccg gtgtatagcc     660
ttcgtgtcga cacggcagac cacgcgttta tcacgaacgg gttcgtcagc cacgctactg     720
gcctcaccgg tctgaactca ggcctcacga caaatcctgg tgtatccgct tggcaggtca     780
acacagctta tactgcggga caattggtca catataacgg caagacgtat aaatgtttgc     840
agccccacac ctccttggca ggatgggaac catccaacgt tcctgccttg tggcagcttc     900
aacatcacca tcatcaccac tgaaagcttg cggccgcata atgcttaagt cgaacagaaa     960
gtaatcgtat tgtacacggc cgcataatcg aaattaatac gactcactat aggggaattg    1020
tgagcggata caattccccc atcttagtat attagttaag tataagaagg atatacat     1080
atgtattctg aaaattttat tgctaatgac tggtttaatg tagaggtatt taataaaaat    1140
aagtatactt taacgaacca agagaataaa gatgtaacag aattatggtt acaaattta    1200
aaagggctaa agttccccaa cgaattaaag gaaactgtca gttactctaa aaatttaaaa    1260
gaattatctt taaaaactca cgcagaagta tctgtatgta ttattgctaa gaatgaacag    1320
gattcaataa gaaaatgtat taatagtatc tatgaatttt cagatgaaat tatatttatt    1380
gatacaggat caattgattc gacaaaaaaa atagtaaaag aaatagcaag cgaaaaagta    1440
aaaatatttg attatacttg gcaagatgat ttttcagatg cgagaaatta ttcaatacaa    1500
aaagcaagta agaatggat attaattatt gatgcagatg aatatgtatc ttcagatgag    1560
cttatcaaat taaggctctt aatagatatg ttagacaggt ttaaatttaa agattcatta    1620
agagttagtt gtgcaatata tcaattagat aatgttatca cacatggcca aagtcgatta    1680
tttagaaaca ataataaaat taagtattat ggtctaatac atgaagagtt gaggaacaac    1740
aaaggattag atccaatttt taacgttgaa agtgagatta cttttttcca tgacggttac    1800
aaagaaatac ttaggaaaga gaagtgtgaa agaaacataa ggctactagc taagatgtta    1860
gaaaagagc cagacaatgt tagatgggca tacttgtatt gtagagattc attttctata    1920
aattccaaca ttgattttga aaaaattcta cttccatttt taataaagaa tatggatgaa    1980
agtatatcat gtgagaatat cctacttaca aactatactc atttaatcct atttcttatt    2040
actaagaaat atataattga tgggaaaagc tcacttgcaa gtaaatgtat agaggtgtta    2100
```

```
gaaaaaatgc tacctaactc ttctgatgtt acttttttaca aattttttaaa taaacagcat    2160 agtttgtatg aacaacaatt tgaatttttta aaagaagtaa ttcaatttag aaaaaataat    2220
gaatatgatc aatatagcca aatagggtgt aatttattac actatgattt attaatttca    2280
ggattacttt ttgatgttaa gtcttatgat tattcatatc aatacttttt aaaattagat    2340
ttagctaact attttttctga attagagatt cctgatgaat acaaaatgtt aataaataag    2400
tatcgggaga atgaatcact cgagtctggt aaagaaaccg ctgctgcgaa atttgaacgc    2460
cagcacatgg actcgtctac tagcgcagct taa                                 2493
```

<210> SEQ ID NO 3
<211> LENGTH: 2512
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: DuetEntsAS3 : Recombinant gene cassette
  encoding EntS (Y) and glycocin F (X) design of which is
  described as construct A of the invention

<400> SEQUENCE: 3

```
ccatggatga aacctgcatg gtgttggtat actttagcaa tgtgtggtgc tggttatgat     60
tcgggaacct gtgattatat gtattcgcat tgttttggta taaagcatca tagtagtggt    120
agtagcagtt atcattgtac ctgcatcacg ggagatgcac tagttgccct acccgagggc    180
gagtcggtac gcatcgccga catcgtgccg ggtgcgcggc caacagtga caacgccatc    240 gacctgaaag tccttgaccg gcatggcaat cccgtgctcg ccgaccggct gttccactcc    300
ggcgagcatc cggtgtacac ggtgcgtacg gtcgaaggtc tgcgtgtgac gggcaccgcg    360
aaccacccgt tgttgtgttt ggtcgacgtc gccggggtgc cgaccctgct gtggaagctg    420
atcgacgaaa tcaagcccgg cgattacgcg gtgattcaac gcagcgcatt cagcgtcgac    480
tgtgcaggtt ttgcccgcgg gaaacccgaa tttgcgccca aacctacac agtcggcgtc     540 cctggactgg tgcgtttctt ggaagcacac caccgagacc cggacgccca agctatcgcc    600
gacgagctga ccgacgggcg gttctactac gcgaaagtcg ccagtgtcac cgacgccggc    660
gtgcagccgg tgtatagcct tcgtgtcgac acggcagacc acgcgtttat cacgaacggg    720
ttcgtcagcc acgctactgg cctcaccggt ctgaactcag gcctcacgac aaatcctggt    780
gtatccgctt ggcaggtcaa cacagcttat actgcgggac aattggtcac atataacggc    840
aagacgtata atgtttgca gccccacacc tccttggcag gatgggaacc atccaacgtt     900
cctgccttgt ggcagcttca acatcaccat catcaccact gaaagcttgc ggccgcataa    960
tgcttaagtc gaacagaaag taatcgtatt gtacacggcc gcataatcga attaatacg    1020 actcactata ggggaattgt gagcggataa caattcccca tcttagtata ttagttaagt   1080
ataagaagga gatatacata tgtattctga aaatttttatt gctaatgact ggtttaatgt   1140
agaggtattt aataaaaata gtatactttt aacgaaccaa gagaataaag atgtaacaga   1200
attatggtta caaattttaa aagggctaaa gttccccaac gaattaaagg aaactgtcag   1260
ttactctaaa aatttaaaag aattatcttt aaaaactcac gcagaagtat ctgtatgtat   1320
tattgctaag aatgaacagg attcaataag aaaatgtatt aatagtatct atgaattttc   1380
agatgaaatt atatttattg atacaggatc aattgattcg acaaaaaaaaa tagtaaaaga   1440 aatagcaagc gaaaaagtaa aaatatttga ttatacttgg caagatgatt tttcagatgc   1500
```

```
gagaaattat tcaatacaaa aagcaagtaa agaatggata ttaattattg atgcagatga    1560
atatgtatct tcagatgagc ttatcaaatt aaggctctta atagatatgt tagacaggtt    1620
taaatttaaa gattcattaa gagttagttg tgcaatatat caattagata atgttatcac    1680
acatggccaa agtcgattat ttagaaacaa taataaaatt aagtattatg gtctaataca    1740
tgaagagttg aggaacaaca aaggattaga tccaattttt aacgttgaaa gtgagattac    1800
ttttttccat gacggttaca aagaaatact taggaaagag aagtgtgaaa gaaacataag    1860
gctactagct aagatgttag aaaaagagcc agacaatgtt agatgggcat acttgtattg    1920
tagagattca ttttctataa attccaacat tgattttgaa aaaattctac ttccatttt    1980 aataaagaat atggatgaaa gtatatcatg tgagaatatc ctacttacaa actatactca    2040
tttaatccta tttcttatta ctaagaaata tataattgat gggaaaagct cacttgcaag    2100
taaatgtata gaggtgttag aaaaaatgct acctaactct tctgatgtta cttttttacaa   2160 attttttaaat aaacagcata gtttgtatga acaacaattt gaattttaa aagaagtaat     2220 tcaatttaga aaaaataatg aatatgatca atatagccaa ataggtgta atttattaca       2280 ctatgattta ttaatttcag gattactttt tgatgttaag tcttatgatt attcatatca    2340
atacttttta aaattagatt tagctaacta tttttctgaa ttagagattc ctgatgaata    2400
caaaatgtta ataaataagt atcgggagaa tgaatcactc gagtctggta agaaaccgc     2460 tgctgcgaaa tttgaacgcc agcacatgga ctcgtctact agcgcagctt aa             2512
```

<210> SEQ ID NO 4
<211> LENGTH: 2421
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: DuetSunSAS2 : Recombinant gene cassette
      encoding SunS (Y) and sublancin (X) design of which is
      described as construct A of the invention

<400> SEQUENCE: 4

```
ccatggatgg attaggaaaa gctcagtgtg ctgcgttgtg ctacaatgt gctagtggcg      60 gtacaattgg ttgtggtggc ggagctgttg cttgtcaaaa ctatcgtcaa ttctgcagat    120
gctgcatcac gggagatgca ctagttgccc tacccgaggg cgagtcggta cgcatcgccg    180
acatcgtgcc gggtgcgcgg cccaacagtg acaacgccat cgacctgaaa gtccttgacc    240
ggcatggcaa tcccgtgctc gccgaccggc tgttccactc cggcgagcat ccggtgtaca    300
cggtgcgtac ggtcgaaggt ctgcgtgtga cgggcaccgc gaaccacccg ttgttgtgtt    360
tggtcgacgt cgccggggtg ccgaccctgc tgtggaagct gatcgacgaa atcaagccgg    420
gcgattacgc ggtgattcaa cgcagcgcat tcagcgtcga ctgtgcaggt tttgcccgcg    480
ggaaacccga atttgcgccc acaacctaca cagtcggcgt ccctggactg gtgcgtttct    540
tggaagcaca ccaccgagac ccggacgccc aagctatcgc cgacgagctg accgacgggc    600
ggttctacta cgcgaaagtc gccagtgtca ccgacgccgg cgtgcagccg gtgtatagcc    660
ttcgtgtcga cacggcagac cacgcgttta tcacgaacgg gttcgtcagc cacgctactg    720
gcctcaccgg tctgaactca ggcctcacga caaatcctgg tgtatccgct ggcaggtca   780 acacagctta tactgcggga caattggtca catataacgg caagacgtat aaatgtttgc    840
agccccacac ctccttggca ggatgggaac catccaacgt tcctgccttg tggcagcttc    900
```

```
aacatcacca tcatcaccac tgaaagcttg cggccgcata atgcttaagt cgaacagaaa     960
gtaatcgtat tgtacacggc cgcataatcg aaattaatac gactcactat agggaattg     1020 tgagcggata acaattcccc atcttagtat attagttaag tataagaagg agatatacat    1080
atgaaactga gtgatattta tttggaatta agaaaggct atgccgattc tttattgtat     1140
tcagatttgt cattgttggt taatataatg gaatatgaaa aagatattga tgtgatgtca    1200
attcaatctt tggttgcagg ttatgaaaaa tcagatactc ctacaataac atgcggtatt    1260
atagtttata acgaaagcaa gagaattaaa aagtgtttaa atagtgttaa agatgatttt    1320
aacgagatta ttgttctaga ttcatactcc actgatgata ccgttgatat tattaaatgt    1380
gattttcctg atgttgaaat taaatatgaa aagtggaaga atgatttttc ctatgctaga    1440
aataaaatta tagagtatgc tacttccgaa tggatttatt ttattgatgc agataattta    1500
tactctaaag aaaacaaagg gaaaatagct aaagtagcta gagttttaga gttttttct    1560 attgattgtg tagttagtcc atatatgaaa gaatatactg gacatctata ttctgataca    1620
cgaagaatgt ttcggctcaa tggtaaagtt aaatttcatg ggaaagtgca tgaagaacct   1680
atgaattata atcatagtct accttttaat ttcattgtga acctaaggt ttaccataat     1740 ggatataatc cttcagagaa taatataaaa tcaaaaacac gaaggaatat aaatctcaca    1800
gaagaaatgt taagattgga gcccgaaaac ccaaaatggt tattctttt cggcagagaa    1860 ctacattttac ttgataaaga tgaagaagca attgattatc tgaaaaaatc aataaacaac  1920
tataaaaaat ttaatgatca aagacatttt atagatgctt tagtgctatt atgtactta    1980 ttattgcaga gaaataatta tgttgactta actttatatt tggatatatt ggaaactgaa   2040
tatccaagat gtgttgatgt tgattacttt agatctgcaa ttttgttagt agatatgcaa   2100
aataaactta cttctttaag caatatgatt gatgaagctc ttacagacga gagatacagt   2160
gctataaata caacaaaaga tcactttaaa agaattttaa taagccttaa tattcaactc   2220
gaaaattggg aaagagtaaa agaaatatca ggggaaatta aaaatgataa tatgaaaaaa    2280
gaaattaaac aatatcttgc caactcactc cacaatattg aacacgtcct gaaaggaatt   2340
gaagtactcg agtctggtaa agaaaccgct gctgcgaaat ttgaacgcca gcacatggac    2400
tcgtctacta gcgcagctta a                                              2421

<210> SEQ ID NO 5
<211> LENGTH: 2440
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: DuetGccAAS3 : Recombinant gene cassette
      encoding GccA (Y) and glycocin F(X)  design of which is described
      as construct A of the invention

<400> SEQUENCE: 5
ccatggatga aacctgcatg gtgttggtat actttagcaa tgtgtggtgc tggttatgat     60
tcgggaacct gtgattatat gtattcgcat tgttttggta taaagcatca tagtagtggt    120
agtagcagtt atcattgtac ctgcatcacg ggagatgcac tagttgccct accgagggc    180 gagtcggtac gcatcgccga catcgtgccg ggtgcgcggc ccaacagtga caacgccatc    240
gacctgaaag tccttgaccg gcatggcaat cccgtgctcg ccgaccggct gttccactcc    300
ggcgagcatc cggtgtacac ggtgcgtacg gtcgaaggtc tgcgtgtgac gggcaccgcg    360
```

```
aaccacccgt tgttgtgttt ggtcgacgtc gccggggtgc cgaccctgct gtggaagctg      420
atcgacgaaa tcaagccggg cgattacgcg gtgattcaac gcagcgcatt cagcgtcgac      480
tgtgcaggtt ttgcccgcgg gaaacccgaa tttgcgccca aacctacac agtcggcgtc       540 cctggactgg tgcgtttctt ggaagcacac caccgagacc cggacgccca agctatcgcc      600
gacgagctga ccgacgggcg gttctactac gcgaaagtcg ccagtgtcac cgacgccggc      660
gtgcagccgg tgtatagcct tcgtgtcgac acggcagacc acgcgtttat cacgaacggg      720
ttcgtcagcc acgctactgg cctcaccggt ctgaactcag gcctcacgac aaatcctggt      780
gtatccgctt ggcaggtcaa cacagcttat actgcgggac aattggtcac atataacggc      840
aagacgtata atgtttgca gccccacacc tccttggcag gatgggaacc atccaacgtt       900
cctgccttgt ggcagcttca acatcaccat catcaccact gaaagcttgc ggccgcataa      960
tgcttaagtc gaacagaaag taatcgtatt gtacacggcc gcataatcga aattaatacg      1020
actcactata ggggaattgt gagcggataa caattcccca tcttagtata ttagttaagt      1080
ataagaagga gatatacata tgaaaaatcg ccaaaatgaa attgactcct acctgaatct      1140
gcatctgcgt ccggtccata aatccttcga cttcggcaac ctgaccaaca ttgatcagtt      1200
tcgtcatcac atctatgtta gttacattgt catctgcaaa aactcccagg caacgattga      1260
acgctgtgtg aatagtatcg ctcaaaacat ggaaatggc gatgaactga ttgttctgga      1320
taccggtagc acggacgaaa ccgtgcatct ggtgaagaaa acatgccgc aggcgaaaat      1380 cagcgtgacc aactggaaaa acgatttctc tgaagttcgt aacaaagcac tgaaactggc      1440
tagtaaagat tgggtcttct atgtggattc cgacgaatgg ctggacgtcg atgacggcgc      1500
gcagctgaag aaaattctgt tcaaagttca agccaaaaac ttcaaattcg tcatcaatcc      1560
gacgttcagc gatcactctg ccagatttta tcaaaccgtt ggtcgcatct cccgaaaaa      1620 atctagcttt cattactacg ccaaaattca cgaagaagtc cgtaaagaag atcagaaact      1680
gggctacgac gtgcgccatt ttgcgtgcga tgacattatc ctgtatcacg atggttacga      1740
caaagaagtg ctgcgtgata aagacaaaat taaacgtaac atccgcctgc tgcaggaaat      1800
gacgtgtgaa gaaccgcaaa atgcgcgttg gccgtttctg ctggcccgcg atggtttcga      1860
cgttctgccg caggataaac tgaaacaact ggtcaaacgc accctggatc tggtggcgtc      1920
agactcgctg caggaaaaat atagcccgtt cgccaaaaaa ctgctgggcc gtattctgct      1980
gcgcgaaggt aaaaccacgc aggcagtgct gtctttaaa gatgttctgc aaatcaccgg      2040
cggtgaagat tcagacgcta tctactacat cgaatcgttc aaaatcaacg aaattatcgc      2100
ggaagccaaa agcatcgaag tgaaaatgct gcgttacctg aacaaacata aaggcatgat      2160
cgatgttaac agtgacatct ccggtaatta ttaccacatt gcacaggtca tcctggaatg      2220
cgatattatc tcagctaact actcgcacct gtttccgctg attagcgaaa tcccgaaaaa      2280
tttctctggc gatattaaaa gttccgtcaa atctgcggtc aaactgtatt ccaaactgca      2340
aggtgatagt aaaaatgaaa acaatctcga gtctggtaaa gaaaccgctg ctgcgaaatt      2400
tgaacgccag cacatggact cgtctactag cgcagcttaa                          2440
```

<210> SEQ ID NO 6
<211> LENGTH: 314
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: Acceptor substrate 1 (AS1) : Amino acid
sequence of enterocin 96 (X) in fusion with cleavable MCH tag,
design of which is described as construct A and B of the invention

<400> SEQUENCE: 6

```
Met Ser Lys Arg Asp Cys Asn Leu Met Lys Ala Cys Cys Ala Gly Gln
1               5                   10                  15

Ala Val Thr Tyr Ala Ile His Ser Leu Leu Asn Arg Leu Gly Gly Asp
            20                  25                  30

Ser Ser Asp Pro Ala Gly Cys Asn Asp Ile Val Arg Lys Tyr Cys Lys
        35                  40                  45

Cys Ile Thr Gly Asp Ala Leu Val Ala Leu Pro Glu Gly Glu Ser Val
50                  55                  60

Arg Ile Ala Asp Ile Val Pro Gly Ala Arg Pro Asn Ser Asp Asn Ala
65                  70                  75                  80

Ile Asp Leu Lys Val Leu Asp Arg His Gly Asn Pro Val Leu Ala Asp
            85                  90                  95

Arg Leu Phe His Ser Gly Glu His Pro Val Tyr Thr Val Arg Thr Val
        100                 105                 110

Glu Gly Leu Arg Val Thr Gly Thr Ala Asn His Pro Leu Leu Cys Leu
    115                 120                 125

Val Asp Val Ala Gly Val Pro Thr Leu Leu Trp Lys Leu Ile Asp Glu
130                 135                 140

Ile Lys Pro Gly Asp Tyr Ala Val Ile Gln Arg Ser Ala Phe Ser Val
145                 150                 155                 160

Asp Cys Ala Gly Phe Ala Arg Gly Lys Pro Glu Phe Ala Pro Thr Thr
            165                 170                 175

Tyr Thr Val Gly Val Pro Gly Leu Val Arg Phe Leu Glu Ala His His
        180                 185                 190

Arg Asp Pro Asp Ala Gln Ala Ile Ala Asp Glu Leu Thr Asp Gly Arg
    195                 200                 205

Phe Tyr Tyr Ala Lys Val Ala Ser Val Thr Asp Ala Gly Val Gln Pro
210                 215                 220

Val Tyr Ser Leu Arg Val Asp Thr Ala Asp His Ala Phe Ile Thr Asn
225                 230                 235                 240

Gly Phe Val Ser His Ala Thr Gly Leu Thr Gly Leu Asn Ser Gly Leu
            245                 250                 255

Thr Thr Asn Pro Gly Val Ser Ala Trp Gln Val Asn Thr Ala Tyr Thr
        260                 265                 270

Ala Gly Gln Leu Val Thr Tyr Asn Gly Lys Thr Tyr Lys Cys Leu Gln
    275                 280                 285

Pro His Thr Ser Leu Ala Gly Trp Glu Pro Ser Asn Val Pro Ala Leu
290                 295                 300

Trp Gln Leu Gln His His His His His
305                 310
```

<210> SEQ ID NO 7
<211> LENGTH: 306
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: Acceptor substrate 2 (AS2) : Amino acid
sequence of sublancin (X) in fusion with cleavable MCH tag,
design of which is described as construct A and B of the invention

<400> SEQUENCE: 7

Met Asp Gly Leu Gly Lys Ala Gln Cys Ala Ala Leu Trp Leu Gln Cys
1               5                   10                  15

Ala Ser Gly Gly Thr Ile Gly Cys Gly Gly Ala Val Ala Cys Gln
            20                  25                  30

Asn Tyr Arg Gln Phe Cys Arg Cys Ile Thr Gly Asp Ala Leu Val
        35                  40                  45

Ala Leu Pro Glu Gly Glu Ser Val Arg Ile Ala Asp Ile Val Pro Gly
    50                  55                  60

Ala Arg Pro Asn Ser Asp Asn Ala Ile Asp Leu Lys Val Leu Asp Arg
65                  70                  75                  80

His Gly Asn Pro Val Leu Ala Asp Arg Leu Phe His Ser Gly Glu His
                85                  90                  95

Pro Val Tyr Thr Val Arg Thr Val Glu Gly Leu Arg Val Thr Gly Thr
            100                 105                 110

Ala Asn His Pro Leu Leu Cys Leu Val Asp Val Ala Gly Val Pro Thr
        115                 120                 125

Leu Leu Trp Lys Leu Ile Asp Glu Ile Lys Pro Gly Asp Tyr Ala Val
130                 135                 140

Ile Gln Arg Ser Ala Phe Ser Val Asp Cys Ala Gly Phe Ala Arg Gly
145                 150                 155                 160

Lys Pro Glu Phe Ala Pro Thr Thr Tyr Thr Val Gly Val Pro Gly Leu
                165                 170                 175

Val Arg Phe Leu Glu Ala His His Arg Asp Pro Asp Ala Gln Ala Ile
            180                 185                 190

Ala Asp Glu Leu Thr Asp Gly Arg Phe Tyr Tyr Ala Lys Val Ala Ser
        195                 200                 205

Val Thr Asp Ala Gly Val Gln Pro Val Tyr Ser Leu Arg Val Asp Thr
210                 215                 220

Ala Asp His Ala Phe Ile Thr Asn Gly Phe Val Ser His Ala Thr Gly
225                 230                 235                 240

Leu Thr Gly Leu Asn Ser Gly Leu Thr Thr Asn Pro Gly Val Ser Ala
                245                 250                 255

Trp Gln Val Asn Thr Ala Tyr Thr Ala Gly Gln Leu Val Thr Tyr Asn
            260                 265                 270

Gly Lys Thr Tyr Lys Cys Leu Gln Pro His Thr Ser Leu Ala Gly Trp
        275                 280                 285

Glu Pro Ser Asn Val Pro Ala Leu Trp Gln Leu Gln His His His His
    290                 295                 300

His His
305

<210> SEQ ID NO 8
<211> LENGTH: 311
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: Acceptor substrate 3 (AS3) : Amino acid
      sequence of  glycocin F (X) in fusion with cleavable MCH tag ,
      design of which is described as construct A and B of the invention

<400> SEQUENCE: 8

Met Lys Pro Ala Trp Cys Trp Tyr Thr Leu Ala Met Cys Gly Ala Gly
1               5                   10                  15

Tyr Asp Ser Gly Thr Cys Asp Tyr Met Tyr Ser His Cys Phe Gly Ile
                20                  25                  30

Lys His His Ser Ser Gly Ser Ser Tyr His Cys Thr Cys Ile Thr
            35                  40                  45

Gly Asp Ala Leu Val Ala Leu Pro Glu Gly Glu Ser Val Arg Ile Ala
50                  55                  60

Asp Ile Val Pro Gly Ala Arg Pro Asn Ser Asp Asn Ala Ile Asp Leu
65                  70                  75                  80

Lys Val Leu Asp Arg His Gly Asn Pro Val Leu Ala Asp Arg Leu Phe
                85                  90                  95

His Ser Gly Glu His Pro Val Tyr Thr Val Arg Thr Val Glu Gly Leu
            100                 105                 110

Arg Val Thr Gly Thr Ala Asn His Pro Leu Leu Cys Leu Val Asp Val
        115                 120                 125

Ala Gly Val Pro Thr Leu Leu Trp Lys Leu Ile Asp Glu Ile Lys Pro
130                 135                 140

Gly Asp Tyr Ala Val Ile Gln Arg Ser Ala Phe Ser Val Asp Cys Ala
145                 150                 155                 160

Gly Phe Ala Arg Gly Lys Pro Glu Phe Ala Pro Thr Thr Tyr Thr Val
                165                 170                 175

Gly Val Pro Gly Leu Val Arg Phe Leu Glu Ala His His Arg Asp Pro
            180                 185                 190

Asp Ala Gln Ala Ile Ala Asp Glu Leu Thr Asp Gly Arg Phe Tyr Tyr
        195                 200                 205

Ala Lys Val Ala Ser Val Thr Asp Ala Gly Val Gln Pro Val Tyr Ser
210                 215                 220

Leu Arg Val Asp Thr Ala Asp His Ala Phe Ile Thr Asn Gly Phe Val
225                 230                 235                 240

Ser His Ala Thr Gly Leu Thr Gly Leu Asn Ser Gly Leu Thr Thr Asn
                245                 250                 255

Pro Gly Val Ser Ala Trp Gln Val Asn Thr Ala Tyr Thr Ala Gly Gln
            260                 265                 270

Leu Val Thr Tyr Asn Gly Lys Thr Tyr Lys Cys Leu Gln Pro His Thr
        275                 280                 285

Ser Leu Ala Gly Trp Glu Pro Ser Asn Val Pro Ala Leu Trp Gln Leu
290                 295                 300

Gln His His His His His
305                 310

<210> SEQ ID NO 9
<211> LENGTH: 48
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: Enetrocin 96 : Amino acid sequence of enetrocin
      96
<220> FEATURE:
<221> NAME/KEY: MISC_FEATURE
<223> OTHER INFORMATION: Enterocin 96 : Amino acid sequence of enterocin
      96

<400> SEQUENCE: 9

Met Ser Lys Arg Asp Cys Asn Leu Met Lys Ala Cys Cys Ala Gly Gln
1               5                   10                  15

```
Ala Val Thr Tyr Ala Ile His Ser Leu Leu Asn Arg Leu Gly Gly Asp
            20                  25                  30

Ser Ser Asp Pro Ala Gly Cys Asn Asp Ile Val Arg Lys Tyr Cys Lys
        35                  40                  45
```

<210> SEQ ID NO 10
<211> LENGTH: 48
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: Glycocin 1 : Amino acid sequence of neo-
      glycocin produced using the recombinant microbial system of the
      invention

<400> SEQUENCE: 10

```
Met Ser Lys Arg Asp Cys Asn Leu Met Lys Ala Thr Cys Ala Gly Gln
1               5                   10                  15

Ala Val Thr Tyr Ala Ile His Ser Leu Leu Asn Arg Leu Gly Gly Asp
            20                  25                  30

Ser Ser Asp Pro Ala Gly Cys Asn Asp Ile Val Arg Lys Tyr Cys Lys
        35                  40                  45
```

<210> SEQ ID NO 11
<211> LENGTH: 56
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: Glycocin 2 : Amino acid sequence of neo-
      glycocin produced using the recombinant microbial system of the
      invention

<400> SEQUENCE: 11

```
Met Ala Ser Lys Tyr Tyr Gly Asn Gly Val Lys Arg Asp Cys Asn Leu
1               5                   10                  15

Met Lys Ala Cys Cys Ala Gly Gln Ala Val Thr Tyr Ala Ile His Ser
            20                  25                  30

Leu Leu Asn Arg Leu Gly Gly Asp Ser Ser Asp Pro Ala Gly Cys Asn
        35                  40                  45

Asp Ile Val Arg Lys Tyr Cys Lys
    50                  55
```

<210> SEQ ID NO 12
<211> LENGTH: 38
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer

<400> SEQUENCE: 12
caaataggca tgcagcgcag atccgcttcc tcgctcac                         38

<210> SEQ ID NO 13
<211> LENGTH: 30
<212> TYPE: DNA
<213> ORGANISM: Artificial Sequence
<220> FEATURE:
<223> OTHER INFORMATION: Synthetic

```
<220> FEATURE:
<221> NAME/KEY: misc_feature
<223> OTHER INFORMATION: Primer

<400> SEQUENCE: 13
cgcggcatat gtattctgaa aattttattg                                      30

<210> SEQ ID NO 14
<211> LENGTH: 29
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer

<400> SEQUENCE: 14
aatactcgag tgattcattc tcccgatac                                       29

<210> SEQ ID NO 15
<211> LENGTH: 34
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer

<400> SEQUENCE: 15
gatcccatgg atgagcaaac gtgattgtaa cttg                                 34

<210> SEQ ID NO 16
<211> LENGTH: 26
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer

<400> SEQUENCE: 16
ctgcggatcc tacaatattt tcttac                                          26

<210> SEQ ID NO 17
<211> LENGTH: 36
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer

<400> SEQUENCE: 17
ggtgtggctc ttccgcattt acaatatttt cttaca                               36

<210> SEQ ID NO 18
<211> LENGTH: 32
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer
```

<400> SEQUENCE: 18
gactgggatc cgctcttcct gcatcacggg ag                                32

<210> SEQ ID NO 19
<211> LENGTH: 34
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer

<400> SEQUENCE: 19
ctgagaagct tcattgaag ctgccacaag gcag                               34

<210> SEQ ID NO 20
<211> LENGTH: 49
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer

<400> SEQUENCE: 20
ggtgaagctt tcagtggtga tgatggtgat gttgaagctg ccacaaggc              49

<210> SEQ ID NO 21
<211> LENGTH: 32
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer

<400> SEQUENCE: 21
ggtggtgcta gcaaacgtga ttgtaacttg at                                32

<210> SEQ ID NO 22
<211> LENGTH: 49
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer

<400> SEQUENCE: 22
ggtgctgcag tcagtggtga tgatggtgat gttgaagctg ccacaaggc              49

<210> SEQ ID NO 23
<211> LENGTH: 54
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer

<400> SEQUENCE: 23
ggtgctgcag tcagtgatgg tggtgatgat ggtgatgttg aagctgccac aagg        54

<210> SEQ ID NO 24
<211> LENGTH: 34
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer

<400> SEQUENCE: 24
ggtgccatgg atggattagg aaaagctcag tgtg        34

<210> SEQ ID NO 25
<211> LENGTH: 34
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer

<400> SEQUENCE: 25
ggtggctctt cgcatctgca gaattgacga tagt        34

<210> SEQ ID NO 26
<211> LENGTH: 27
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer

<400> SEQUENCE: 26
ggtgccatgg atgaaacctg catggtg        27

<210> SEQ ID NO 27
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer

<400> SEQUENCE: 27
ggtggctctt cggtacaatg ataactgcta ctaccactac        40

<210> SEQ ID NO 28
<211> LENGTH: 32
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer

<400> SEQUENCE: 28
ggtccatatg aaactgagtg atatttattt gg        32

<210> SEQ ID NO 29
<211> LENGTH: 29
<212> TYPE: DNA

```
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer

<400> SEQUENCE: 29
ggtcctcgag tacttcaatt cctttcagg                                    29

<210> SEQ ID NO 30
<211> LENGTH: 32
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer

<400> SEQUENCE: 30
ggtccatatg aaaaatcgcc aaaatgaaat tg                                32

<210> SEQ ID NO 31
<211> LENGTH: 34
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer

<400> SEQUENCE: 31
ggtcctcgag attgttttca tttttactat cacc                              34

<210> SEQ ID NO 32
<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer

<400> SEQUENCE: 32
atgtattctg aaaatttat tgctaatgac tgg                                33

<210> SEQ ID NO 33
<211> LENGTH: 31
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer

<400> SEQUENCE: 33
tgattcattc tcccgatact tatttattaa c                                 31

<210> SEQ ID NO 34
<211> LENGTH: 32
<212> TYPE: DNA
<213> ORGANISM: Artificial Sequence
<220> FEATURE:
<223> OTHER INFORMATION: Synthetic
<220> FEATURE:
```

<221> NAME/KEY: misc_feature
<223> OTHER INFORMATION: Primer

<400> SEQUENCE: 34
atgagcaaac gtgattgtaa cttgatgaag gc                                      32

<210> SEQ ID NO 35
<211> LENGTH: 36
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer

<400> SEQUENCE: 35
tttacaatat tttcttacaa tatcattaca accagc                                  36

<210> SEQ ID NO 36
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer

<400> SEQUENCE: 36
ttgtaacttg atgaaggcga cttgtgctgg acaagcagta                              40

<210> SEQ ID NO 37
<211> LENGTH: 60
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer

<400> SEQUENCE: 37
cggtgctagc aaatactacg gtaacggtgt aaaacgtgat tgtaacttga tgaaggcgtg        60

<210> SEQ ID NO 38
<211> LENGTH: 52
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer

<400> SEQUENCE: 38
ggtggtgctc ttccgcattt acatctccaa tcactagagt ctccacctaa tc                52

<210> SEQ ID NO 39
<211> LENGTH: 34
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer

<400> SEQUENCE: 39
ggtggtgcta gcatgaaggc gtgttgtgct ggac          34

<210> SEQ ID NO 40
<211> LENGTH: 49
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: Variant of Enterocin 96

<400> SEQUENCE: 40

Met Ala Ser Lys Arg Asp Cys Asn Leu Met Lys Ala Cys Cys Ala Gly
1               5                   10                  15

Gln Ala Val Thr Tyr Ala Ile His Ser Leu Leu Asn Arg Leu Gly Gly
            20                  25                  30

Asp Cys Ser Asp Pro Ala Gly Cys Asn Asp Ile Val Arg Lys Tyr Cys
        35                  40                  45

Lys

<210> SEQ ID NO 41
<211> LENGTH: 42
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: Variant of Enteriocin 96

<400> SEQUENCE: 41

Met Ala Ser Lys Ala Cys Cys Ala Gly Gln Ala Val Thr Tyr Ala Ile
1               5                   10                  15

His Ser Leu Leu Asn Arg Leu Gly Gly Asp Ser Ser Asp Pro Ala Gly
            20                  25                  30

Cys Asn Asp Ile Val Arg Lys Tyr Cys Lys
        35                  40

<210> SEQ ID NO 42
<211> LENGTH: 49
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: Variant of Enterocin 96

<400> SEQUENCE: 42

Met Ala Ser Lys Arg Asp Cys Asn Leu Met Lys Ala Cys Cys Ala Gly
1               5                   10                  15

Gln Ala Val Thr Tyr Ala Ile His Ser Leu Leu Asn Arg Leu Gly Gly
            20                  25                  30

Asp Ser Ser Gly Pro Ala Gly Cys Asn Asp Ile Val Arg Lys Tyr Cys
        35                  40                  45

Lys

<210> SEQ ID NO 43
<211> LENGTH: 49
<212> TYPE: PRT

```
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: Variant of Enterocin 96

<400> SEQUENCE: 43
```

Met Ala Ser Lys Arg Asp Cys Asn Leu Met Lys Ala Cys Cys Ala Gly
1               5                   10                  15

Gln Ala Val Thr Tyr Ala Ile Gln Ser Leu Leu Asn Arg Leu Gly Gly
            20                  25                  30

Asp Ser Ser Asp Pro Ala Gly Cys Asn Asp Ile Val Arg Lys Tyr Cys
        35                  40                  45

Lys

```
<210> SEQ ID NO 44
<211> LENGTH: 49
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: Variant of Enterocin 96

<400> SEQUENCE: 44
```

Met Ala Ser Lys Arg Asp Cys Asn Leu Met Lys Ala Arg Cys Ala Gly
1               5                   10                  15

Gln Ala Val Thr Tyr Ala Ile His Ser Leu Leu Asn Arg Leu Gly Gly
            20                  25                  30

Asp Ser Ser Asp Pro Ala Gly Cys Asn Asp Ile Val Arg Lys Tyr Cys
        35                  40                  45

Lys

```
<210> SEQ ID NO 45
<211> LENGTH: 49
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: Variant of Enterocin 96

<400> SEQUENCE: 45
```

Met Ala Ser Lys Arg Asp Cys Asn Leu Met Lys Ala Cys Cys Ala Glu
1               5                   10                  15

Gln Ala Val Thr Tyr Ala Ile Gln Ser Leu Leu Asn Arg Leu Gly Gly
            20                  25                  30

Asp Ser Ser Asp Pro Ala Gly Cys Asn Asp Ile Val Arg Lys Tyr Cys
        35                  40                  45

Lys

```
<210> SEQ ID NO 46
<211> LENGTH: 49
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: Variant of Enterocin 96
```

<400> SEQUENCE: 46

Met Ala Ser Lys Arg Asp Cys Asn Leu Met Lys Ala Cys Cys Ala Glu
1               5                   10                  15

Gln Ala Val Thr Tyr Ala Ile His Ser Leu Leu Asn Arg Leu Gly Gly
            20                  25                  30

Asp Ser Ser Asp Pro Ala Gly Cys Asn Asp Ile Val Arg Lys Tyr Cys
        35                  40                  45

Lys

<210> SEQ ID NO 47
<211> LENGTH: 49
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: Variant of Enterocin 96

<400> SEQUENCE: 47

Met Ala Ser Lys Arg Asp Cys Asn Leu Met Lys Ala Cys Cys Ala Gly
1               5                   10                  15

Gln Ala Val Thr Tyr Ala Ile His Ser Leu Leu Asn Arg Leu Gly Gly
            20                  25                  30

Asp Ser Ser Val Pro Ala Gly Cys Asn Asp Ile Val Arg Lys Tyr Cys
        35                  40                  45

Lys

<210> SEQ ID NO 48
<211> LENGTH: 49
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: Variant of Enterocin 96

<400> SEQUENCE: 48

Met Ala Ser Lys Arg Asp Cys Asn Leu Met Lys Ala Cys Cys Ala Gly
1               5                   10                  15

Gln Ala Val Thr Tyr Ala Ile His Ser Leu Leu Tyr Arg Leu Gly Gly
            20                  25                  30

Asp Ser Ser Asp Pro Ala Gly Cys Asn Asp Ile Val Arg Lys Tyr Cys
        35                  40                  45

Lys

<210> SEQ ID NO 49
<211> LENGTH: 49
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: Variant of Enterocin 96

<400> SEQUENCE: 49

Met Ala Ser Lys Arg Asp Cys Asn Leu Met Lys Ala Cys Cys Ala Gly
1               5                   10                  15

His Ala Val Thr Tyr Ala Ile His Ser Leu Leu Lys Arg Leu Gly Gly
            20                  25                  30

Asp Ser Ser Asp Pro Ala Gly Cys Asn Asp Ile Val Arg Lys Tyr Cys
            35                  40                  45

Lys

<210> SEQ ID NO 50
<211> LENGTH: 49
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: Variant of Enterocin 96

<400> SEQUENCE: 50

Met Ala Ser Lys Arg Asp Cys Asn Leu Met Lys Ala Cys Cys Ala Gly
1               5                   10                  15

Gln Ala Val Thr Tyr Ala Ile His Ser Leu Leu Asn Arg Leu Gly Gly
            20                  25                  30

Asp Ser Ser Asp Pro Ala Gly Ser Asn Asp Ile Val Arg Lys Tyr Cys
            35                  40                  45

Lys

<210> SEQ ID NO 51
<211> LENGTH: 49
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: Variant of Enterocin 96

<400> SEQUENCE: 51

Met Ala Ser Lys His Asp Cys Asn Leu Met Lys Ala Cys Cys Ala Gly
1               5                   10                  15

Gln Ala Val Thr Tyr Ala Ile His Ser Leu Leu Asn Arg Leu Gly Gly
            20                  25                  30

Asp Ser Ser Asp Pro Ala Gly Cys Asn Asp Ile Val Arg Lys Tyr Cys
            35                  40                  45

Lys

<210> SEQ ID NO 52
<211> LENGTH: 49
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: Variant of Enterocin 96

<400> SEQUENCE: 52

Met Ala Ser Lys Arg Asp Cys Asn Leu Met Lys Ala Cys Cys Ala Gly
1               5                   10                  15

Gln Ala Val Thr Tyr Gly Ile His Ser Leu Leu Asn Arg Leu Gly Gly
            20                  25                  30

Asp Ser Ser Asp Pro Ala Gly Cys Asn Asp Ile Val Arg Lys Tyr Cys
            35                  40                  45

Lys

```
<210> SEQ ID NO 53
<211> LENGTH: 49
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: Variant of Enterocin 96

<400> SEQUENCE: 53

Met Ala Ser Lys Arg Asp Cys Asn Leu Met Lys Ala Cys Cys Ala Gly
1               5                   10                  15

Leu Ala Val Thr Tyr Ala Ile His Ser Leu Leu Asn Arg Leu Gly Gly
            20                  25                  30

Asp Ser Ser Asp Pro Ala Gly Cys Asn Asp Ile Val Arg Lys Tyr Cys
        35                  40                  45

Lys

<210> SEQ ID NO 54
<211> LENGTH: 49
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: Variant of Enterocin 96

<400> SEQUENCE: 54

Met Ala Ser Lys Arg Asp Cys Asn Leu Met Lys Ala Cys Cys Ala Gly
1               5                   10                  15

Gln Ala Val Thr Tyr Ala Ile His Ser Leu Leu Asn Arg Leu Gly Gly
            20                  25                  30

Asp Pro Ser Asp Pro Ala Gly Cys Asn Asp Ile Val Arg Lys Tyr Cys
        35                  40                  45

Lys

<210> SEQ ID NO 55
<211> LENGTH: 49
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: Variant of Enterocin 96

<400> SEQUENCE: 55

Met Ala Ser Lys Arg Asp Cys Asn Leu Met Lys Ala Cys Cys Ala Gly
1               5                   10                  15

Gln Ala Val Thr Tyr Ala Ile His Ser Leu Leu Asn Arg Leu Gly Gly
            20                  25                  30

Asn Ser Ser Asp Pro Ala Gly Cys Asn Asp Ile Val Arg Lys Tyr Cys
        35                  40                  45

Lys

<210> SEQ ID NO 56
<211> LENGTH: 49
<212> TYPE: PRT
<213> ORGANISM: Artificial Sequence
<220> FEATURE:
<223> OTHER INFORMATION: Synthetic
<220> FEATURE:
```

<221> NAME/KEY: MISC_FEATURE
<223> OTHER INFORMATION: Variant of Enterocin 96

<400> SEQUENCE: 56

Met Ala Ser Lys Arg Asp Cys Asn Leu Met Lys Ala Cys Cys Ala Gly
1               5                   10                  15

Gln Ala Val Thr Tyr Ala Ile His Ser Leu Leu Asn Arg Leu Gly Gly
            20                  25                  30

Asp Phe Ser Asp Pro Ala Gly Cys Asn Asp Ile Val Arg Lys Tyr Cys
        35                  40                  45

Lys

<210> SEQ ID NO 57
<211> LENGTH: 40
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: Variant of Enterocin 96

<400> SEQUENCE: 57

Met Ala Ser Lys Arg Asp Cys Asn Leu Met Lys Ala Cys Cys Ala Gly
1               5                   10                  15

Gln Ala Val Thr Tyr Ala Ile His Ser Leu Leu Asn Arg Leu Gly Gly
            20                  25                  30

Asp Ser Ser Asp Trp Arg Cys Lys
        35                  40

<210> SEQ ID NO 58
<211> LENGTH: 49
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: Variant of Enterocin 96

<400> SEQUENCE: 58

Met Ala Ser Lys Arg Asp Cys Asn Leu Met Lys Ala Cys Cys Ala Gly
1               5                   10                  15

Gln Ala Val Thr Tyr Ala Ile His Ser Leu Leu Asn Arg Leu Gly Gly
            20                  25                  30

Asp Ser Gly Asp Pro Ala Gly Cys Asn Asp Ile Val Arg Lys Tyr Cys
        35                  40                  45

Lys

<210> SEQ ID NO 59
<211> LENGTH: 49
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: Variant of Enterocin 96

<400> SEQUENCE: 59

Met Ala Ser Lys Arg Asp Cys Asn Leu Met Lys Ala Cys Cys Ala Gly
1               5                   10                  15

```
Gln Ala Val Thr Tyr Ala Ile His Ser Leu Leu Asn Arg Leu Gly Gly
                20                  25                  30

Asp Ser Ser Glu Pro Ala Gly Cys Asn Asp Ile Val Arg Lys Tyr Cys
        35                  40                  45

Lys

<210> SEQ ID NO 60
<211> LENGTH: 150
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: enterocin 96 : DNA sequence of enetrocin
      96/ent96
<220> FEATURE:
<221> NAME/KEY: misc_feature
<223> OTHER INFORMATION: enterocin 96 : DNA sequence of enetrocin
      96/ent96 (X) in Acceptor substrate 1 (AS1) in fusion with
      cleavable MCH tag , design of which is described as construct A
      and B of the invention

<400> SEQUENCE: 60
ccatggatga gcaaacgtga ttgtaacttg atgaaggcgt gttgtgctgg acaagcagta      60
acatatgcta ttcatagtct tttaaatcga ttaggtggag actctagtga tccagctggt    120
tgtaatgata ttgtaagaaa atattgtaaa                                      150

<210> SEQ ID NO 61
<211> LENGTH: 122
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Sublancin : DNA sequence of sublancin/sunA
<220> FEATURE:
<221> NAME/KEY: misc_feature
<223> OTHER INFORMATION: Sublancin : DNA sequence of sublancin/sunA (X)
      in Acceptor substrate 1 (AS1) in fusion with cleavable MCH tag ,
      design of which is described as construct A and B of the invention
<220> FEATURE:
<221> NAME/KEY: misc_feature
<223> OTHER INFORMATION: Sublancin : DNA sequence of sublancin/sunA (X)
      in  Acceptor substrate 2 (AS2) in fusion with cleavable MCH tag ,
      design of which is described as construct A and B of the invention

<400> SEQUENCE: 61
ccatggatgg attaggaaaa gctcagtgtg ctgcgttgtg gctacaatgt gctagtggcg      60
gtacaattgg ttgtggtggc ggagctgttg cttgtcaaaa ctatcgtcaa ttctgcagat    120
gc                                                                    122

<210> SEQ ID NO 62
<211> LENGTH: 141
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: glycocin F : DNA sequence of glycocin F/gccF
<220> FEATURE:
<221> NAME/KEY: misc_feature
```

<223> OTHER INFORMATION: glycocin F : DNA sequence of glycocin F/gccF
      (X) in Acceptor substrate 3 (AS3) in fusion with cleavable MCH
      tag , design of which is described as construct A and B of the
      invention

<400> SEQUENCE: 62

| ccatggatga | aacctgcatg | gtgttggtat | actttagcaa | tgtgtggtgc | tggttatgat | 60 |
| tcgggaacct | gtgattatat | gtattcgcat | tgttttggta | taaagcatca | tagtagtggt | 120 |
| agtagcagtt | atcattgtac | c | | | | 141 |

<210> SEQ ID NO 63
<211> LENGTH: 1413
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: entS : Recombinant gene encodes EntS (Y) design
      of which is described as construct A of the invention

<400> SEQUENCE: 63

| catatgtatt | ctgaaaattt | tattgctaat | gactggttta | atgtagaggt | atttaataaa | 60 |
| aataagtata | ctttaacgaa | ccaagagaat | aaagatgtaa | cagaattatg | gttacaaatt | 120 |
| ttaaagggc | taaagttccc | caacgaatta | aggaaactg | tcagttactc | taaaaattta | 180 |
| aaagaattat | ctttaaaaac | tcacgcagaa | gtatctgtat | gtattattgc | taagaatgaa | 240 |
| caggattcaa | taagaaaatg | tattaatagt | atctatgaat | tttcagatga | aattatattt | 300 |
| attgatacag | gatcaattga | ttcgacaaaa | aaaatagtaa | aagaaatagc | aagcgaaaaa | 360 |
| gtaaaaatat | ttgattatac | ttggcaagat | gattttcag | atgcgagaaa | ttattcaata | 420 |
| caaaaagcaa | gtaaagaatg | gatattaatt | attgatgcag | atgaatatgt | atcttcagat | 480 |
| gagcttatca | aattaaggct | cttaatagat | atgttagaca | ggtttaaatt | taaagattca | 540 |
| ttaagagtta | gttgtgcaat | atatcaatta | gataatgtta | tcacacatgg | ccaaagtcga | 600 |
| ttatttagaa | acaataataa | aattaagtat | tatggtctaa | tacatgaaga | gttgaggaac | 660 |
| aacaaaggat | tagatccaat | ttttaacgtt | gaaagtgaga | ttacttttt | ccatgacggt | 720 |
| tacaaagaaa | tacttaggaa | agagaagtgt | gaaagaaaca | taaggctact | agctaagatg | 780 |
| ttagaaaaag | agccagacaa | tgttagatgg | gcatacttgt | attgtagaga | ttcattttct | 840 |
| ataaattcca | acattgattt | tgaaaaaatt | ctacttccat | ttttaataaa | gaatatggat | 900 |
| gaaagtatat | catgtgagaa | tatcctactt | acaaactata | ctcatttaat | cctatttctt | 960 |
| attactaaga | aatatataat | tgatgggaaa | agctcacttg | caagtaaatg | tatagaggtg | 1020 |
| ttagaaaaaa | tgctacctaa | ctcttctgat | gttactttt | acaaattttt | aaataaacag | 1080 |
| catagtttgt | atgaacaaca | atttgaattt | taaaagaag | taattcaatt | tagaaaaaat | 1140 |
| aatgaatatg | atcaatatag | ccaaataggg | tgtaattat | tacactatga | tttattaatt | 1200 |
| tcaggattac | ttttgatgt | taagtcttat | gattattcat | atcaatactt | tttaaaatta | 1260 |
| gatttagcta | actattttc | tgaattagag | attcctgatg | aatacaaaat | gttaataaat | 1320 |
| aagtatcggg | agaatgaatc | actcgagtct | ggtaaagaaa | ccgctgctgc | gaaatttgaa | 1380 |
| cgccagcaca | tggactcgtc | tactagcgca | gct | | | 1413 |

<210> SEQ ID NO 64
<211> LENGTH: 1341
<212> TYPE: DNA

<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: sunS : Recombinant gene encodes SunS (Y) design
of which is described as construct A of the invention

<400> SEQUENCE: 64

| | | | | | |
|---|---|---|---|---|---|
| catatgaaac | tgagtgatat | ttatttggaa | ttaaagaaag | gctatgccga | ttctttattg | 60 |
| tattcagatt | tgtcattgtt | ggttaatata | atggaatatg | aaaaagatat | tgatgtgatg | 120 |
| tcaattcaat | ctttggttgc | aggttatgaa | aaatcagata | ctcctacaat | aacatgcggt | 180 |
| attatagttt | ataacgaaag | caagagaatt | aaaaagtgtt | taaatagtgt | taaagatgat | 240 |
| tttaacgaga | ttattgttct | agattcatac | tccactgatg | ataccgttga | tattattaaa | 300 |
| tgtgattttc | ctgatgttga | aattaaatat | gaaaagtgga | agaatgattt | ttcctatgct | 360 |
| agaaataaaa | ttatagagta | tgctacttcc | gaatggattt | attttattga | tgcagataat | 420 |
| ttatactcta | agaaaacaa | agggaaaata | gctaaagtag | ctagagttttt | agagtttttt | 480 |
| tctattgatt | gtgtagttag | tccatatata | gaagaatata | ctggacatct | atattctgat | 540 |
| acacgaagaa | tgtttcggct | caatggtaaa | gttaaatttc | atgggaaagt | gcatgaagaa | 600 |
| cctatgaatt | ataatcatag | tctacctttt | aatttcattg | tgaaccttaa | ggtttaccat | 660 |
| aatggatata | atccttcaga | gaataatata | aaatcaaaaa | cacgaaggaa | tataaatctc | 720 |
| acagaagaaa | tgttaagatt | ggagcccgaa | aacccaaaat | ggttattctt | tttcggcaga | 780 |
| gaactacatt | tacttgataa | agatgaagaa | gcaattgatt | atctgaaaaa | atcaataaac | 840 |
| aactataaaa | aatttaatga | tcaaagacat | tttatagatg | ctttagtgct | attatgtact | 900 |
| ttattattgc | agagaaataa | ttatgttgac | ttaactttat | atttggatat | attggaaact | 960 |
| gaatatccaa | gatgtgttga | tgttgattac | tttagatctg | caattttgtt | agtagatatg | 1020 |
| caaaataaac | ttacttcttt | aagcaatatg | attgatgaag | ctcttacaga | cgagagatac | 1080 |
| agtgctataa | atacaacaaa | agatcacttt | aaaagaattt | taataagcct | taatattcaa | 1140 |
| ctcgaaaatt | gggaaagagt | aaaagaaata | tcagggggaaa | ttaaaaatga | taatatgaaa | 1200 |
| aaagaaatta | acaatatct | tgccaactca | ctccacaata | ttgaacacgt | cctgaaagga | 1260 |
| attgaagtac | tcgagtctgg | taaagaaacc | gctgctgcga | atttgaacg | ccagcacatg | 1320 |
| gactcgtcta | ctagcgcagc | t | | | | 1341 |

<210> SEQ ID NO 65
<211> LENGTH: 1341
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: gccA : Recombinant gene encodes GccA (Y) design
of which is described as construct A of the invention

<400> SEQUENCE: 65

| | | | | | |
|---|---|---|---|---|---|
| catatgaaaa | atcgccaaaa | tgaaattgac | tcctacctga | atctgcatct | gcgtccggtc | 60 |
| cataaatcct | tcgacttcgg | caacctgacc | aacattgatc | agtttcgtca | tcacatctat | 120 |
| gttagttaca | ttgtcatctg | caaaaactcc | caggcaacga | ttgaacgctg | tgtgaatagt | 180 |
| atcgctcaaa | acatggaaaa | tggcgatgaa | ctgattgttc | tggataccgg | tagcacggac | 240 |
| gaaaccgtgc | atctggtgaa | gaaaaacatg | ccgcaggcga | aaatcagcgt | gaccaactgg | 300 |

```
aaaaacgatt tctctgaagt tcgtaacaaa gcactgaaac tggctagtaa agattgggtc    360
ttctatgtgg attccgacga atggctggac gtcgatgacg gcgcgcagct gaagaaaatt    420
ctgttcaaag ttcaagccaa aaacttcaaa ttcgtcatca atccgacgtt cagcgatcac    480
tctggccaga tttatcaaac cgttggtcgc atcttcccga aaaatctag ctttcattac     540 tacgccaaaa ttcacgaaga agtccgtaaa gaagatcaga actgggcta cgacgtgcgc     600 cattttgcgt gcgatgacat tatcctgtat cacgatggtt acgacaaaga agtgctgcgt    660
gataaagaca aaattaaacg taacatccgc ctgctgcagg aaatgacgtg tgaagaaccg    720
caaaatgcgc gttggccgtt tctgctggcc cgcgatggtt tcgacgttct gccgcaggat    780
aaactgaaac aactggtcaa acgcaccctg gatctggtgg cgtcagactc gctgcaggaa    840
aaatatagcc cgttcgccaa aaaactgctg ggccgtattc tgctgcgcga aggtaaaacc    900
acgcaggcag tgctgtcttt taaagatgtt ctgcaaatca ccggcggtga agattcagac    960
gctatctact acatcgaatc gttcaaaatc aacgaaatta tcgcggaagc caaaagcatc   1020
gaagtgaaaa tgctgcgtta cctgaacaaa cataaaggca tgatcgatgt taacagtgac   1080
atctccggta attattacca cattgcacag gtcatcctgg aatgcgatat tatctcagct   1140
aactactcgc acctgtttcc gctgattagc gaaatcccga aaaatttctc tggcgatatt   1200
aaaagttccg tcaaatctgc ggtcaaactg tattccaaac tgcaaggtga tagtaaaaat   1260
gaaaacaatc tcgagtctgg taagaaaacc gctgctgcga aatttgaacg ccagcacatg   1320
gactcgtcta ctagcgcagc t                                             1341

<210> SEQ ID NO 66
<211> LENGTH: 3829
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: pRSFDuet-1

<400> SEQUENCE: 66
ggggaattgt gagcggataa caattcccct gtagaaataa ttttgtttaa ctttaataag     60
gagatatacc atgggcagca gccatcacca tcatcaccac agccaggatc cgaattcgag    120
ctcggcgcgc ctgcaggtcg acaagcttgc ggccgcataa tgcttaagtc gaacagaaag    180
taatcgtatt gtacacggcc gcataatcga attaatacg actcactata ggggaattgt     240
gagcggataa caattcccca tcttagtata ttagttaagt ataagaagga gatatacata    300
tggcagatct caattggata tcggccggcc acgcgatcgc tgacgtcggt accctcgagt    360
ctggtaaaga aaccgctgct gcgaaatttg aacgccagca catggactcg tctactagcg    420
cagcttaatt aacctaggct gctgccaccg ctgagcaata actagcataa ccccttgggg    480
cctctaaacg ggtcttgagg ggttttttgc tgaaacctca ggcatttgag aagcacacgg    540
tcacactgct tccggtagtc aataaaccgg taaaccagca atagacataa gcggctattt    600
aacgaccctg ccctgaaccg acgacaagct gacgaccggg tctccgcaag tggcactttt    660
cggggaaatg tgcgcggaac ccctatttgt ttatttttct aaatacattc aaatatgtat    720
ccgctcatga attaattctt agaaaaactc atcgagcatc aaatgaaact gcaatttatt    780
catatcagga ttatcaatac catattttg aaaaagccgt ttctgtaatg aaggagaaaa    840
ctcaccgagg cagttccata ggatggcaag atcctggtat cggtctgcga ttccgactcg    900
```

```
tccaacatca atacaaccta ttaatttccc ctcgtcaaaa ataaggttat caagtgagaa    960
atcaccatga gtgacgactg aatccggtga gaatggcaaa agtttatgca tttctttcca   1020
gacttgttca acaggccagc cattacgctc gtcatcaaaa tcactcgcat caaccaaacc   1080
gttattcatt cgtgattgcg cctgagcgag acgaaatacg cggtcgctgt taaaaggaca   1140
attacaaaca ggaatcgaat gcaaccggcg caggaacact gccagcgcat caacaatatt   1200
ttcacctgaa tcaggatatt cttctaatac ctggaatgct gttttcccgg ggatcgcagt   1260
ggtgagtaac catgcatcat caggagtacg gataaaatgc ttgatggtcg aagaggcat    1320
aaattccgtc agccagttta gtctgaccat ctcatctgta acatcattgg caacgctacc   1380
tttgccatgt ttcagaaaca actctggcgc atcgggcttc ccatacaatc gatagattgt   1440
cgcacctgat tgcccgacat tatcgcgagc ccatttatac ccatataaat cagcatccat   1500
gttggaattt aatcgcggcc tagagcaaga cgtttcccgt tgaatatggc tcatactctt   1560
ccttttcaa tattattgaa gcatttatca gggttattgt ctcatgagcg gatacatatt    1620
tgaatgtatt tagaaaaata aacaaatagg catgcagcgc tcttccgctt cctcgctcac   1680
tgactcgcta cgctcggtcg ttcgactgcg gcgagcggtg tcagctcact caaaagcggt   1740
aatacggtta tccacagaat caggggataa cgccggaaag aacatgtgag caaaaagcaa   1800
agcaccggaa gaagccaacg ccgcaggcgt ttttccatag gctccgcccc cctgacgagc   1860
atcacaaaaa tcgacgctca agccagaggt ggcgaaaccc gacaggacta taaagatacc   1920
aggcgtttcc ccctggaagc tccctcgtgc gctctcctgt tccgaccctg ccgcttaccg   1980
gatacctgtc cgcctttctc ccttcgggaa gcgtggcgct ttctcatagc tcacgctgtt   2040
ggtatctcag ttcggtgtag gtcgttcgct ccaagctggg ctgtgtgcac gaaccccccg   2100
ttcagcccga ccgctgcgcc ttatccggta actatcgtct tgagtccaac ccggtaagac   2160
acgacttatc gccactggca gcagccattg gtaactgatt tagaggactt tgtcttgaag   2220
ttatgcacct gttaaggcta aactgaaaga acagattttg gtgagtgcgg tcctccaacc   2280
cacttacctt ggttcaaaga gttggtagct cagcgaacct tgagaaaacc accgttggta   2340
gcggtggttt ttcttttattt atgagatgat gaatcaatcg gtctatcaag tcaacgaaca   2400
gctattccgt tactctagat ttcagtgcaa tttatctctt caaatgtagc acctgaagtc   2460
agccccatac gatataagtt gtaattctca tgttagtcat gccccgcgcc caccggaagg   2520
agctgactgg gttgaaggct ctcaagggca tcggtcgaga tcccggtgcc taatgagtga   2580
gctaacttac attaattgcg ttgcgctcac tgcccgcttt ccagtcggga aacctgtcgt   2640
gccagctgca ttaatgaatc ggccaacgcg cggggagagg cggtttgcgt attgggcgcc   2700
agggtggttt ttcttttcac cagtgagacg ggcaacagct gattgccctt caccgcctgg   2760
ccctgagaga gttgcagcaa gcggtccacg ctggtttgcc ccagcaggcg aaaatcctgt   2820
ttgatggtgg ttaacggcgg gatataacat gagctgtctt cggtatcgtc gtatcccact   2880
accgagatgt ccgcaccaac gcgcagcccg gactcggtaa tggcgcgcat tgcgcccagc   2940
gccatctgat cgttggcaac cagcatcgca gtgggaacga tgccctcatt cagcatttgc   3000
atggtttgtt gaaaaccgga catggcactc cagtcgcctt cccgttccgc tatcggctga   3060
atttgattgc gagtgagata tttatgccag ccagccagac gcagacgcgc cgagacagaa   3120
cttaatgggc ccgctaacag cgcgatttgc tggtgaccca atgcgaccag atgctccacg   3180
cccagtcgcg taccgtcttc atgggagaaa ataatactgt tgatgggtgt ctggtcagag   3240
```

-continued

| | |
|---|---|
| acatcaagaa ataacgccgg aacattagtg caggcagctt ccacagcaat ggcatcctgg | 3300 |
| tcatccagcg gatagttaat gatcagccca ctgacgcgtt gcgcgagaag attgtgcacc | 3360 |
| gccgctttac aggcttcgac gccgcttcgt tctaccatcg acaccaccac gctggcaccc | 3420 |
| agttgatcgg cgcgagattt aatcgccgcg acaatttgcg acggcgcgtg cagggccaga | 3480 |
| ctggaggtgg caacgccaat cagcaacgac tgtttgcccg ccagttgttg tgccacgcgg | 3540 |
| ttgggaatgt aattcagctc cgccatcgcc gcttccactt tttcccgcgt tttcgcagaa | 3600 |
| acgtggctgg cctggttcac cacgcgggaa acggtctgat aagagacacc ggcatactct | 3660 |
| gcgacatcgt ataacgttac tggttttcaca ttcaccaccc tgaattgact ctcttccggg | 3720 |
| cgctatcatg ccataccgcg aaaggttttg cgccattcga tggtgtccgg gatctcgacg | 3780 |
| ctctccctta tgcgactcct gcattaggaa attaatacga ctcactata | 3829 |

<210> SEQ ID NO 67
<211> LENGTH: 6706
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: pTXB1

<400> SEQUENCE: 67

| | |
|---|---|
| aactacgtca ggtggcactt ttcggggaaa tgtgcgcgga acccctattt gtttattttt | 60 |
| ctaaatacat tcaaatatgt atccgctcat gagacaataa ccctgataaa tgcttcaata | 120 |
| atattgaaaa aggaagagta tgagtattca acatttccgt gtcgccctta ttccctttt | 180 |
| tgcggcattt tgccttcctg tttttgctca cccagaaacg ctggtgaaag taaaagatgc | 240 |
| tgaagatcag ttgggtgcac gagtgggtta catcgaactg gatctcaaca gcggtaagat | 300 |
| ccttgagagt tttcgccccg aagaacgttc tccaatgatg agcacttta aagttctgct | 360 |
| atgtggcgcg gtattatccc gtgttgacgc cgggcaagag caactcggtc gccgcataca | 420 |
| ctattctcag aatgacttgg ttgagtactc accagtcaca gaaaagcatc ttacggatgg | 480 |
| catgacagta agagaattat gcagtgctgc cataaccatg agtgataaca ctgcggccaa | 540 |
| cttacttctg acaacgatcg gaggaccgaa ggagctaacc gcttttttgc acaacatggg | 600 |
| ggatcatgta actcgccttg atcgttggga accggagctg aatgaagcca taccaaacga | 660 |
| cgagcgtgac accacgatgc ctgtagcaat ggcaacaacg ttgcgcaaac tattaactgg | 720 |
| cgaactactt actctagctt cccggcaaca attaatagac tggatggagg cggataaagt | 780 |
| tgcaggacca cttctgcgct cggcccttcc ggctggctgg tttattgctg ataaatctgg | 840 |
| agccggtgag cgtgggtctc gcggtatcat tgcagcactg gggccagatg gtaagccctc | 900 |
| ccgtatcgta gttatctaca cgacggggag tcaggcaact atggatgaac gaaatagaca | 960 |
| gatcgctgag ataggtgcct cactgattaa gcattggtaa ctgtcagacc aagtttactc | 1020 |
| atatatactt tagattgatt taccccggtt gataatcaga aaagcccaa aaacaggaag | 1080 |
| attgtataag caaatattta aattgtaaac gttaatattt tgttaaaatt cgcgttaaat | 1140 |
| ttttgttaaa tcagctcatt ttttaaccaa taggccgaaa tcggcaaaat cccttataaa | 1200 |
| tcaaaagaat agcccgagat agggttgagt gttgttccag tttggaacaa gagtccacta | 1260 |
| ttaaagaacg tggactccaa cgtcaaaggg cgaaaaaccg tctatcaggg cgatggccca | 1320 |
| ctacgtgaac catcacccaa atcaagtttt ttggggtcga ggtgccgtaa agcactaaat | 1380 |

| | |
|---|---|
| cggaacccta aagggagccc ccgatttaga gcttgacggg gaaagccggc gaacgtggcg | 1440 |
| agaaaggaag ggaagaaagc gaaaggagcg ggcgctaggg cgctggcaag tgtagcggtc | 1500 |
| acgctgcgcg taaccaccac acccgccgcg cttaatgcgc cgctacaggg cgcgtaaaag | 1560 |
| gatctaggtg aagatccttt ttgataatct catgaccaaa atcccttaac gtgagttttc | 1620 |
| gttccactga gcgtcagacc ccgtagaaaa gatcaaagga tcttcttgag atcctttttt | 1680 |
| tctgcgcgta atctgctgct tgcaaacaaa aaaaccaccg ctaccagcgg tggtttgttt | 1740 |
| gccggatcaa gagctaccaa ctcttttcc gaaggtaact ggcttcagca gagcgcagat | 1800 |
| accaaatact gtccttctag tgtagccgta gttaggccac cacttcaaga actctgtagc | 1860 |
| accgcctaca tacctcgctc tgctaatcct gttaccagtg gctgctgcca gtggcgataa | 1920 |
| gtcgtgtctt accgggttgg actcaagacg atagttaccg gataaggcgc agcggtcggg | 1980 |
| ctgaacgggg ggttcgtgca cacagcccag cttggagcga acgacctaca ccgaactgag | 2040 |
| atacctacag cgtgagctat gagaaagcgc cacgcttccc gaaggagaa aggcggacag | 2100 |
| gtatccggta agcggcaggg tcggaacagg agagcgcacg agggagcttc caggggaaa | 2160 |
| cgcctggtat ctttatagtc ctgtcgggtt tcgccacctc tgacttgagc gtcgattttt | 2220 |
| gtgatgctcg tcaggggggc ggagcctatg gaaaaacgcc agcaacgcgg cctttttacg | 2280 |
| gttcctggcc ttttgctggc cttttgctca catgttcttt cctgcgttat cccctgattc | 2340 |
| tgtggataac cgtattaccg cctttgagtg agctgatacc gctcgccgca gccgaacgac | 2400 |
| cgagcgcagc gagtcagtga gcgaggaagc tatggtgcac tctcagtaca atctgctctg | 2460 |
| atgccgcata gttaagccag tatacactcc gctatcgcta cgtgactggg tcatggctgc | 2520 |
| gccccgacac ccgccaacac ccgctgacgc gccctgacgg gcttgtctgc tcccggcatc | 2580 |
| cgcttacaga caagctgtga ccgtctccgg gagctgcatg tgtcagaggt tttcaccgtc | 2640 |
| atcaccgaaa cgcgcgaggc agctgcggta aagctcatca gcgtggtcgt gcagcgattc | 2700 |
| acagatgtct gcctgttcat ccgcgtccag ctcgttgagt ttctccagaa gcgttaatgt | 2760 |
| ctggcttctg ataaagcggg ccatgttaag ggcggttttt tcctgtttgg tcactgatgc | 2820 |
| ctccgtgtaa gggggatttc tgttcatggg ggtaatgata ccgatgaaac gagagaggat | 2880 |
| gctcacgata cgggttactg atgatgaaca tgcccggtta ctggaacgtt gtgagggtaa | 2940 |
| acaactggcg gtatggatgc ggcgggacca gagaaaaatc actcagggtc aatgccagcc | 3000 |
| gaacgccagc aagacgtagc ccagcgcgtc ggccgccatg ccggcgataa tggcctgctt | 3060 |
| ctcgccgaaa cgtttggtgg cgggaccagt gacgaaggct tgagcgaggg cgtgcaagat | 3120 |
| tccgaatacc gcaagcgaca ggccgatcat cgtcgcgctc cagcgaaagc ggtcctcgcc | 3180 |
| gaaaatgacc cagagcgctg ccggcacctg tcctacgagt tgcatgataa agaagacagt | 3240 |
| cataagtgcg gcgacgatag tcatgccccg cgcccaccgg aaggagctga ctgggttgaa | 3300 |
| ggctctcaag ggcatcggtc gagatccgg tgcctaatga gtgagctaac ttacattaat | 3360 |
| tgcgttgcgc tcactgcccg ctttccagtc gggaaacctg tcgtgccagc tgcattaatg | 3420 |
| aatcggccaa cgcgcgggga gaggcggttt gcgtattggg cgccagggtg ttttttcttt | 3480 |
| tcaccagtga gacgggcaac agctgattgc ccttcaccgc ctggccctga gagagttgca | 3540 |
| gcaagcggtc cacgctggtt tgccccagca ggcgaaaatc ctgtttgatg gtggttaacg | 3600 |
| gcgggatata acatgagctg tcttcggtat cgtcgtatcc cactaccgag atatccgcac | 3660 |
| caacgcgcag cccggactcg gtaatggcgc gcattgcgcc cagcgccatc tgatcgttgg | 3720 |
| caaccagcat cgcagtggga acgatgccct cattcagcat ttgcatggtt tgttgaaaac | 3780 |

```
cggacatggc actccagtcg ccttcccgtt ccgctatcgg ctgaatttga ttgcgagtga    3840
gatatttatg ccagccagcc agacgcagac gcgccgagac agaacttaat gggcccgcta    3900
acagcgcgat ttgctggtga cccaatgcga ccagatgctc cacgcccagt cgcgtaccgt    3960
cttcatggga gaaataata ctgttgatgg gtgtctggtc agagacatca agaaataacg    4020
ccggaacatt agtgcaggca gcttccacag caatggcatc ctggtcatcc agcggatagt    4080
taatgatcag cccactgacg cgttgcgcga aagattgtg caccgccgct ttacaggctt    4140
cgacgccgct tcgttctacc atcgacacca ccacgctggc acccagttga tcggcgcgag    4200
atttaatcgc cgcgacaatt tgcgacgcg cgtgcagggc cagactggag gtggcaacgc    4260
caatcagcaa cgactgtttg cccgccagtt gttgtgccac gcggttggga atgtaattca    4320
gctccgccat cgccgcttcc actttttccc gcgttttcgc agaaacgtgg ctggcctggt    4380
tcaccacgcg ggaaacggtc tgataagaga caccggcata ctctgcgaca tcgtataacg    4440
ttactggttt cacattcacc accctgaatt gactctcttc cgggcgctat catgccatac    4500
cgcgaaaggt tttgcgccat tcgatggtgt ccgggatctc gacgctctcc cttatgcgac    4560
tcctgcatta ggaagcagcc cagtagtagg ttgaggccgt tgagcaccgc cgccgcaagg    4620
aatggtgcat gccggcatgc cgcccttcg tcttcaagaa ttaattccca attccccagg    4680
catcaaataa aacgaaaggc tcagtcgaaa gactgggcct ttcgttttat ctgttgtttg    4740
tcggtgaacg ctctcctgag taggacaaat ccgccgggag cggatttgaa cgttgcgaag    4800
caacggcccg gagggtggcg ggcaggacgc ccgccataaa ctgccaggaa ttaattcccc    4860
aggcatcaaa taaaacgaaa ggctcagtcg aaagactggg cctttcgttt tatctgttgt    4920
ttgtcggtga acgctctcct gagtaggaca atccgccgg gagcggattt gaacgttgcg    4980
aagcaacggc ccgagggtg gcgggcagga cgcccgccat aaactgccag gaattaattc    5040
cccaggcatc aaataaaacg aaaggctcag tcgaaagact gggcctttcg ttttatctgt    5100
tgtttgtcgg tgaacgctct cctgagtagg acaaatccgc cgggagcgga tttgaacgtt    5160
gcgaagcaac ggcccggagg gtggcgggca ggacgcccgc cataaactgc caggaattaa    5220
ttccccaggc atcaaataaa acgaaaggct cagtcgaaag actgggcctt tcgttttatc    5280
tgttgtttgt cggtgaacgc tctcctgagt aggacaaatc cgccgggagc ggatttgaac    5340
gttgcgaagc aacggcccgg agggtggcgg gcaggacgcc cgccataaac tgccaggaat    5400
taattcccca ggcatcaaat aaaacgaaag gctcagtcga aagactgggc ctttcgtttt    5460
atctgttgtt tgtcggtgaa cgctctcctg agtaggacaa atccgccggg agcggatttg    5520
aacgttgcga agcaacggcc cggagggtgg cgggcaggac gcccgccata aactgccagg    5580 aattgggat cggaattaat tcccggttta accggggat ctcgatcccg cgaaattaat    5640
acgactcact ataggggaat tgtgagcgga taacaattcc cctctagaaa taattttgtt    5700
taactttaag aaggagatat acatatggct agctcgcgag tcgacggcgg ccgcgaattc    5760
ctcgagggct cttcctgcat cacgggagat gcactagttg ccctacccga gggcgagtcg    5820
gtacgcatcg ccgacatcgt gccgggtgcg cggcccaaca gtgacaacgc catcgacctg    5880
aaagtccttg accggcatgg caatcccgtg ctcgccgacc ggctgttcca ctccggcgag    5940
catccggtgt acacggtgcg tacggtcgaa ggtctgcgtg tgacgggcac cgcgaaccac    6000
ccgttgttgt gtttggtcga cgtcgccggg gtgccgaccc tgctgtggaa gctgatcgac    6060
gaaatcaagc cgggcgatta cgcggtgatt caacgcagcg cattcagcgt cgactgtgca    6120
```

| | | |
|---|---|---|
| ggttttgccc gcgggaaacc cgaatttgcg cccacaacct acacagtcgg cgtccctgga | 6180 | |
| ctggtgcgtt tcttggaagc acaccaccga gacccggacg cccaagctat cgccgacgag | 6240 | |
| ctgaccgacg ggcggttcta ctacgcgaaa gtcgccagtg tcaccgacgc cggcgtgcag | 6300 | |
| ccggtgtata gccttcgtgt cgacacggca gaccacgcgt ttatcacgaa cgggttcgtc | 6360 | |
| agccacgcta ctggcctcac cggtctgaac tcaggcctca cgacaaatcc tggtgtatcc | 6420 | |
| gcttggcagg tcaacacagc ttatactgcg ggacaattgg tcatatataa cggcaagacg | 6480 | |
| tataaatgtt tgcagcccca cacctccttg gcaggatggg aaccatccaa cgttcctgcc | 6540 | |
| ttgtggcagc ttcaatgact gcaggaaggg gatccggctg ctaacaaagc ccgaaaggaa | 6600 | |
| gctgagttgg ctgctgccac cgctgagcaa taactagcat aacccctggg ggcctctaaa | 6660 | |
| cgggtcttga ggggttttttt gctgaaagga ggaactatat ccggat | 6706 | |

<210> SEQ ID NO 68
<211> LENGTH: 3829
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: pRSFDuet-1_SapI

<400> SEQUENCE: 68

| | | |
|---|---|---|
| ggggaattgt gagcggataa caattcccct gtagaaataa ttttgtttaa ctttaataag | 60 | |
| gagatatacc atgggcagca gccatcacca tcatcaccac agccaggatc cgaattcgag | 120 | |
| ctcggcgcgc ctgcaggtcg acaagcttgc ggccgcataa tgcttaagtc gaacagaaag | 180 | |
| taatcgtatt gtacacggcc gcataatcga attaatacg actcactata ggggaattgt | 240 | |
| gagcggataa caattcccca tcttagtata ttagttaagt ataagaagga gatatacata | 300 | |
| tggcagatct caattggata tcggccggcc acgcgatcgc tgacgtcggt accctcgagt | 360 | |
| ctggtaaaga accgctgct gcgaaatttg aacgccagca catggactcg tctactagcg | 420 | |
| cagcttaatt aacctaggct gctgccaccg ctgagcaata actagcataa ccccttgggg | 480 | |
| cctctaaacg ggtcttgagg ggttttttgc tgaaacctca ggcatttgag aagcacacgg | 540 | |
| tcacactgct tccggtagtc aataaaccgg taaaccagca atagacataa gcggctattt | 600 | |
| aacgaccctg ccctgaaccg acgacaagct gacgaccggg tctccgcaag tggcactttt | 660 | |
| cggggaaatg tgcgcggaac ccctatttgt ttatttttct aaatacattc aaatatgtat | 720 | |
| ccgctcatga attaattctt agaaaaactc atcgagcatc aaatgaaact gcaatttatt | 780 | |
| catatcagga ttatcaatac catattttg aaaagccgt ttctgtaatg aaggagaaaa | 840 | |
| ctcaccgagg cagttccata ggatggcaag atcctggtat cggtctgcga ttccgactcg | 900 | |
| tccaacatca atacaaccta ttaatttccc ctcgtcaaaa ataaggttat caagtgagaa | 960 | |
| atcaccatga gtgacgactg aatccggtga gaatggcaaa agtttatgca tttctttcca | 1020 | |
| gacttgttca acaggccagc cattacgctc gtcatcaaaa tcactcgcat caaccaaacc | 1080 | |
| gttattcatt cgtgattgcg cctgagcgag acgaaatacg cggtcgctgt taaaaggaca | 1140 | |
| attacaaaca ggaatcgaat gcaaccggcg caggaacact gccagcgcat caacaatatt | 1200 | |
| ttcacctgaa tcaggatatt cttctaatac ctggaatgct gttttcccgg ggatcgcagt | 1260 | |
| ggtgagtaac catgcatcat caggagtacg gataaaatgc ttgatggtcg gaagaggcat | 1320 | |
| aaattccgtc agccagttta gtctgaccat ctcatctgta acatcattgg caacgctacc | 1380 | |

```
tttgccatgt tcagaaaca actctggcgc atcgggcttc ccatacaatc gatagattgt    1440
cgcacctgat tgcccgacat tatcgcgagc ccatttatac ccatataaat cagcatccat    1500
gttggaattt aatcgcggcc tagagcaaga cgtttcccgt tgaatatggc tcatactctt    1560 ccttttcaa tattattgaa gcatttatca gggttattgt ctcatgagcg gatacatatt    1620
tgaatgtatt tagaaaaata acaaatagg catgcagcgc agatccgctt cctcgctcac    1680
tgactcgcta cgctcggtcg ttcgactgcg gcgagcggtg tcagctcact caaaagcggt    1740
aatacggtta tccacagaat caggggataa agccggaaag aacatgtgag caaaaagcaa    1800
agcaccggaa gaagccaacg ccgcaggcgt ttttccatag gctccgcccc cctgacgagc    1860
atcacaaaaa tcgacgctca agccagaggt ggcgaaaccc gacaggacta taaagatacc    1920
aggcgtttcc ccctggaagc tccctcgtgc gctctcctgt tccgaccctg ccgcttaccg    1980
gatacctgtc cgcctttctc ccttcgggaa gcgtggcgct ttctcatagc tcacgctgtt    2040
ggtatctcag ttcggtgtag gtcgttcgct ccaagctggg ctgtgtgcac gaaccccccg    2100
ttcagcccga ccgctgcgcc ttatccggta actatcgtct tgagtccaac ccggtaagac    2160
acgacttatc gccactggca gcagccattg gtaactgatt tagaggactt tgtcttgaag    2220
ttatgcacct gttaaggcta aactgaaaga acagattttg gtgagtgcgg tcctccaacc    2280
cacttacctt ggttcaaaga gttggtagct cagcgaacct tgagaaaacc accgttggta    2340
gcggtggttt tctttatt atgagatgat gaatcaatcg gtctatcaag tcaacgaaca    2400
gctattccgt tactctagat ttcagtgcaa tttatctctt caaatgtagc acctgaagtc    2460
agccccatac gatataagtt gtaattctca tgttagtcat gccccgcgcc caccggaagg    2520
agctgactgg gttgaaggct ctcaagggca tcggtcgaga tcccggtgcc taatgagtga    2580
gctaacttac attaattgcg ttgcgctcac tgcccgcttt ccagtcggga acctgtcgt    2640 gccagctgca ttaatgaatc ggccaacgcg cgggagagg cggtttgcgt attgggcgcc    2700
agggtggttt ttcttttcac cagtgagacg ggcaacagct gattgccctt caccgcctgg    2760
ccctgagaga gttgcagcaa gcggtccacg ctggtttgcc ccagcaggcg aaaatcctgt    2820
ttgatggtgg ttaacggcgg gatataacat gagctgtctt cggtatcgtc gtatcccact    2880
accgagatgt ccgcaccaac gcgcagcccg gactcggtaa tggcgcgcat tgcgcccagc    2940
gccatctgat cgttggcaac cagcatcgca gtgggaacga tgccctcatt cagcatttgc    3000
atggtttgtt gaaaaccgga catggcactc cagtcgcctt cccgttccgc tatcggctga    3060
atttgattgc gagtgagata tttatgccag ccagccagac gcagacgcgc cgagacagaa    3120
cttaatgggc ccgctaacag cgcgatttgc tggtgaccca atgcgaccag atgctccacg    3180
cccagtcgcg taccgtcttc atgggagaaa ataatactgt tgatgggtgt ctggtcagag    3240
acatcaagaa ataacgccgg aacattagtg caggcagctt ccacagcaat ggcatcctgg    3300
tcatccagcg gatagttaat gatcagccca ctgacgcgtt gcgcgagaag attgtgcacc    3360
gccgctttac aggcttcgac gccgcttcgt tctaccatcg acaccaccac gctggcaccc    3420
agttgatcgg cgcgagattt aatcgccgcg acaatttgcg acggcgcgtg cagggccaga    3480
ctggaggtgg caacgccaat cagcaacgac tgtttgcccg ccagttgttg tgccacgcgg    3540
ttgggaatgt aattcagctc cgccatcgcc gcttccactt tttcccgcgt tttcgcagaa    3600
acgtggctgg cctggttcac cacgcgggaa acggtctgat aagagacacc ggcatactct    3660
gcgacatcgt ataacgttac tggtttcaca ttcaccaccc tgaattgact ctcttccggg    3720
```

```
cgctatcatg ccataccgcg aaaggttttg cgccattcga tggtgtccgg gatctcgacg    3780
ctctccctta tgcgactcct gcattaggaa attaatacga ctcactata               3829
```

We claim:

1. A recombinant microbial system for synthesis of libraries of O- and S-linked neo-glycocins, and directed evolution thereof, wherein the recombinant microbial system comprises:
   a) a cloning vector pRSF Duet-1SapI having the nucleotide sequence as set forth in SEQ ID NO: 68;
   b) a gene cassette A comprising a DNA sequence encoding glycosyltransferase, and a DNA sequence encoding an acceptor sequence having a polynucleotide sequence as set forth in sequence selected from the group consisting of SEQ ID NO: 1, SEQ ID NO: 2, SEQ ID NO: 3, SEQ ID NO: 4 and SEQ ID NO: 5; and
   c) a host cell.

2. The recombinant microbial system as claimed in claim 1, wherein the recombinant microbial system further comprises:
   an additional vector comprising a gene cassette B having a DNA sequence encoding an acceptor sequence.

3. The recombinant microbial system as claimed in claim 2, wherein the additional vector is selected from the group consisting of pRSFDuet-1 having polynucleotide sequence as set forth in SEQ ID NO: 66, pRSF Duet-1SapI having polynucleotide sequence as set forth in SEQ ID NO: 68 and pTXB1 having polynucleotide sequence as set forth in SEQ ID NO: 67.

4. The recombinant microbial system as claimed in claim 1, wherein the acceptor sequence is tagged with dual affinity cleavable tags to provide an acceptor substrate fusion protein AS1 having the amino acid sequence as set forth in SEQ ID NO: 6, AS2 having the amino acid sequence as set forth in SEQ ID NO: 7, or AS3 having the amino acid sequence as set forth in SEQ ID NO: 8.

5. The recombinant microbial system as claimed in claim 1, wherein the acceptor sequence is selected from the group consisting of a polypeptide, a peptide, an antimicrobial peptide, a bacteriocin and a glycocin.

6. The recombinant microbial system as claimed in claim 1, wherein the host cell is E. coli.

7. A method for constructing a recombinant microbial system the method comprising:
   a. mutating the nucleotide sequence of a pRSFDuet-1vector by site directed mutagenesis using a primer having sequence as set forth in SEQ ID NO: 12 to obtain a vector 1, wherein the vector 1 is pRSFDuet-1SapI vector;
   b. amplifying and sub cloning a polynucleotide sequence having the sequence selected from the group consisting of SEQ ID NO: 63, SEQ ID NO: 64 and SEQ ID NO: 65 encoding a glycosyltransferase using primers in the vector 1 of step (a) to obtain a vector 2;
   c. amplifying and sub cloning an acceptor substrate gene having a polynucleotide sequence selected from the group consisting of SEQ ID NO: 60, SEQ ID NO: 61 and SEQ ID NO: 62 using primers in the vector 2 of step (b) to obtain a vector 3;
   d. amplifying and subcloning a nucleotide sequence encoding a fusion tag MC from a vector 4 using primers in the vector 3 of step (c) to obtain a vector 5;
   e. extending the fusion tag MC in the vector 5 of step (d) using primers to obtain a vector 6;
   f. amplifying and sub cloning an acceptor substrate gene having a polynucleotide sequence selected from the group consisting of SEQ ID NO: 60, SEQ ID NO: 61 and SEQ ID NO: 62 using primers in NcoI and SapI sites of the vector 6 of step (e) to generate a vector comprising a gene cassette A, the gene cassette A having a polynucleotide sequence as set forth in a sequence selected from the group consisting of SEQ ID NO: 1, SEQ ID NO: 2, SEQ ID NO: 3, SEQ ID NO: 4 and SEQ ID NO: 5; and
   g. transforming the vector comprising the gene cassette A of step (f) in an E. coli to obtain the recombinant microbial system.

8. The method as claimed in claim 7, wherein the vector 2 is selected from the group consisting of EntSpRSFDuet-1SapI, SunSpRSFDuet-1SapI and GccApRSFDuet-1SapI vector.

9. The method as claimed in claim 7, wherein the vector 3 is selected from the group consisting of EntSAS1pRSFDuet-1SapI, EntSAS2pRSFDuet-1Sap1, EntSAS3pRSFDuet-1Sap1, SunSSAS2pRSFDuet-1Sap1 and GccAAS3pRSFDuet-1Sap1vector.

10. The method as claimed in claim 7, wherein the vector 4 is selected from the group consisting of pTWIN1, pTXB1 and pTXB3.

11. The method as claimed in claim 7, wherein the vector 5 is selected from the group consisting of EntSAS1MCpRSFDuet-1SapI, EntSAS2MCpRSFDuet-1Sap1, EntSAS3MCpRSFDuet-1Sap1, SunSSAS2MCpRSFDuet-1Sap1 and GccAAS3MCpRSFDuet-1 Sap1.

12. The method as claimed in claim 7, wherein the vector 6 is selected from the group consisting of EntSAS1MCHpRSFDuet-1SapI, EntSAS2MCHpRSFDuet-1Sap1, EntSAS3MCHpRSFDuet-1Sap1, SunSSAS2MCHpRSFDuet-1Sap1 and GccAAS3MCHpRSFDuet-1SapI.

13. The method as claimed in claim 7, wherein the primers are having have sequences selected from the group consisting of SEQ ID NO: 13, SEQ ID NO:14, SEQ ID NO:15, SEQ ID NO: 16, SEQ ID NO: 17, SEQ ID NO: 18, SEQ ID NO: 19, SEQ ID NO:20, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:34, SEQ ID NO:35, SEQ ID NO:36, SEQ ID NO:37, SEQ ID NO:38 and SEQ ID NO:39.

14. A method for generation and screening of libraries of O- and S-linked neoglycocins and directed evolution thereof using a recombinant microbial system comprising a) a cloning vector pRSF Duet-1SapI having the nucleotide sequence as set forth in SEQ ID NO: 68; b) a gene cassette A comprising a DNA sequence encoding glycosyltransferase, and a DNA sequence encoding an acceptor sequence having a polynucleotide sequence as set forth in sequence selected from the group consisting of SEQ ID NO: 1, SEQ ID NO: 2, SEQ ID NO: 3, SEQ ID NO: 4 and SEQ ID NO: 5; and c) a host cell, the method comprising:

i. mutating the gene cassette A obtained in claim 7 using a method selected from random mutagenesis or site directed mutagenesis to obtain a mutated gene cassette A libraries;

ii. expressing the mutated gene cassette A of step (i) in an *E. coli* to obtain fusion protein libraries;

iii. obtaining cleavage buffer treated cell lysates of the fusion protein libraries of step (ii) to obtain cleaved peptides in cell lysates; and iv. screening the cleaved peptides of step (iii) for an antimicrobial activity using agar diffusion test (ADT) against an indicator bacterial strain selected from the group consisting of *L. monocytogenes, Vibrio cholera* MTCC 3904, *Listeria monocytogenes* MTCC 839, *E. coli* MTCC 1610, *Bacillus halodurans* MTCC 7181 and *Bacillus licheniformis* MTCC9857 to obtain the neo-glycocin.

15. The method as claimed in claim 14, wherein the neo-glycocin obtained has an amino acid sequence as set forth in a sequence selected from the group consisting of SEQ ID NO: 10, SEQ ID NO: 11, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, and SEQ ID NO: 59.

16. A method for enhancing the expression and purification of a neo-glycocin, the method comprising co-transforming the gene cassette A and the gene cassette B of the recombinant microbial system of claim 2.

* * * * *